(12) United States Patent
Fulton, III

(10) Patent No.: US 12,642,544 B2
(45) Date of Patent: Jun. 2, 2026

(54) FUNNEL CATHETER AND NOVEL METHODS OF UTILIZATION

(71) Applicant: Vascular Development Corp, LLC, Grand Junction, CO (US)

(72) Inventor: Richard E. Fulton, III, Grand Junction, CO (US)

(73) Assignee: Vascular Development Corp, LLC, Grand Junction, CO (US)

( * ) Notice: Subject to any disclaimer, the term of this patent is extended or adjusted under 35 U.S.C. 154(b) by 444 days.

(21) Appl. No.: 18/515,967

(22) Filed: Nov. 21, 2023

(65) Prior Publication Data

US 2024/0237998 A1     Jul. 18, 2024

Related U.S. Application Data

(63) Continuation of application No. PCT/US2022/031404, filed on May 27, 2022.

(60) Provisional application No. 63/309,028, filed on Feb. 11, 2022, provisional application No. 63/193,614, filed on May 27, 2021.

(51) Int. Cl.
| | |
|---|---|
| *A61B 17/22* | (2006.01) |
| *A61B 17/00* | (2006.01) |
| *A61B 17/12* | (2006.01) |
| *A61B 17/221* | (2006.01) |

(52) U.S. Cl.
CPC .. *A61B 17/22012* (2013.01); *A61B 17/00234* (2013.01); *A61B 17/12031* (2013.01); *A61B 17/12109* (2013.01); *A61B 17/12172* (2013.01); *A61B 17/221* (2013.01); *A61B 2017/00238* (2013.01); *A61B 2017/00305* (2013.01); *A61B 2017/1205* (2013.01); *A61B*

*2017/22038* (2013.01); *A61B 2017/22065* (2013.01); *A61B 2017/22074* (2013.01);
(Continued)

(58) Field of Classification Search
CPC .......... A61B 2017/2215; A61B 17/221; A61B 2217/005; A61B 2017/22079; A61B 17/1204; A61B 17/12168; A61B 17/12177; A61B 2017/320716; A61B 17/12036
See application file for complete search history.

(56) References Cited

U.S. PATENT DOCUMENTS

| | | | |
|---|---|---|---|
| 2,230,226 | A | 2/1941 | Auzin |
| 2,259,488 | A | 10/1941 | Raiche |

(Continued)

FOREIGN PATENT DOCUMENTS

| | | |
|---|---|---|
| EP | 0983749 A2 | 3/2000 |
| EP | 1030603 A1 | 8/2000 |

(Continued)

OTHER PUBLICATIONS

EP22812291.7 Extended European Search Report dated Apr. 28, 2025.

(Continued)

*Primary Examiner* — William R Carpenter
(74) *Attorney, Agent, or Firm* — Wilson Sonsini Goodrich & Rosati

(57) ABSTRACT

Disclosed herein are devices, systems, and methods useful in facilitating the removal of thrombus, embolus, or debris from a blood vessel and other intravascular interventional actions, including proximal embolic protection when treating a vascular lesion or condition.

20 Claims, 22 Drawing Sheets

(52) U.S. Cl.
CPC .............. *A61B 2017/22079* (2013.01); *A61B 2017/22084* (2013.01); *A61B 2017/2215* (2013.01); *A61B 2217/005* (2013.01)

(56) References Cited

U.S. PATENT DOCUMENTS

| | | | |
|---|---|---|---|
| 3,050,066 A | 8/1962 | Koehn |
| 3,540,431 A | 11/1970 | Kazi |
| 3,799,172 A | 3/1974 | Szpur |
| 3,831,587 A | 8/1974 | Boyd |
| 3,834,394 A | 9/1974 | Hunter et al. |
| 3,952,747 A | 4/1976 | Kimmell, Jr. |
| 3,978,863 A | 9/1976 | Fettel et al. |
| 3,996,938 A | 12/1976 | Clark, III |
| 4,030,503 A | 6/1977 | Clark, III |
| 4,372,293 A | 2/1983 | Vijil-Rosales |
| 4,401,124 A | 8/1983 | Guess et al. |
| 4,425,908 A | 1/1984 | Simon |
| 4,445,892 A | 5/1984 | Hussein et al. |
| 4,494,531 A | 1/1985 | Gianturco |
| 4,573,966 A | 3/1986 | Weikl et al. |
| 4,581,017 A | 4/1986 | Sahota et al. |
| 4,582,061 A | 4/1986 | Fry |
| 4,606,347 A | 8/1986 | Fogarty et al. |
| 4,608,965 A | 9/1986 | Anspach, Jr. et al. |
| 4,611,594 A | 9/1986 | Grayhack et al. |
| 4,621,636 A | 11/1986 | Fogarty |
| 4,646,736 A | 3/1987 | Auth |
| 4,650,466 A | 3/1987 | Luther |
| 4,696,304 A | 9/1987 | Chin |
| 4,727,873 A | 3/1988 | Mobin-Uddin |
| 4,762,130 A | 8/1988 | Fogarty et al. |
| 4,793,348 A | 12/1988 | Palmaz |
| 4,794,925 A | 1/1989 | Mori |
| 4,794,928 A | 1/1989 | Kletschka |
| 4,799,495 A | 1/1989 | Hawkins et al. |
| 4,820,270 A | 4/1989 | Hardcastle et al. |
| 4,832,055 A | 5/1989 | Palestrant |
| 4,858,810 A | 8/1989 | Intlekofer et al. |
| 4,869,259 A | 9/1989 | Elkins |
| 4,895,560 A | 1/1990 | Papantonakos |
| 4,921,478 A | 5/1990 | Solano et al. |
| 4,921,484 A | 5/1990 | Hillstead |
| 4,926,858 A | 5/1990 | Gifford, III et al. |
| 4,946,440 A | 8/1990 | Hall |
| 4,977,897 A | 12/1990 | Hurwitz |
| 5,011,488 A | 4/1991 | Ginsburg |
| 5,048,530 A | 9/1991 | Hurwitz |
| 5,059,166 A | 10/1991 | Fischell et al. |
| 5,078,685 A | 1/1992 | Colliver |
| 5,081,997 A | 1/1992 | Bosley, Jr. et al. |
| 5,092,839 A | 3/1992 | Kipperman |
| 5,100,425 A | 3/1992 | Fischell et al. |
| 5,102,415 A | 4/1992 | Guenther et al. |
| 5,108,420 A | 4/1992 | Marks |
| 5,112,347 A | 5/1992 | Taheri |
| 5,116,352 A | 5/1992 | Schnepp-Pesch et al. |
| 5,135,484 A | 8/1992 | Wright |
| 5,171,305 A | 12/1992 | Schickling et al. |
| 5,176,659 A | 1/1993 | Mancini |
| 5,183,463 A | 2/1993 | Debbas |
| 5,183,464 A | 2/1993 | Dubrul et al. |
| 5,192,290 A | 3/1993 | Hilal |
| 5,209,727 A | 5/1993 | Radisch, Jr. et al. |
| 5,213,569 A | 5/1993 | Davis |
| 5,221,269 A | 6/1993 | Miller et al. |
| 5,226,909 A | 7/1993 | Evans et al. |
| 5,250,060 A | 10/1993 | Carbo et al. |
| 5,275,611 A | 1/1994 | Behl |
| 5,312,360 A | 5/1994 | Behl |
| 5,328,471 A | 7/1994 | Slepian |
| 5,329,942 A | 7/1994 | Gunther et al. |
| 5,330,482 A | 7/1994 | Gibbs et al. |
| 5,330,484 A | 7/1994 | Guenther et al. |
| 5,334,211 A | 8/1994 | Shiber |
| 5,336,205 A | 8/1994 | Zenzen et al. |
| 5,342,306 A | 8/1994 | Don Michael |
| 5,370,660 A | 12/1994 | Weinstein et al. |
| 5,380,273 A | 1/1995 | Dubrul et al. |
| 5,380,284 A | 1/1995 | Don Michael |
| 5,382,259 A | 1/1995 | Phelps et al. |
| 5,383,466 A | 1/1995 | Partika |
| 5,383,897 A | 1/1995 | Wholey |
| 5,397,307 A | 3/1995 | Goodin |
| 5,410,093 A | 4/1995 | Dorai |
| 5,419,774 A | 5/1995 | Willard et al. |
| 5,423,799 A | 6/1995 | Shiu |
| 5,431,676 A | 7/1995 | Dubrul et al. |
| 5,437,631 A | 8/1995 | Janzen |
| 5,441,485 A | 8/1995 | Peters |
| 5,443,454 A | 8/1995 | Tanabe et al. |
| 5,454,790 A | 10/1995 | Dubrul |
| 5,456,667 A | 10/1995 | Ham et al. |
| 5,462,529 A | 10/1995 | Simpson et al. |
| 5,483,976 A | 1/1996 | Mclaughlin et al. |
| 5,490,521 A | 2/1996 | Davis et al. |
| 5,496,275 A | 3/1996 | Sirhan et al. |
| 5,497,782 A | 3/1996 | Fugoso |
| 5,498,236 A | 3/1996 | Dubrul et al. |
| 5,501,408 A | 3/1996 | Kang et al. |
| 5,518,498 A | 5/1996 | Lindenberg et al. |
| 5,527,282 A | 6/1996 | Segal |
| 5,540,658 A | 7/1996 | Evans et al. |
| 5,549,626 A | 8/1996 | Miller et al. |
| 5,556,408 A | 9/1996 | Farhat |
| 5,569,275 A | 10/1996 | Kotula et al. |
| 5,569,277 A | 10/1996 | Evans et al. |
| 5,571,135 A | 11/1996 | Fraser et al. |
| 5,591,204 A | 1/1997 | Janzen et al. |
| 5,606,979 A | 3/1997 | Hodgson |
| 5,611,345 A | 3/1997 | Hibbeln |
| 5,626,614 A | 5/1997 | Hart |
| 5,632,754 A | 5/1997 | Farley et al. |
| 5,643,282 A | 7/1997 | Kieturakis |
| 5,653,684 A | 8/1997 | Laptewicz et al. |
| 5,653,689 A | 8/1997 | Buelna et al. |
| 5,662,671 A | 9/1997 | Barbut et al. |
| 5,662,703 A | 9/1997 | Yurek et al. |
| 5,681,335 A | 10/1997 | Serra et al. |
| 5,683,411 A | 11/1997 | Kavteladze et al. |
| 5,683,451 A | 11/1997 | Lenker et al. |
| 5,695,501 A | 12/1997 | Carol et al. |
| 5,695,507 A | 12/1997 | Auth et al. |
| 5,709,697 A | 1/1998 | Ratcliff et al. |
| 5,709,704 A | 1/1998 | Nott et al. |
| 5,713,848 A | 2/1998 | Dubrul et al. |
| 5,730,733 A | 3/1998 | Mortier et al. |
| 5,733,294 A | 3/1998 | Forber et al. |
| 5,738,652 A | 4/1998 | Boyd et al. |
| 5,749,883 A | 5/1998 | Halpern |
| 5,766,135 A | 6/1998 | Terwilliger |
| 5,766,191 A | 6/1998 | Trerotola |
| 5,766,203 A | 6/1998 | Imran et al. |
| 5,769,795 A | 6/1998 | Terwilliger |
| 5,769,871 A | 6/1998 | Mers et al. |
| 5,779,672 A | 7/1998 | Dormandy, Jr. |
| 5,792,157 A | 8/1998 | Mische et al. |
| 5,795,308 A | 8/1998 | Russin |
| 5,795,322 A | 8/1998 | Boudewijn |
| 5,797,960 A | 8/1998 | Stevens et al. |
| 5,814,064 A | 9/1998 | Daniel et al. |
| 5,827,324 A | 10/1998 | Cassell et al. |
| 5,833,650 A | 11/1998 | Imran |
| 5,843,022 A | 12/1998 | Willard et al. |
| 5,846,251 A | 12/1998 | Hart |
| 5,851,210 A | 12/1998 | Torossian |
| 5,853,422 A | 12/1998 | Huebsch et al. |
| 5,868,708 A | 2/1999 | Hart et al. |
| 5,897,567 A | 4/1999 | Ressemann et al. |
| 5,904,698 A | 5/1999 | Thomas et al. |
| 5,908,435 A | 6/1999 | Samuels |
| 5,910,150 A | 6/1999 | Saadat |
| 5,916,235 A | 6/1999 | Guglielmi |
| 5,928,186 A | 7/1999 | Homsma et al. |

(56) References Cited

U.S. PATENT DOCUMENTS

| 5,928,260 | A | 7/1999 | Chin et al. |
| 5,935,139 | A | 8/1999 | Bates |
| 5,947,985 | A | 9/1999 | Imran |
| 5,947,995 | A | 9/1999 | Samuels |
| 5,954,737 | A | 9/1999 | Lee |
| 5,972,019 | A | 10/1999 | Engelson et al. |
| 5,997,503 | A | 12/1999 | Willis et al. |
| 6,001,118 | A | 12/1999 | Daniel et al. |
| 6,027,520 | A | 2/2000 | Tsugita et al. |
| 6,053,876 | A | 4/2000 | Fisher |
| 6,053,900 | A | 4/2000 | Brown et al. |
| 6,066,158 | A | 5/2000 | Engelson et al. |
| 6,086,605 | A | 7/2000 | Barbut et al. |
| 6,096,053 | A | 8/2000 | Bates |
| 6,156,005 | A | 12/2000 | Theron |
| 6,161,034 | A | 12/2000 | Burbank et al. |
| 6,179,860 | B1 | 1/2001 | Fulton, III et al. |
| 6,206,868 | B1 * | 3/2001 | Parodi .................. A61M 25/10 |
| | | | 604/509 |
| 6,217,600 | B1 | 4/2001 | Dimatteo |
| 6,221,006 | B1 | 4/2001 | Dubrul et al. |
| 6,221,086 | B1 | 4/2001 | Forber |
| 6,231,544 | B1 | 5/2001 | Tsugita et al. |
| 6,234,995 | B1 * | 5/2001 | Peacock, III .... A61B 17/12045 |
| | | | 604/99.04 |
| 6,238,412 | B1 | 5/2001 | Dubrul et al. |
| 6,258,115 | B1 | 7/2001 | Dubrul |
| 6,277,083 | B1 | 8/2001 | Eggers et al. |
| 6,280,414 | B1 | 8/2001 | Shah et al. |
| 6,287,271 | B1 | 9/2001 | Dubrul et al. |
| 6,356,782 | B1 | 3/2002 | Sirimanne et al. |
| 6,361,545 | B1 | 3/2002 | Macoviak et al. |
| 6,375,634 | B1 | 4/2002 | Carroll |
| 6,413,235 | B1 | 7/2002 | Parodi |
| 6,423,032 | B2 | 7/2002 | Parodi et al. |
| 6,443,971 | B1 | 9/2002 | Boylan et al. |
| 6,450,989 | B2 | 9/2002 | Dubrul et al. |
| 6,485,501 | B1 | 11/2002 | Green |
| 6,524,301 | B1 | 2/2003 | Wilson et al. |
| 6,530,923 | B1 | 3/2003 | Dubrul et al. |
| 6,540,768 | B1 | 4/2003 | Diaz et al. |
| 6,544,278 | B1 | 4/2003 | Vrba et al. |
| 6,602,204 | B2 | 8/2003 | Dubrul et al. |
| 6,605,102 | B1 | 8/2003 | Mazzocchi et al. |
| 6,626,886 | B1 | 9/2003 | Barbut |
| 6,635,068 | B1 | 10/2003 | Dubrul et al. |
| 6,656,202 | B2 | 12/2003 | Papp et al. |
| 6,660,014 | B2 | 12/2003 | Demarais et al. |
| 6,695,858 | B1 | 2/2004 | Dubrul et al. |
| 6,699,260 | B2 | 3/2004 | Dubrul et al. |
| 6,740,094 | B2 | 5/2004 | Maitland et al. |
| 6,852,097 | B1 | 2/2005 | Fulton, III |
| 6,929,652 | B1 | 8/2005 | Andrews et al. |
| 6,945,977 | B2 | 9/2005 | Demarais et al. |
| 6,994,677 | B2 | 2/2006 | Buehlmann et al. |
| 7,201,770 | B2 | 4/2007 | Johnson et al. |
| 7,220,269 | B1 | 5/2007 | Ansel et al. |
| 7,232,432 | B2 | 6/2007 | Fulton et al. |
| 7,232,453 | B2 | 6/2007 | Shimon |
| 7,241,257 | B1 | 7/2007 | Ainsworth et al. |
| 7,374,561 | B2 | 5/2008 | Barbut |
| 7,422,579 | B2 | 9/2008 | Wahr et al. |
| 7,534,251 | B2 | 5/2009 | Wasdyke |
| 7,569,071 | B2 | 8/2009 | Haverkost et al. |
| 7,645,296 | B2 | 1/2010 | Theron et al. |
| 7,670,368 | B2 | 3/2010 | Hill et al. |
| 7,686,825 | B2 | 3/2010 | Hauser et al. |
| 7,780,722 | B2 | 8/2010 | Thielen et al. |
| 7,803,171 | B1 | 9/2010 | Uflacker |
| 7,867,274 | B2 | 1/2011 | Hill et al. |
| 7,951,189 | B2 | 5/2011 | Haverkost et al. |
| 7,959,603 | B2 | 6/2011 | Wahr et al. |
| 8,366,737 | B2 | 2/2013 | Hancock et al. |
| 8,657,849 | B2 | 2/2014 | Parker |
| 8,663,273 | B2 | 3/2014 | Khairkhahan et al. |
| 8,715,317 | B1 | 5/2014 | Janardhan et al. |
| 8,740,961 | B2 | 6/2014 | Fulton, III |
| 8,771,289 | B2 | 7/2014 | Mohiuddin et al. |
| 8,777,976 | B2 | 7/2014 | Brady et al. |
| 8,784,441 | B2 | 7/2014 | Rosenbluth et al. |
| 8,795,305 | B2 | 8/2014 | Martin et al. |
| 8,900,257 | B2 | 12/2014 | Straub et al. |
| 9,114,031 | B2 | 8/2015 | Fulton, III |
| 9,126,016 | B2 | 9/2015 | Fulton et al. |
| 9,186,487 | B2 | 11/2015 | Dubrul et al. |
| 9,211,396 | B2 | 12/2015 | Aboytes |
| 9,498,604 | B2 | 11/2016 | Dubrul et al. |
| 9,561,094 | B2 | 2/2017 | Fulton |
| 10,335,577 | B2 | 7/2019 | Fulton, III |
| 11,266,414 | B2 | 3/2022 | Fulton, III |
| 11,623,070 | B2 | 4/2023 | Fulton, III |
| 2002/0007130 | A1 | 1/2002 | Burbank et al. |
| 2002/0016555 | A1 | 2/2002 | Ritchart et al. |
| 2002/0019640 | A1 | 2/2002 | McGuckin |
| 2002/0022859 | A1 | 2/2002 | Hogendijk |
| 2002/0026201 | A1 | 2/2002 | Foerster et al. |
| 2002/0045916 | A1 | 4/2002 | Gray et al. |
| 2002/0095169 | A1 | 7/2002 | Maitland et al. |
| 2002/0161394 | A1 | 10/2002 | Macoviak et al. |
| 2002/0165574 | A1 | 11/2002 | Ressemann et al. |
| 2002/0165598 | A1 | 11/2002 | Wahr et al. |
| 2003/0023204 | A1 | 1/2003 | Vo et al. |
| 2003/0083608 | A1 | 5/2003 | Evans et al. |
| 2003/0109896 | A1 | 6/2003 | Dubrul et al. |
| 2003/0114879 | A1 | 6/2003 | Euteneuer et al. |
| 2003/0163158 | A1 | 8/2003 | White |
| 2003/0176884 | A1 | 9/2003 | Berrada et al. |
| 2004/0015150 | A1 | 1/2004 | Zadno-Azizi |
| 2004/0044391 | A1 | 3/2004 | Porter |
| 2004/0153117 | A1 | 8/2004 | Clubb et al. |
| 2004/0181237 | A1 | 9/2004 | Forde et al. |
| 2004/0199202 | A1 | 10/2004 | Dubrul et al. |
| 2004/0236369 | A1 | 11/2004 | Dubrul |
| 2004/0260332 | A1 | 12/2004 | Dubrul et al. |
| 2004/0260333 | A1 | 12/2004 | Dubrul et al. |
| 2005/0018757 | A1 | 1/2005 | Zaccheo et al. |
| 2005/0038447 | A1 | 2/2005 | Huffmaster |
| 2005/0059993 | A1 | 3/2005 | Ramzipoor et al. |
| 2005/0165366 | A1 | 7/2005 | Brustad et al. |
| 2005/0187570 | A1 | 8/2005 | Nguyen et al. |
| 2005/0277976 | A1 | 12/2005 | Galdonik et al. |
| 2006/0047286 | A1 | 3/2006 | West |
| 2006/0058836 | A1 | 3/2006 | Bose et al. |
| 2006/0085065 | A1 | 4/2006 | Krause et al. |
| 2006/0200074 | A1 | 9/2006 | Zadno-Azizi |
| 2006/0253145 | A1 | 11/2006 | Lucas |
| 2007/0123932 | A1 | 5/2007 | Gray et al. |
| 2007/0126161 | A1 | 6/2007 | Gray et al. |
| 2007/0142858 | A1 | 6/2007 | Bates |
| 2007/0233175 | A1 | 10/2007 | Zaver et al. |
| 2008/0058794 | A1 | 3/2008 | Macadam et al. |
| 2008/0058800 | A1 | 3/2008 | Collins et al. |
| 2008/0119888 | A1 | 5/2008 | Huffmaster |
| 2009/0264976 | A1 | 10/2009 | Nagasrinivasa |
| 2010/0030256 | A1 | 2/2010 | Dubrul et al. |
| 2010/0114113 | A1 | 5/2010 | Dubrul et al. |
| 2010/0228281 | A1 | 9/2010 | Gilson et al. |
| 2011/0009943 | A1 | 1/2011 | Paul et al. |
| 2011/0213403 | A1 | 9/2011 | Aboytes |
| 2011/0270178 | A1 | 11/2011 | Fiorella et al. |
| 2011/0270298 | A1 | 11/2011 | Abrams |
| 2011/0288529 | A1 * | 11/2011 | Fulton .................. A61M 25/04 |
| | | | 604/510 |
| 2011/0288572 | A1 | 11/2011 | Martin |
| 2012/0059309 | A1 | 3/2012 | Di Palma et al. |
| 2012/0083824 | A1 | 4/2012 | Berrada et al. |
| 2012/0116351 | A1 | 5/2012 | Chomas et al. |
| 2012/0316597 | A1 | 12/2012 | Fitz et al. |
| 2013/0030461 | A1 | 1/2013 | Marks et al. |
| 2013/0110152 | A1 | 5/2013 | Dubrul et al. |
| 2013/0144326 | A1 | 6/2013 | Brady et al. |
| 2013/0310803 | A1 | 11/2013 | Morsi |
| 2013/0317534 | A1 | 11/2013 | Zhou et al. |
| 2013/0345739 | A1 | 12/2013 | Brady et al. |

(56)  References Cited

U.S. PATENT DOCUMENTS

| | | |
|---|---|---|
| 2014/0005712 A1 | 1/2014 | Martin |
| 2014/0039598 A1 | 2/2014 | Sampognaro et al. |
| 2014/0188156 A1 | 7/2014 | Tekulve et al. |
| 2014/0236219 A1 | 8/2014 | Dubrul et al. |
| 2014/0343602 A1 | 11/2014 | Cox et al. |
| 2015/0066075 A1 | 3/2015 | Russell et al. |
| 2015/0112376 A1 | 4/2015 | Molaei et al. |
| 2015/0190141 A1 | 7/2015 | Cragg et al. |
| 2015/0257775 A1 | 9/2015 | Gilvarry et al. |
| 2015/0343182 A1 | 12/2015 | Vazales et al. |
| 2015/0351770 A1 | 12/2015 | Fulton, III |
| 2015/0351775 A1* | 12/2015 | Fulton, III ....... A61B 17/12172 |
| | | 606/191 |
| 2016/0022293 A1 | 1/2016 | Dubrul et al. |
| 2016/0045202 A1 | 2/2016 | Ferry et al. |
| 2016/0058458 A1 | 3/2016 | Hansen et al. |
| 2016/0074024 A1 | 3/2016 | Scheule |
| 2019/0117244 A1 | 4/2019 | Wallace et al. |
| 2020/0345376 A1 | 11/2020 | Fulton, III |
| 2020/0368499 A1 | 11/2020 | Fulton, III |
| 2024/0050703 A1 | 2/2024 | Fulton, III |

FOREIGN PATENT DOCUMENTS

| | | | |
|---|---|---|---|
| EP | 1179321 | A2 | 2/2002 |
| EP | 1549229 | A2 | 7/2005 |
| EP | 1617893 | A1 | 1/2006 |
| EP | 1761298 | A2 | 3/2007 |
| EP | 1799128 | A2 | 6/2007 |
| EP | 1981413 | A2 | 10/2008 |
| EP | 1399089 | B1 | 12/2008 |
| EP | 1629784 | B1 | 1/2010 |
| EP | 2057967 | B1 | 1/2013 |
| EP | 2596828 | A1 | 5/2013 |
| EP | 2683309 | A2 | 1/2014 |
| EP | 2707077 | A1 | 3/2014 |
| EP | 2744423 | A1 | 6/2014 |
| EP | 2801325 | A1 | 11/2014 |
| EP | 2854924 | A1 | 4/2015 |
| EP | 2879625 | A1 | 6/2015 |
| EP | 2908901 | A2 | 8/2015 |
| EP | 2341845 | B1 | 1/2016 |
| EP | 2979649 | A1 | 2/2016 |
| FR | 2312264 | A1 | 12/1976 |
| FR | 2380018 | A1 | 9/1978 |
| GB | 2020557 | A | 11/1979 |
| JP | H08308932 | A | 11/1996 |
| JP | H10328306 | A | 12/1998 |
| JP | 2006519657 | A | 8/2006 |
| JP | 4731471 | B2 | 7/2011 |
| JP | 5805736 | B2 | 11/2015 |
| WO | WO-8001343 | A1 | 6/1980 |
| WO | WO-8001353 | A1 | 7/1980 |
| WO | WO-9424946 | A1 | 11/1994 |
| WO | WO-9509024 | A1 | 4/1995 |
| WO | WO-9516487 | A1 | 6/1995 |
| WO | WO-9601591 | A1 | 1/1996 |
| WO | WO-9923952 | A1 | 5/1999 |
| WO | WO-9944506 | A1 | 9/1999 |
| WO | WO-9944510 | A1 | 9/1999 |
| WO | WO-9944542 | A2 | 9/1999 |
| WO | WO-9944542 | A3 | 11/1999 |
| WO | WO-0012009 | A2 | 3/2000 |
| WO | WO-0012010 | A1 | 3/2000 |
| WO | WO-0149208 | A1 | 7/2001 |
| WO | WO-0197697 | A1 | 12/2001 |
| WO | WO-02055146 | A1 | 7/2002 |
| WO | WO-02087677 | A2 | 11/2002 |
| WO | WO-03002028 | A2 | 1/2003 |
| WO | WO-2004019791 | A2 | 3/2004 |
| WO | WO-2004093966 | A1 | 11/2004 |
| WO | WO-2005079678 | A1 | 9/2005 |
| WO | WO-2005118050 | A2 | 12/2005 |
| WO | WO-2006031410 | A2 | 3/2006 |
| WO | WO-2007089897 | A2 | 8/2007 |
| WO | WO-2008010197 | A2 | 1/2008 |
| WO | WO-2008010197 | A3 | 4/2008 |
| WO | WO-2008124567 | A1 | 10/2008 |
| WO | WO-2010010545 | A1 | 1/2010 |
| WO | WO-2012009675 | A2 | 1/2012 |
| WO | WO-2012011518 | A1 | 1/2012 |
| WO | WO-2012120490 | A2 | 9/2012 |
| WO | WO-2012155093 | A1 | 11/2012 |
| WO | WO-2013028579 | A1 | 2/2013 |
| WO | WO-2013177383 | A1 | 11/2013 |
| WO | WO-2014022409 | A1 | 2/2014 |
| WO | WO-2014062645 | A2 | 4/2014 |
| WO | WO-2014164535 | A1 | 10/2014 |
| WO | WO-2014180702 | A1 | 11/2014 |
| WO | WO-2015057796 | A1 | 4/2015 |
| WO | WO-2015187196 | A1 | 12/2015 |
| WO | WO-2016040923 | A2 | 3/2016 |
| WO | WO-2016064077 | A1 | 4/2016 |
| WO | WO-2017161204 | A1 | 9/2017 |
| WO | WO-2018200233 | A1 | 11/2018 |
| WO | WO-2022251678 | A1 | 12/2022 |

OTHER PUBLICATIONS

EP22812291.7 Partial European Search Report dated Feb. 6, 2025.
PCT/US2022/031404 International Search Report and Written Opinion dated Oct. 12, 2022.
PCT/US2022/031404 Invitation to Pay Additional Fees dated Aug. 3, 2022.
Schmitz-Rode, et al. New device for percutaneous fragmentation of pulmonary emboli. Radiology. Jul. 1991;180(1):135-7.
Sharafuddin, et al. Current status of percutaneous mechanical thrombectomy. Part I. General principles. J Vasc Interv Radiol. Nov.-Dec. 1997;8(6):911-21.
"Velocimed, Proxis, Embolic Protection System", http://www.velocimed.com/proxis.htm (visited Feb. 5, 2004), (2003). (4 pages).

* cited by examiner

FUNNEL CATHETER AND NOVEL METHODS OF UTILIZATION

CROSS-REFERENCE

This application is a continuation of International Application No. PCT/US22/31404, filed May 27, 2022, which claims the benefit of U.S. Provisional Patent Application No. 63/309,028, filed Feb. 11, 2022, and U.S. Provisional Patent Application No. 63/193,614, filed May 27, 2021, each of which is incorporated herein by reference in its entirety.

BACKGROUND OF THE INVENTION

Catheter technology is widely utilized to diagnose many abnormalities, to treat vascular disease, to perform vascular interventions, to deliver devices to occlude vessels, and to focally deliver agents to tissues, among other uses. The catheter technology best employed for a given application can vary depending on the surgical procedure and the nature and extent of the injury. For a general background on catheter technology and some of the tools and apparatus used involving catheters, see U.S. Pat. No. 5,910,150 issued to Saadat on Jun. 8, 1999, the entire disclosure of which is incorporated herein by reference in its entirety. In addition, further background on catheter technology and some of the tools and apparatus used involving catheters is found in U.S. Pat. No. 7,241,257 issued to Ainsworth et al. on Jul. 10, 2007, the entire disclosure of which is incorporated herein by reference in its entirety.

Some attempts have been made to develop catheters useful and adaptable for multiple applications, see U.S. Pat. No. 5,632,754 issued to Farley et al. on May 27, 1997, the entire disclosure of which is incorporated herein by reference in its entirety.

SUMMARY

The present disclosure generally relates to devices, systems, and methods useful in the removal of thrombus, embolus, or debris from a blood vessel and other intravascular interventional actions, including proximal embolic protection when treating a vascular lesion or condition. In various aspects, a device operable for removing material from a blood vessel comprises: an outer catheter shaft; an inner catheter shaft disposed at least partially within the outer shaft; and an expandable element having a first end coupled to a distal end of the inner catheter shaft and a second end coupled to a distal end of the outer catheter shaft such that translation of the inner catheter shaft relative to the outer catheter shaft causes the expandable element to transition between an expanded configuration and a collapsed configuration, the expanded element having a funnel shape in the expanded configuration and a cylindrical tubular shape in the collapsed configuration, wherein an inner surface of the funnel shape is contiguous with an inner surface of the inner catheter shaft. In various aspects, a device operable for removing material from a blood vessel comprises: an outer catheter shaft; an inner catheter shaft disposed at least partially within the outer shaft; and an expandable element having a first end coupled to a distal end of the inner catheter shaft and a second end coupled to a distal end of the outer catheter shaft such that translation of the outer catheter shaft relative to the inner catheter shaft causes the expandable element to transition between an expanded configuration and a collapsed configuration, the expanded element having a funnel shape in the expanded configuration and a cylindrical tubular shape in the collapsed configuration, wherein an inner surface of the funnel shape is contiguous with an inner surface of the inner catheter shaft. In some cases, a wall of the distal end of the inner catheter shaft comprises a plurality of apertures therethrough. In some cases, a non-porous portion of the expandable element comprises one or more apertures therethrough. In some cases, translation of the inner catheter shaft in a distal direction relative to the outer catheter shaft exposes the plurality of apertures and causes the expandable element to assume the expanded configuration. In some cases, one or more apertures of the plurality of apertures is sized to allow blood flow through the one or more apertures. In some cases, the first end of the expandable element comprises a non-porous segment and the second end of the expandable element comprises a porous segment. In some cases, the non-porous segment of the expandable element comprises a plurality of apertures sized and positioned to allow blood to therethrough when the expandable element is in the expanded configuration. In some cases, the device further comprises a vacuum coupled to a proximal end of the inner shaft and operable to apply negative pressure within a lumen of the inner catheter shaft. In some cases, the distal end of the outer catheter shaft comprises a transition segment. In some cases, the transition segment contacts a wall of a distal end of the inner catheter shaft. In some cases, the transition segment bridges a space between an outer surface of the outer catheter shaft and a surface of the inner catheter shaft. In some cases, the device further comprises one or more dilators. In some cases, the one or more dilator is disposed coaxially with one or more of the inner catheter shaft, the outer catheter shaft, or the expandable element. In some cases, at least one dilator of the one or more dilators has a stiffness sufficient for guiding the device to an intravascular target site during a percutaneous entry procedure. In some cases, a distal end of the one or more dilators comprises a tapered tip. In some cases, a distal tip of one or more dilators comprises an elastomeric material. In some cases, translation of the inner catheter shaft relative to the outer catheter shaft causes the expandable element to transition between an expanded configuration in which the expandable element assumes a cylindrical shape disposed at least partially between an outer surface of the inner catheter shaft and an inner surface of the outer catheter shaft and a collapsed configuration in which the expandable element assumes a funnel shape. In some cases, transition of the expandable element to the expanded configuration in the blood vessel causes the expandable element to contact the vessel wall and anchor a distal tip of the device in the blood vessel while preserving forward blood flow. In some cases, further translation of the inner catheter shaft relative to the outer catheter shaft causes the expandable member to occlude blood flow in the blood vessel while contacting the vessel wall and anchoring the distal tip of the device. In some cases, the inner catheter shaft is more flexible than the outer catheter shaft and the inner catheter shaft is adjacent to the expandable element when the expandable element is in the collapsed configuration. In some cases, the outer catheter shaft is more flexible than the inner catheter shaft and the outer catheter shaft is adjacent to the expandable element when the expandable element is in the collapsed configuration. In some cases, the device can be used in a method of enhancing forward navigation of the device, wherein the expandable element of the device is partially deployed to capture the forward flowing blood to urge the device forward. In some cases, the device can be used in a method comprising: occluding the blood vessel at a location proximal to a target site by expanding an expandable element of the device, performing an intervention at the target site using an interventional tool, aspirating a material liberated from the target site as a result of the intervention, removing the interventional tool, collapsing the expandable element, and removing the device from the blood vessel. In some cases, the material comprises debris or incipient emboli and the material comprises particulate matter and a drug from the interventional tool. In some cases, the interventional tool is a drug coated balloon or a drug eluting balloon. In various aspects, a method for removing material from a blood vessel comprises, expanding an expandable member of the device from a collapsed configuration to an expanded configuration within the blood vessel, wherein a first end of the expandable member is coupled to an inner catheter shaft of the device and a second end of the expandable member is coupled to a distal end of an outer catheter shaft of the device and wherein the expanded configuration has a funnel shape; applying negative pressure to a proximal end of a lumen of the inner catheter shaft; and translating the inner catheter shaft distally relative to the outer catheter shaft to create protective flow arrest proximal to the material and utilizing at least one maneuver to cause micro-movements of the material, the at least one maneuver comprising one or more of: 1) varying the suction forces applied to the proximal end of the inner shaft, 2) deploying and collapsing the expandable element a plurality of times, 3) providing sound or pressure waves to the material through the inner shaft of the device, 4) inducing vibrations in the material using the device, and 5) administering fluids comprising one or more lytic agents to the material. In some cases, the at least one maneuver is sufficient to overcome one or more of (i) an impaction force of the material, (ii) friction between the material and the vessel wall, (iii) adhesive forces between the material and the vessel wall, or (iv) an internal consistency of the clot.

In various aspects, a method for removing material from a blood vessel comprises, expanding an expandable element of an intravascular device from a collapsed configuration to an expanded configuration within the blood vessel, wherein a first end of the expandable element is coupled to an inner catheter shaft of the device and a second end of the expandable element is coupled to a distal end of an outer catheter shaft of the device and wherein the expanded configuration has a funnel shape; applying negative pressure to a proximal end of a lumen of the inner catheter shaft; and translating the inner catheter shaft distally relative to the outer catheter shaft to expose one or more apertures in a wall of the distal end of the inner catheter shaft to allow fluidic communication between the lumen of the inner catheter shaft and blood of the blood vessel located outside of the wall of the inner catheter shaft. In various aspects, a method for removing material from a blood vessel comprises, expanding an expandable element of an intravascular device from a collapsed configuration to an expanded configuration within the blood vessel, wherein a first end of the expandable element is coupled to an inner catheter shaft of the device and a second end of the expandable element is coupled to a distal end of an outer catheter shaft of the device and wherein the expanded configuration has a funnel shape; applying negative pressure to a proximal end of a lumen of the inner catheter shaft; and translating the outer catheter shaft proximally relative to the inner catheter shaft to expose one or more apertures in a wall of the distal end of the inner catheter shaft to allow fluidic communication between the lumen of the inner catheter shaft and blood of the blood vessel located outside of the wall of the inner catheter shaft. In various aspects, a method for removing material from a blood vessel, comprises, expanding an expandable element of an intravascular device from a collapsed configuration to an expanded configuration within the blood vessel, wherein a first end of the expandable element is coupled to an inner catheter shaft of the device and a second end of the expandable element is coupled to a distal end of an outer catheter shaft of the device and wherein the expanded configuration has a funnel shape; applying negative pressure to a proximal end of a lumen of the inner catheter shaft; and translating the inner catheter shaft distally relative to the outer catheter shaft to expose one or more apertures in a wall of the expandable element to allow fluidic communication between the lumen of the inner catheter shaft and blood of the blood vessel located outside of the wall of the inner catheter shaft. In various aspects, a method for removing material from a blood vessel, comprises, expanding an expandable element of an intravascular device from a collapsed configuration to an expanded configuration within the blood vessel, wherein a first end of the expandable element is coupled to an inner catheter shaft of the device and a second end of the expandable element is coupled to a distal end of an outer catheter shaft of the device and wherein the expanded configuration has a funnel shape; applying negative pressure to a proximal end of a lumen of the inner catheter shaft; and translating the outer catheter shaft proximally relative to the inner catheter shaft to expose one or more apertures in a wall of the expandable element to allow fluidic communication between the lumen of the inner catheter shaft and blood of the blood vessel located outside of the wall of the inner catheter shaft. In some cases, the method further comprises creating inward flow of blood through the one or more apertures to decrease the friction between the material and an inner surface of the inner catheter shaft. In some cases, the method further comprises occluding the blood vessel by expanding the expandable element from the collapsed configuration to the expanded configuration. In some cases, the negative pressure is applied and suddenly removed to cause recoil of the material within the blood vessel. In some cases, the negative pressure is applied and removed within 0.1 second or less. In some cases, the recoil is sufficient to overcome one or more of (i) an impaction force of the material, (ii) friction between the material and the vessel wall, (iii) adhesive forces between the material and the vessel wall, or (iv) an internal consistency of the clot which precludes aspiration into a smaller channel. In some cases, the method further comprises applying negative pressure to the proximal end of the lumen of the inner catheter shaft until all of the material is removed from the blood vessel. In some cases, negative pressure is applied and suddenly removed two or more times in succession. In some cases, the method further comprises providing traction on the distal aspect of the clot using a clot retractor while applying the negative pressure to the proximal end of the lumen of the inner catheter shaft. In some cases, the method further comprises withdrawing the inner catheter shaft inside of the outer catheter shaft after application of the negative pressure, wherein the inner catheter shaft is disposed at least partially within and coaxial in relationship to the outer catheter shaft. In various aspects, a method of preventing fragmentation and distal embolization of a thrombus during thrombus removal from a target site of a blood vessel comprises: contacting the thrombus with a lytic agent; introducing a protective flow arrest device into the blood vessel in close proximity to the target site; occluding the blood vessel to blood flow with the protective flow arrest device by expanding the expandable element of the protective flow arrest device; aspirating the partially dissolved thrombus while occluding the blood vessel; aspirating the thrombus through the protective flow arrest device; transitioning the expandable element of the protective flow arrest expandable element to a collapsed configuration; and removing the protective flow arrest device from the body. In some cases, occluding the flow with the protective flow arrest device prevents subsequent disturbance of the thrombus from antegrade blood flow. In some cases, the method further comprises discontinuing aspiration after transitioning the expandable element to a collapsed configuration to allow retrograde blood in the vicinity of the target site to remove residual debris or thrombus fragments the target site and its vicinity.

INCORPORATION BY REFERENCE

All publications, patents, and patent applications mentioned in this specification are herein incorporated by reference to the same extent as if each individual publication, patent, or patent application was specifically and individually indicated to be incorporated by reference. In particular, U.S. Pat. Nos. 9,126,016, 10,335,577, 6,238,412, 9,186,487, 9,498,604, 8,740,961, 9,114,031, 9,561,094, 6,258,115, 6,221,006, 6,695,858, 11,266,414, EP 1030603, EP 1617893, JP 5805736, and JP 4731471 are incorporated herein by reference in their entireties for all purposes, including for disclosures of catheter-based systems, devices, and methods and components and features of said systems, devices, and methods described therein, which may be useful in various embodiments of the systems, devices, and methods described herein.

BRIEF DESCRIPTION OF THE DRAWINGS

The novel features of the inventions are set forth with particularity in the appended claims. A better understanding of the features and advantages of the present inventions will be obtained by reference to the following detailed description that sets forth illustrative embodiments, in which the principles of the inventions are utilized, and the accompanying drawings of which:

DETAILED DESCRIPTION

Figure 1:
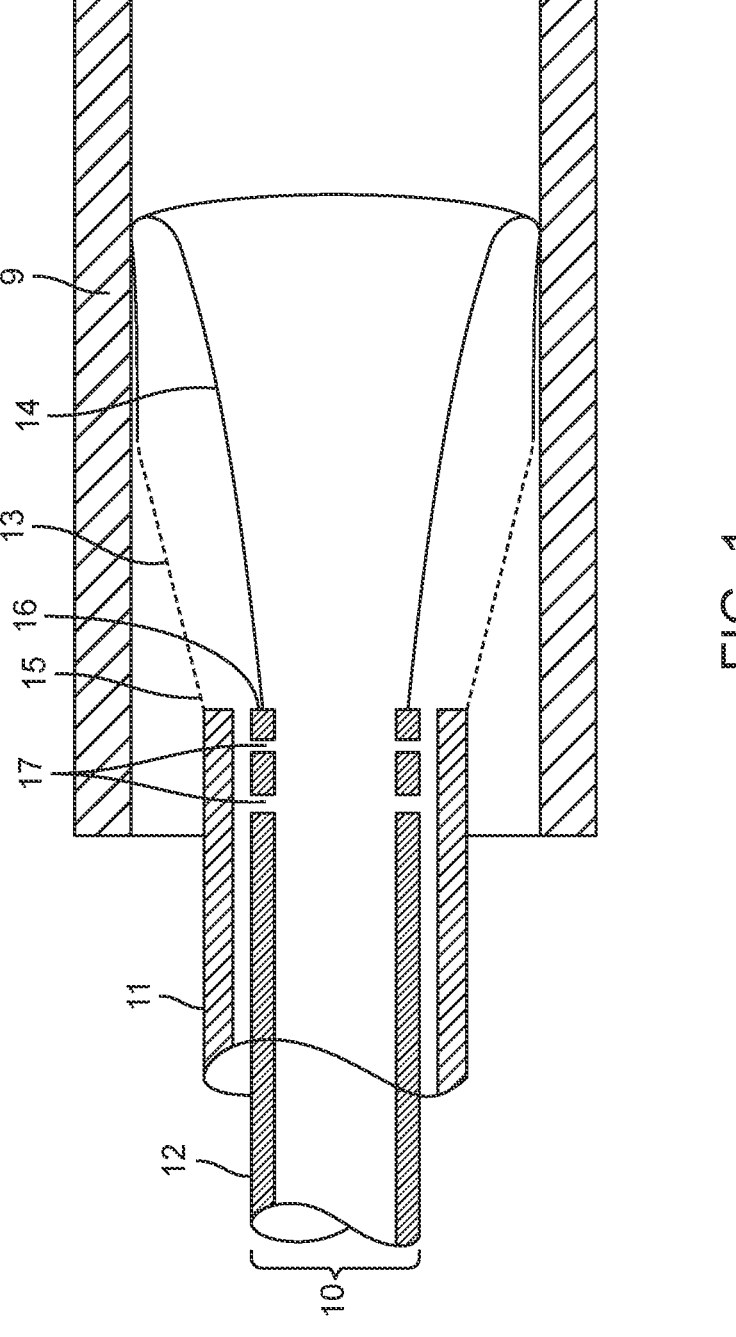
FIG. 1 shows a schematic of a device comprising an inner catheter shaft comprising apertures, an outer catheter shaft, and an expandable element, in accordance with embodiments.

Described herein are systems, devices, and methods for removing material, such as thrombus material or debris, from a vessel. As described herein, a catheter-based system comprising an expandable element configured to expand into a funnel shape can increase the efficiency of removing materials (e.g., all or portion of a blood clot or debris) present in a blood vessel and can improve the ease with which such tasks are completed, for example, as compared to conventional straw-like catheters. For example, the larger diameter of the inlet or mouth of the expandable element can allow the catheter-based devices and systems comprising an expandable element, as described herein, to occlude blood flow more completely than other catheter-based devices and systems, allowing for better aspiration and more complete clot or debris transfer into the catheter shaft.

Utilizing a catheter-based device or system comprising an expandable element (e.g., which can assume a funnel shape in an expanded configuration) as described herein may increase the cross-sectional surface area of the inlet or mouth of the catheter by a factor of 3-6 depending on the size of the shaft of the catheter and other considerations. Furthermore, since this cross sectional area is directly proportional to suction force, this also is a huge advantage in removing debris, clots, or thrombus from an artery, vein, or graft of the body, as the suction force (e.g., which may be applied to the debris, clot, or thrombus by applying a negative pressure to a lumen of an inner catheter shaft of the device) will also increase by a factor of 3 to 6 fold. Moreover, a catheter-based device or system comprising an expandable element with a diameter greater than the inner diameter of the catheter can be advantageous in that the clot being retracted will not be sheared off upon ingestion (e.g., translation of a material into the inner catheter shaft lumen) as it will with a standard conventional catheter.

In contrast, the tip of conventional catheters, being significantly smaller than the clot, tends to "plug" or "core" the clot when attempting to aspirate the clot. This action can inhibit the ingress of clot into the catheter shaft lumen as the clot can become imbedded by the catheter tip of standard, conventional catheters. Catheter-based devices and systems described herein can circumvent these problems, as the large and tapered, conical inlet provided by the expandable element (e.g., in its expanded configuration) presents less resistance to the ingress of clot into the catheter shaft.

Moreover, catheter-based devices and systems described herein that comprise an expandable element may also be configured to occlude blood flow, which can provide a static environment to perform other procedures, provide a more directed aspiration force downstream, and/or provide embolic protection before, during, and after the intended intervention amongst other advantages, including the ability to anchor and center the tip of the catheter to provide support for other devices.

In some cases, catheter-based devices and systems comprising an expandable element described herein can be useful in procedures such as thrombectomy, embolectomy, and embolic protection.

In some cases, an expandable element can completely occlude a vessel just upstream from an occluding thrombus which can allow all the aspiration force to be directed downstream towards the clot while not preferentially aspirating upstream blood as is the case of conventional catheters. This can be a distinct advantage in some situations as the aspiration efficiency can be dramatically improved. This occlusion may create a vacuum distal to the funnel and proximal to the clot (e.g., as a result of a negative pressure being applied to a lumen of an inner catheter shaft of a catheter-based device or system comprising an expandable element described herein) which can be very advantageous for aspirating the clot into the large mouth of the (e.g., funnel shaped) expandable element and into the catheter shaft.

In some cases, the thrombus can be compressed as it migrates from the large mouth of the funnel to the smaller catheter shaft, which can cause friction to develop between the clot or debris and the inner portion of the funnel of the expandable element (especially towards the base of the funnel) and/or the inner aspect of the catheter shaft as the clot or debris is compressed against their surfaces. This may be partly due to fluid being displaced from the clot when it is compressed and partly due to the inherent resistance of the clot from being compressed as well as some adhesive or adherent properties of the clot. In traditional catheter systems, the thrombus or clot may become lodged or stuck within the catheter shaft as a result and may interrupt the process of removal of the clot. This may require removal of the entire device, flushing the clot out of the catheter lumen, and re-inserting the catheter, which can be time consuming and can add additional risk to the procedure. In some cases, a device may be inserted through the catheter shaft and beyond the clot which then provide traction on the clot to pull it towards and out the hub of the catheter, thereby clearing the catheter shaft of the obstruction without removal and re-inserting the catheter, albeit with an increased potential for unintended fragmentation and/or distal embolization of the clot.

As described herein, a less complicated and more effective method of clearing obstructions from a vessel can comprise reducing the friction that can result from compression of a clot into a catheter shaft having a smaller inner diameter than the diameter of the clot, for instance by introducing fluid flow between the clot and the inner catheter shaft wall.

In some cases, a thrombus must change shape upon being aspirated from a more or less cylindrical structure of several millimeters in diameter and several centimeters in length in the vessel to a much smaller diameter within the catheter shaft. In some cases, blood vessel clots can be older, more organized and comprised of fibrin components which can cause clot compression and deformation (e.g., during clot retrieval) to be more difficult (e.g., as compared to newer clots, which may be comprises largely of red blood cells and may be soft and deformable).

Figures 3A, 3B:
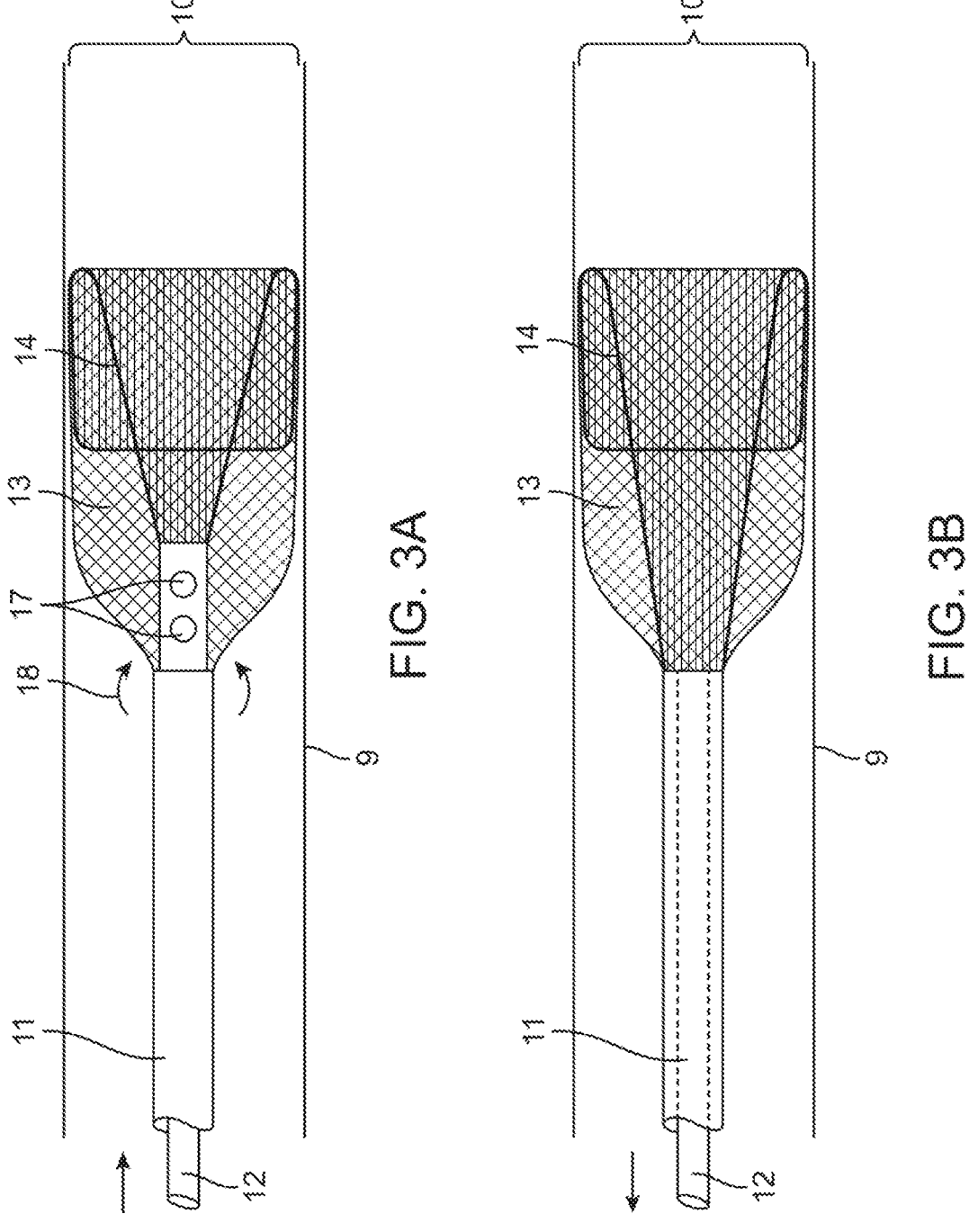
FIG. 3A shows a schematic of use of a device comprising an inner catheter shaft comprising apertures, an outer catheter shaft, and an expandable element, in accordance with embodiments.
FIG. 3B shows a schematic of use of a device comprising an inner catheter shaft comprising apertures, an outer catheter shaft, and an expandable element, in accordance with embodiments.

For example, a mixed age subacute and chronic clot in the iliac veins, which may be 16 mm in diameter with fibrin components and may be quite firm, may be difficult to aspirate into the inner diameter of a 12 Fr. catheter with an ID of 3-4 mm. Because of varying consistencies, sizes, ages, and relative difficulties in aspirating different thrombus from different vessels, catheter-based devices and systems described herein, which can be used to decrease friction between a clot and a wall of an inner catheter shaft and/or further fragment the thrombus for easier aspiration and transit through the catheter lumen, can overcome many limitations of existing catheters, such as existing thrombectomy catheters A catheter-based device can comprise one or more catheters (e.g., wherein a catheter comprises a catheter shaft having a distal end introduced into a lumen of a body cavity 9, such as a blood vessel, for example, as shown in FIG. 1). In some cases, a device or system described herein can comprise an inner catheter shaft 12 and an outer catheter shaft 11 or sheath. In many cases, a device or system described herein can comprise an expandable element (45, 61, 143), for example, to aid in the collection of material 40 (e.g., all or a portion of blood clot 40 or other obstruction) present in the lumen of the body cavity 9. In some cases, a first end 16 of the expandable element can be coupled to a distal end of an inner catheter shaft 12. In some cases, a second end 15 of the expandable element can be coupled to a distal end of an outer catheter shaft 11. In some cases, the expandable element can have an expanded configuration and a collapsed configuration. In some cases, the expandable element can be disposed entirely, substantially, or partially outside of an outer catheter shaft 11 and/or an inner catheter shaft 12 of the device or system when the expandable element is in an expanded configuration (e.g., as shown in FIG. 3A). In some cases, the expandable element can have a larger diameter at one end than at another end or ends (e.g., at a first end 16 coupled to an inner catheter shaft 12 and/or a second end 15 coupled to outer catheter 11), for example, when in the expanded configuration. In some cases, an expandable element can have a funnel or conical shape when

Figure 6A:
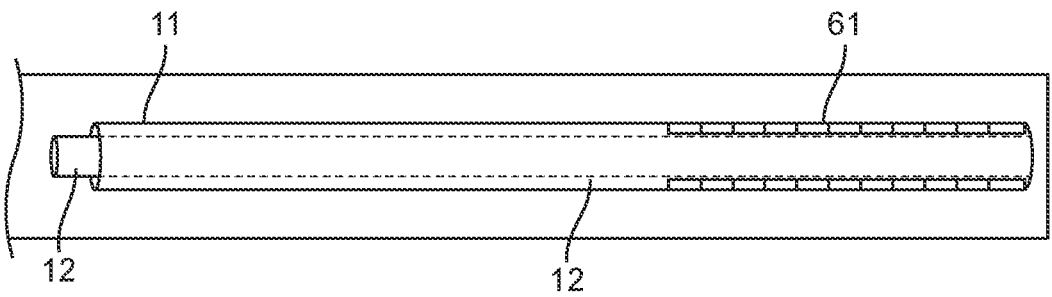
FIG. 6A shows a cross-sectional view of a device comprising an expandable element in a collapsed configuration, with the collapsed expandable element positioned over the inner catheter shaft, in accordance with embodiments.

10 in the expanded configuration (e.g., wherein a distal-most portion of the expandable element has a greater diameter than the proximal-most portion(s) of the expandable element, which may be coupled, for example, to the inner and/or outer catheter shafts. In some cases, the expandable element can have a collapsed configuration (e.g., as shown in FIG. 6A), for example, wherein the expandable element has a diameter at its distal-most end equal to or substantially equal to one or more of an inner diameter of the inner catheter shaft, an outer diameter of the inner catheter shaft, an inner diameter of the outer diameter shaft, or an outer diameter of the outer diameter shaft. In some cases, an expandable element in a collapsed configuration can be disposed entirely, substantially, or partially within the lumen of an outer catheter shaft 11 and/or an inner catheter shaft 12 of the device or system. In some cases, an expandable element can have a substantially tubular shape (e.g., a cylindrical tubular shape) when the expandable element is in a collapsed configuration. In some cases, an expandable element can be made to transition from the collapsed configuration to the expanded configuration (and, in many cases, from the expanded configuration to the collapsed configuration) by translation (e.g., moving) the inner catheter shaft 12 relative to the outer catheter shaft 11, e.g., in a longitudinal direction. For example, the expandable element can be is deployed to an expanded configuration by a push-pull action of the inner and outer catheter shafts. In some cases, the inner catheter shaft can be translated (e.g., slid) distally within the outer catheter shaft to transition the expandable element from a collapsed configuration to an expanded configuration. In some cases, the outer catheter shaft can be translated proximally relative to the inner catheter shaft to transition the expandable element from a collapsed configuration to an expanded configuration. In some cases, translating the inner catheter shaft distally with respect to the outer catheter shaft until the distal end of the inner catheter shaft is level with the distal end of the outer catheter shaft (e.g., as shown in FIG. 1) can cause the expandable element to transition from a collapsed configuration to an expanded configuration. In some cases, the inner catheter shaft can be translated distally so that the distal end of the inner catheter shaft is more distal than the distal end of the outer catheter shaft (e.g., as shown in FIG. 3A). In some cases, the expandable element can be caused to transition from an expanded configuration to a collapsed configuration (e.g., can be collapsed) by translating the inner catheter shaft proximally relative to the outer catheter shaft, for example, so that the distal end of the inner catheter shaft is retracted within (e.g., translated to a position more proximal than) the outer catheter shaft. In some cases, the expandable element can be caused to transition from an expanded configuration to a collapsed configuration by translating the outer catheter shaft distally relative to the outer catheter shaft. In some cases, the device can be configured such that expansion of the expandable element (e.g., to expanded configuration having a funnel shape) limits the further translation of the two shafts relative to one another when the funnel is fully expanded or fully collapsed, which can be useful for causing full deployment and full collapse of the expandable element. In some cases, the device can be configured such that expansion of the expandable element (e.g., to an expanded configuration) does not limit the further translation of the two shafts relative to one another when the funnel is fully expanded or fully collapsed.

In some cases, a catheter shaft (e.g., a wall of a catheter shaft) of the device or system can comprise one or more apertures 17 (e.g., a plurality of apertures). In some cases, including one or more apertures in a wall (e.g., of a distal end) of an inner catheter shaft can improve the ability of the device or system to remove material from the lumen of the body cavity 9 (e.g., removal of blood clot from the blood vessel lumen). One or more apertures in (e.g., a distal end of) a wall of an inner catheter shaft, an outer catheter shaft, or both can decrease the friction (e.g., "provide lubrication") between a material to be removed from the lumen the catheter shaft, for example, by allowing blood to enter the lumen of the inner catheter shaft and/or an interior region of the expandable element. In some cases, the one or more apertures may be exposed to systemic blood when a distal end of the outer catheter shaft is withdrawn to a position proximal of the distal end of the inner catheter shaft. In such a configuration (e.g., when the expandable element is deployed, for example in the shape of a funnel, and is positioned to occlude flow, with the distal end of the inner catheter shaft substantially even with the distal end of the outer catheter shaft, the apertures in the wall of the distal end of the inner catheter shaft are covered by a wall of the distal end of the outer catheter shaft. By withdrawing the outer shaft to expose the apertures, small amounts of upstream systemic blood can be directed to flow through the apertures and into the lumen of the catheter (e.g., as shown by blood flow lines 19 in FIG. 2). This can create a "flow" of fluid along the inner wall of the catheter shaft and into the suction syringe or pump which can aid in translating material (e.g., thrombus fragments) with the flow in a proximal direction within the lumen of the inner catheter shaft.

Figure 2:
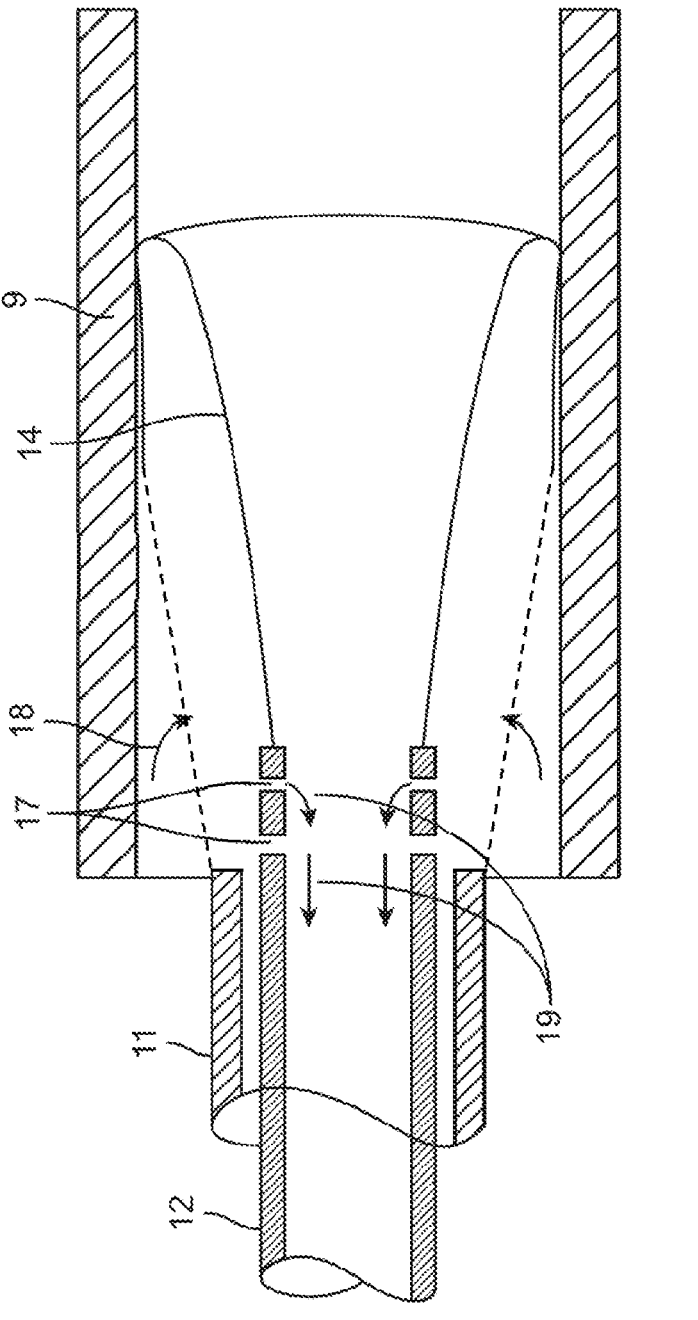
FIG. 2 shows a schematic of a device comprising an inner catheter shaft comprising apertures, an outer catheter shaft, and an expandable element, in accordance with embodiments.

In some cases, a device or system described herein (e.g., a funnel catheter 10 described herein) can comprise an outer shaft 11, an inner shaft 12, and an expandable element, the expandable element comprising a non-porous segment 14 (e.g., as represented in FIG. 1 and FIG. 2 by a single bold line) and a porous segment 13 (e.g., as represented in FIG. 1 and FIG. 2 by a non-continuous, dotted line). In some cases, a porous segment of an expandable element can be permeable to a fluid, such as blood. In some cases, a non-porous segment 14 may be impermeable to a fluid, such as blood. In some cases, a porous segment, a non-porous segment, or both a porous segment and a non-porous segment of an expandable element can prevent the passage therethrough of a material being removed from a lumen of a body cavity (e.g., debris or all or a portion of a thrombus in a blood vessel). In some cases, all or a portion of the expandable element can be braided. For example, the expandable element can comprise a mesh, such as a braided mesh, with the two ends of a tubular braided structure attached to the distal ends of both the inner and outer sheaths. The tubular braided structure comprises an impermeable area containing an elastomeric coating and a permeable area free of a coating that allows blood to flow into the impermeable U-shaped end of the funnel apparatus to expand the funnel against the vessel wall. In some cases, a catheter-based device 10 can be expanded with permeable 13 and impermeable 14 sections of the braid apparatus. As described herein, the catheter-based device 10 can comprise apertures 17 within the distal aspect of the inner catheter shaft 12 that can be covered (e.g., and occluded) by outer catheter shaft 11, which can in some cases prevent the ingress of blood through these apertures into the lumen of the inner catheter shaft. In some cases, the outer catheter shaft 11 can be withdrawn (e.g., a few millimeters (mm), for example 1 to 3 mm, 3 to 5 mm, 5 to 7 mm, or 1 to 7 mm) to uncover the apertures 17 (e.g., and allow ingress of blood through the apertures). In some cases, this configuration can be used to allow blood 18 to flow through the permeable portion 13 of the braid apparatus and through the apertures 17 into the lumen of the inner catheter shaft. Arrows 18 shown in FIG. 2 illustrate the flow of systemic blood from the outer aspect of the outer sheath 11 of the device, through the permeable braid 13, and into the lumen of the inner shaft 19, in accordance with some embodiments. An aperture 17 of a system or device described herein may be sized, for example, from 0.001 inches to 0.050 inches, although preferably from 0.003 to 0.020 inches. In some cases, an aperture 17 can be from about 0.001 inches to about 0.05 inches.

A device or system described herein (or a component thereof, such as a distal end of an inner catheter shaft) can have 1, 2, 3, 4, 5, 6, 7, 8, 9, 10 or more than 10 apertures. For example, a device or system described herein (or a component thereof, such as a distal end of an inner catheter shaft) can have 10 to 15, 16 to 20, 21 to 25, 26 to 30, 31 to 36, or more than 36 apertures (e.g., preferably from 1 to 36 apertures). In some cases, a plurality of apertures 17 may be grouped or arranged in a pattern or a regular or irregular configuration. In some cases, an aperture can be may be created by laser ablation, drilling, mold-based fabrication, or methods known in the art.

FIG. 3A and FIG. 3B show an example of a system or device 10 described herein having an inner catheter shaft 12 and an outer catheter shaft 11. In FIG. 3A, the inner catheter shaft 12 is shown advanced (e.g., in a distal direction) relative to the outer catheter shaft 11, which can expose a plurality of apertures 17 in the wall of the inner catheter shaft to upstream systemic blood flow 18 and can allow the blood to be aspirated through the apertures 17 and into the lumen of the inner shaft 12.

As described herein, such a configuration may serve several purposes in addition to providing liquid (e.g., blood) to the interior of the inner catheter shaft to lubricate the thrombus/catheter interface and diminish friction between the thrombus and the catheter wall. By providing apertures for the ingress of systemic blood that is under positive pressure (normal mean arterial blood pressure is 70-100 mm Hg) along with negative pressure applied, for example, to the interior of the inner catheter shaft using a suction syringe or pump (e.g., which may be configured to approximate or achieve 700 mm Hg negative pressure within the inner catheter shaft lumen), the blood flowing through the apertures can be accelerated through the apertures according to Bernoulli's principle. This acceleration can create tiny jets of fluid (e.g., blood) through the apertures which may impact a thrombus in the blood vessel or in the lumen of the expandable member and/or the inner catheter shaft and tend to fragment it into smaller pieces and/or to make it less organized and easier to aspirate. In some cases, the apertures can be used to provide liquid (e.g., blood) to the interior of an inner catheter shaft to lubricate the passage of the thrombus and overcome friction and also to disrupt some parts of the thrombus. In some cases, this can be especially useful for disrupting or fragmenting the surface of a thrombus, as the thrombus may be compressed by the transformation to a smaller diameter during entry into the lumen of the inner catheter shaft. In some cases, compression of the clot can liberate some fluid and contribute somewhat to the lubrication of the inner surface of the inner shaft; however, the additional apertures can also provide more fluid and the surface disrupting jets to partially disrupt the clot to further enhance passage of the clot through the catheter shaft.

In some embodiments, an impermeable portion of the expandable member (e.g., a portion of the tubular braid which forms the funnel component of the expandable member) can comprise one or more apertures. These apertures may be positioned on a funnel (e.g., inner, tapered) portion of the expandable member so that they are covered by a wall of the outer catheter shaft when the expandable member is deployed and the aperture(s) of the expandable element are completely occluded by the outer catheter shaft but exposed to systemic blood when the outer sheath is retracted (e.g., to provide apertures through which small jets of blood and, in some cases, the resultant turbulence can contact the surface of the thrombus and serve to at least partially fragment the surface of the thrombus). Apertures disposed within the funnel (e.g., tapered, inner) portion of the expandable member can serve to lubricate the funnel as the thrombus is compressed from a larger vessel sized thrombus to a smaller and more compact configurations as it is drawn into or forced into the funnel base and then into the catheter shaft (e.g., by application of a negative pressure, for example, to a proximal end of the inner catheter shaft). In some cases, this can diminish the friction created by the compression of the thrombus while partially fragmenting the thrombus, both of which actions may be useful in facilitating the passage of the thrombus from the blood vessel into the inner catheter shaft and through the inner catheter shaft for removal. In some cases, the blood can flow through the permeable braid section (e.g., outer layer) of the expandable member and then through one or more apertures of the non-permeable section of the expandable member and into the inner aspect of the expandable member and then into the lumen of the inner catheter shaft of the device.

In some cases, the apertures described above, whether within the distal aspect of the inner shaft of the catheter or within portions of the (e.g., braided) expandable element, may cause unintended or unwanted effects if left exposed or "open" to allow blood flow through the apertures during some or most of the procedure when complete occlusion of flow may be desirable. In some cases, it can be advantageous to configure the catheter apparatus so the apertures are exposed, or open to blood flow, at only selective times during the procedure, for instance, so that the risk of propelling thrombus fragments further downstream is minimized. In some cases, the apertures can be exposed or "open" to flow therethrough until the thrombus is withdrawn into the funnel by one or more of suction, traction, and a combination of suction and traction.

To conveniently accomplish this intermittent exposure or activation of the apertures, a manual or automatic actuator near the hub of the catheter can be provided wherein the actuator is configured to expose and cover the apertures, for instance, by regulating the degree of translation of the inner and outer shafts, whether the distal end of the inner catheter shaft is translated distally such that the apertures are in the lumen of the funnel formed by the expandable element in its expanded configuration or if the apertures of the inner catheter shaft are within the walls of the outer catheter shaft. Configured in this way, an operator may expose the apertures so blood will flow through the apertures into the lumen of the inner catheter shaft in fluid "jets" only when desired during the procedure. Hence, the default position of the catheter apparatus may be that the apertures are closed or covered (e.g., by the wall of the outer catheter shaft) to prevent any permeability or blood flow through the apertures. This actuator mechanism may be a spring-loaded or other mechanism that is more or less instantly operable by the physician or operator when desired. The actuator mechanism may be activated by thumb or finger control to translate the outer shaft 11 in relation to the inner shaft 12 to expose the apertures 17 so that intermittent "pulses" of flow through the apertures occurs only when there is suction provided by a syringe or pump. By providing this mechanism, the positive effects of the small jets may be utilized when needed during the procedure, and the negative effects of the apertures can be avoided at those times during the procedure when the positive effects are not needed or desired.

Similarly, the apertures 17 can provide relief from the relative vacuum which may develop behind the thrombus as a thrombus that enters the catheter shaft can be subject to the actions of the blood jets spraying through the apertures and can be carried down the catheter shaft by such. The thrombus distal to the apertures may need to be pulled into the funnel and catheter shaft by the combined action of the suction provided and the enhanced flow as a result of the actions of the apertures. In the rare case the above method is unsuccessful at aspirating a distal clot, a coaxially inserted clot retractor or another device may be inserted and utilized to retract the thrombus into and through the catheter.

Figure 4A:
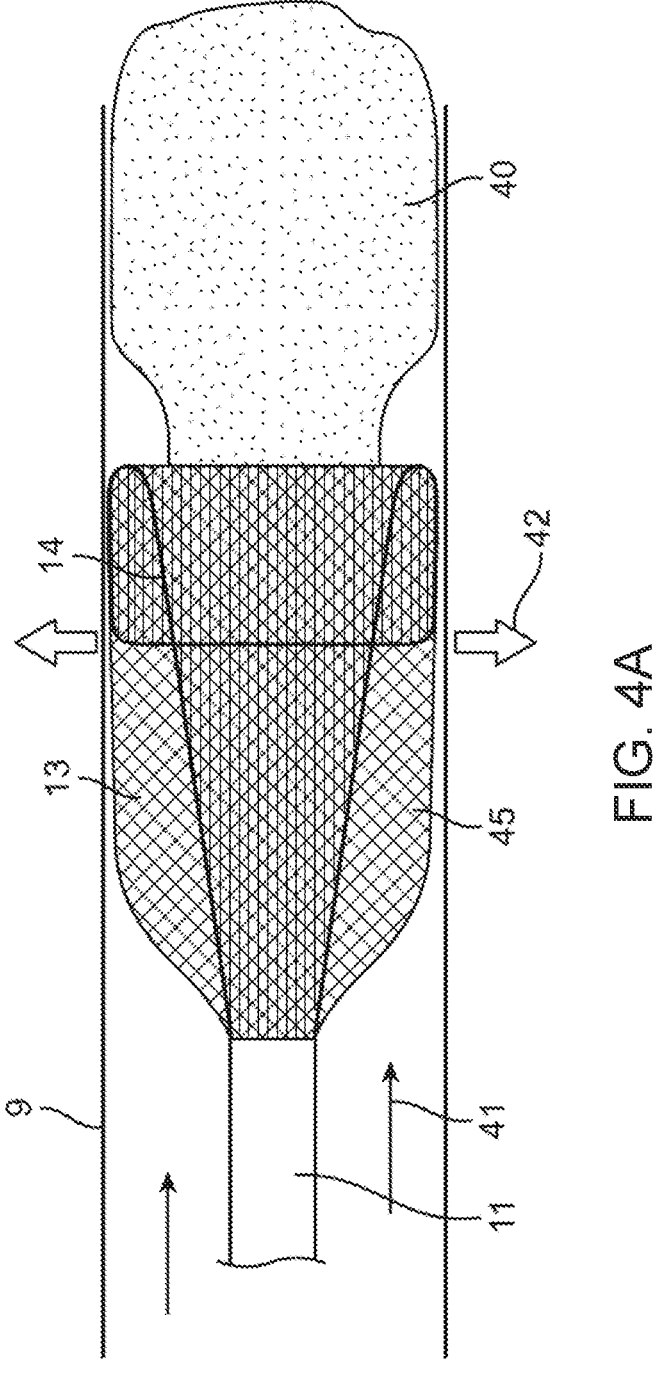
FIG. 4A shows a schematic of use of a device comprising an inner catheter shaft comprising apertures, an outer catheter shaft, and an expandable element, with a thrombus distal to the device, in accordance with embodiments.
Figure 4B:
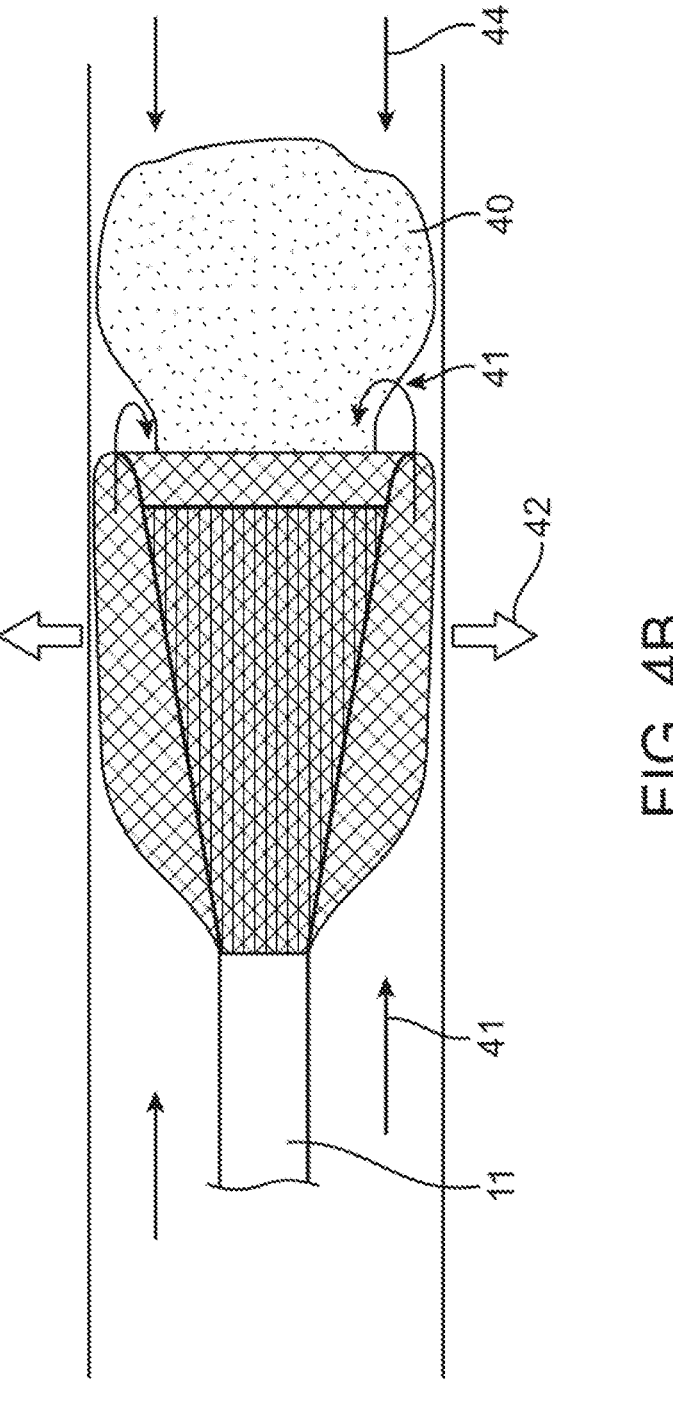
FIG. 4B shows a schematic of use of a device comprising an inner catheter shaft comprising apertures, an outer catheter shaft, and an expandable element, with a thrombus partially aspirated by the device, in accordance with embodiments.

Furthermore, the permeable and impermeable sections of the expandable element may be positioned by the operator to occlude blood flow incompletely while providing suction. This would allow upstream blood to flow into the braid apparatus and into the funnel around the impermeable section of the braid that may be positioned on the internal aspect of the funnel. This is depicted in FIG. 4A and FIG. 4B. In FIG. 4A, the thrombus 44 is partially ingested into the expanded expandable element 45, but not aspirated completely, e.g., because of friction with the inner surface of expandable element and/or the inner catheter shaft, which can be caused by the composition and the size of the thrombus 44. In FIG. 4B, the respective shafts of the catheter have been translated to provide only partial occlusion of flow through the blood vessel, so that some upstream blood 41 is aspirated with the thrombus, thereby lubricating the wall of the expandable element 45 and the catheter lumen for easier aspiration of the thrombus 44. A method comprising placing a catheter-based device or system into a configuration of full occlusion and attempting to aspirate the clot with full occlusion followed by one or more episodes of partial occlusion (and/or switching back and forth between complete and partial occlusion) can help to lubricate the funnel and the shaft of the catheter-based device or system and successfully aspirate the thrombus.

In some cases, blood flow occlusion may not be desirable at times, for instance, while there is a need for anchoring. This may occur during navigation to a target site (e.g., wherein the target site comprises a material (e.g., a thrombus or debris within a vessel) or a location of the blood vessel comprising the material) with guide wires and/or catheters in which there is one or more of tortuous vessels, tight stenoses, difficult anatomy, chronic total occlusion, or other barrier to navigation of the vessel to reach the target site. Anchoring of the catheter-based device or system can serve to facilitate passage and navigation to the target site, but occlusion during the navigation process may cause undesirable ischemia and pain if prolonged. To solve this issue, a catheter-based system or device described herein can be configured to 1) to anchor while occluding flow and/or 2) to anchor while not occluding flow within the vessel.

Figure 5A:
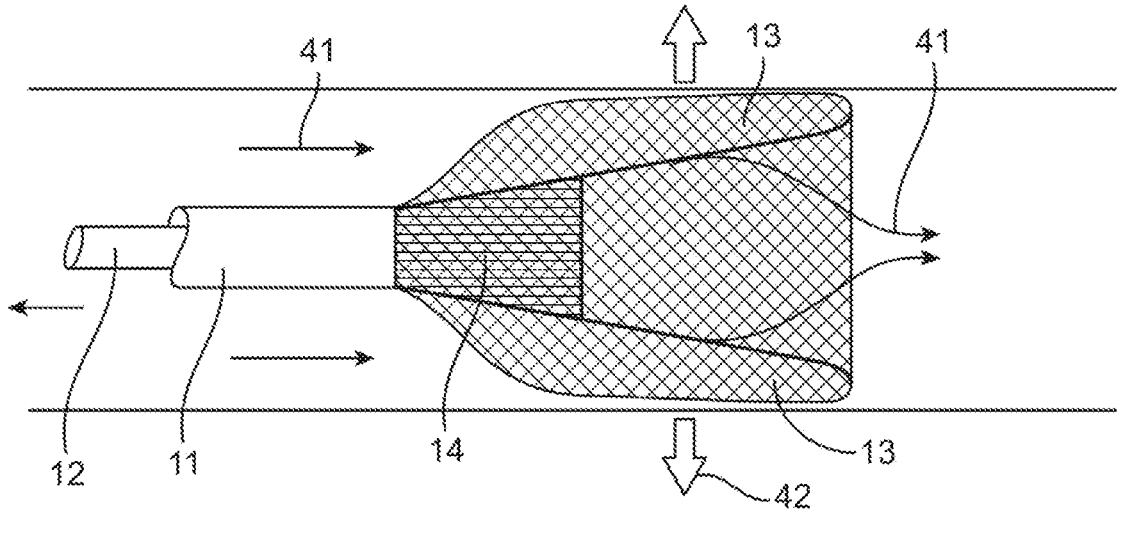
FIG. 5A shows a schematic of use of a device comprising an inner catheter shaft comprising apertures, an outer catheter shaft, and an expandable element, the expandable element expanded so that the permeable portion allows distal blood flow, in accordance with embodiments.
Figure 5B:
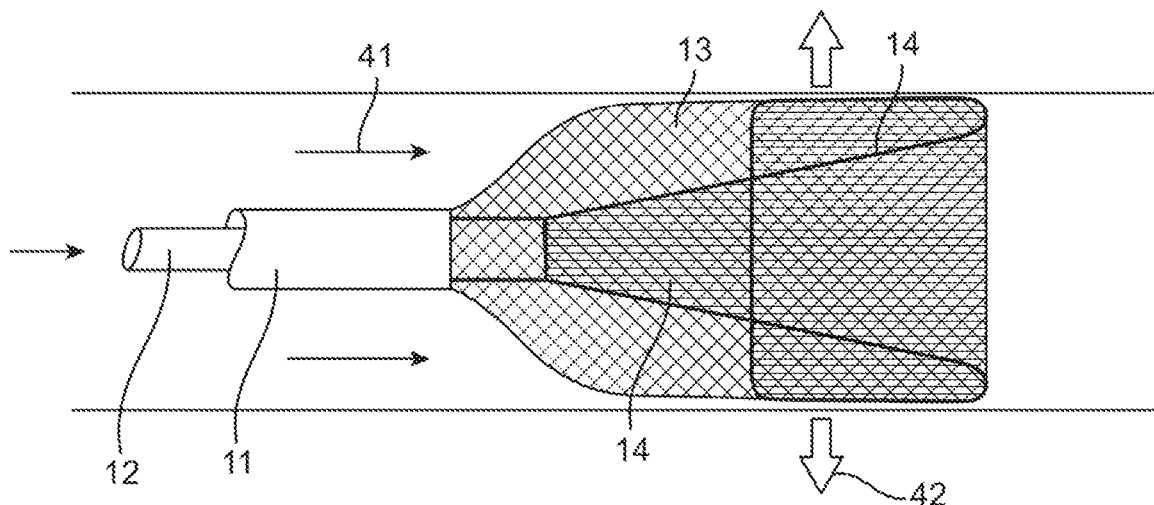
FIG. 5B shows a schematic of use of a device comprising an inner catheter shaft comprising apertures, an outer catheter shaft, and an expandable element, with the non-permeable section of the expandable element positioned to occlude blood flow, in accordance with embodiments.
Figure 6B:
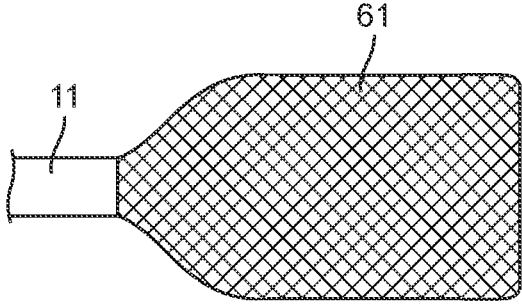
FIG. 6B shows a schematic of an expandable element in an expanded configuration, in accordance with embodiments.
Figure 6C:
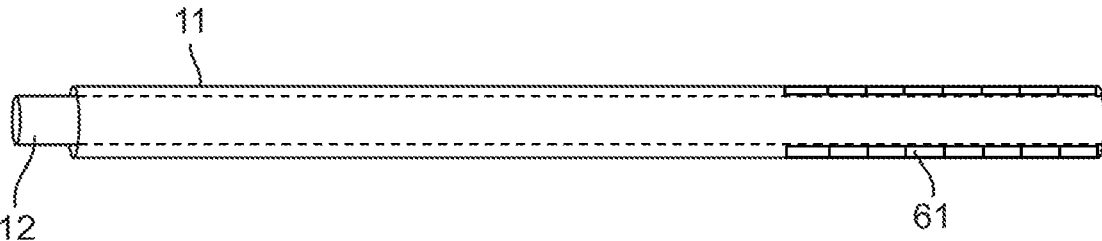
FIG. 6C shows a view of a device comprising an expandable element in a collapsed configuration, with the collapsed expandable element positioned within the outer catheter shaft, in accordance with embodiments.

In some cases, the catheter-based device or system can comprise a mechanism for controlling the anchoring action of the device or system, e.g., so that the transition from occluded to non-occluded state and back to occluded state is easily actionable and convenient for the operator. In some cases, a permeable section of the expandable element can be elongated, for instance as a point of attachment to the distal end of the outer shaft 11 and a shorter segment of nonpermeable braid or mesh 13 of the expandable element can be attached to the distal end of the inner shaft 12, e.g., as shown in FIG. 5A and FIG. 5B. In some cases, beginning with the entire braid structure 61 housed within the outer shaft 11 as illustrated in FIG. 6C, when the outer sheath is retracted as depicted in FIG. 5A, the elongated porous and permeable portion 13 of the expandable element may be exposed first and may contact the vessel wall 9 where it can provide anchoring and stabilization of the distal catheter while not preventing the antegrade flow of blood. The non-porous or impermeable segment 13 can remain housed within the outer catheter shaft 11 or within the expandable element 45 and occlusion of flow (e.g., as in existing devices) can be avoided. In this configuration, anchoring can be achieved while coaxial members are navigating or traversing vessels to the target site or performing other actions while preserving blood flow thereby preventing ischemic damage to the distal tissues during this phase of the procedure. The anchoring effect of the porous segment 13 of the expandable element may be enhanced by heat setting the nitinol used to form the braid or mesh of the porous segment of the expandable element to provide this section with an outward radial force sufficient to anchor and stabilize the distal catheter as in this configuration the ability to anchor is dependent solely on the radial outward force of the braid. Once the target site is reached, the outer sheath may be retracted further as shown in FIG. 5B to expose and deploy the non-porous segment of the braid 14 to occlude the vessel 9 while continuing to anchor so that the desired procedure may be performed in a static environment with proximal protective flow arrest providing embolic protection as well as enhanced aspiration efficiency. In some cases, (e.g., as shown in FIG. 5B), the anchoring function can be primarily a result of the patient's blood pressure pressing the non-porous section 14 against the vessel wall.

In some cases, and expandable element of a catheter-based device or system can be transitioned from a collapsed funnel state to 1) an expanded funnel state with anchoring and without occlusion and then to 2) an expanded funnel state that anchors the device while the funnel is occluding blood flow in the vessel.

Further in the instant method, once the interventional devices or tools are positioned at or near the target site, the push-pull mechanism of the catheter-based device or system may be utilized to further deploy the expandable element, which may comprise tubular braid comprising impermeable or non-porous sections thereby occluding the vessel and creating a static work environment for the utilization of the interventional tools and devices. The occlusion may prevent distal embolization and provide for aspiration or mechanical removal of debris liberated during the intervention before it has an opportunity to embolize distally. After the target site is treated and debris aspirated or mechanically removed, the expandable element may be returned to the anchoring without occlusion configuration while allowing time for a user (e.g., a practitioner) to assess the result of the intervention and whether there are other lesions further downstream or elsewhere that may need to be treated. The funnel apparatus may be utilized in a configuration of anchoring without occlusion to further assist in navigation of coaxial members distally to address any additional lesions or areas and subsequently collapsed for advancement over the coaxial members to a site more proximal to this second target site.

Hence, one improvement represented by some embodiments of the catheter-based devices and systems described herein is to provide an elongated porous section of tubular braid (of the expandable element) which allows the flow of blood therethrough when deployed against the vessel wall to stabilize and anchor the catheter to the vessel wall without occluding the vessel and a second section of non-porous tubular braid of the expandable element, which upon further deployment of the braid by further movement of the ends of inner and outer shafts in closer proximity to one another can produce occlusion of blood flow while maintaining the anchoring and centering functions. Another improvement is the method of translating the sheaths relative to one another so that anchoring of the catheter to the vessel wall can be achieved without occlusion. Upon further translation of the inner and outer sheaths, the impermeable section may be deployed which can cause the expandable element to anchor on the blood vessel while occluding blood flow. The method may also include anchoring without occlusion during navigation to the target site and other maneuvers in which blood vessel occlusion is not desirable and then occluding the vessel with the funnel catheter during the appropriate intervention of the target site lesion and changing between anchoring with and without occlusion during the procedure.

In some cases, a catheter-based device or system can comprise a tubular mesh braid attached to the ends of the inner and outer shafts. When collapsed the tubular mesh braid of the expandable element can be in a cylindrical shape collapsed over the inner shaft. The funnel can be formed when the distal ends of the inner and outer catheter shafts approximate or overlie one another. A stop or detente may be provided so that the further translation is prevented once the ends overly one another and the funnel shape is achieved. In some cases, additional (e.g., specifically placed) détentes that give a tactical or visual feedback to the operator during the transition process from non-occlusion to occlusion and from occlusion to non-occlusion may be added to a catheter-based device or system described herein. The handle mechanism which controls the translation of the inner and outer sheaths may be so modified to comprise a means to affect a temporary stop in the translation process at the points of anchoring with no occlusion and at the point of anchoring with occlusion. These means may be a friction fit apparatus on the handle, a rotational means, a latch like means, or other means that give tactile or visual positional feedback via markings on the handle apparatus to the user that the expandable element's funnel position is in either an occluding or non-occluding state. Radiopaque markers may also be used on each of the outer and inner sheaths to inform the operator via fluoroscopy as to the relative positions of the outer and inner sheaths and reflect the relative deployment of the funnel with different positions of two or more markers. The markers alone may not inform the operator of the position of the funnel deployment in the improved embodiments as it may be difficult to determine which marker is which by fluoroscopic evaluation. In some cases, when the marker bands overlap, the funnel is in the expanded configuration, and when the marker bands are separated by a specific distance, the funnel of the expandable element is configured to be in the collapsed configuration. In some cases, the increased options for translation of the two shafts in the improved embodiment can obviate the simple feedback of such devices since the markers on the two shafts may be in several different positions relative to one another depending on the degree of translation of both the inner and outer shafts.

Similarly, additional stops or détentes may be utilized to withdraw the outer sheath proximally over the inner sheath to expose apertures previously described in FIGS. 2 and 3 to allow ingress of systemic blood to facilitate the passage of a thrombus or other material into and through the catheter shaft. In the case of apertures within the proximal portion of the non-permeable braid connected to the inner sheath, a detente may be utilized so that the outer sheath covers these apertures. Another detente may be provided when the outer sheath is withdrawn to a position in which the apertures are exposed to systemic blood while the remaining parts of the expandable element are occluding blood flow. This position may be achieved by use of a spring like mechanism or other means to cause the outer sheath to cover the apertures and prevent systemic blood from flowing therethrough without actions by the operator to withdraw the outer sheath with manual manipulation. This would create a situation in which the apertures are covered or closed and non-operative without an action by the operator to actively open the apertures by actively and persistently withdrawing the outer sheath to expose these apertures. This can provide a useful safety feature to avoid inadvertently leaving the apertures open and allowing systemic blood to flow into the funnel or catheter shaft and propel thrombus or debris downstream when suction is not provided in the suction syringe or pump or when the catheter shaft may be occluded or partially occluded.

In utilizing a catheter-based device or system comprising an expandable element with a mechanism available to transition from anchoring with occlusion to anchoring without occlusion and so forth, the tubular braid of the expandable element may be translatable so that it may be positioned 1) over the inner shaft and/or 2) within the outer shaft when collapsed and in a cylindrical shape. FIG. 6A demonstrates the braided 61 expandable element collapsed along the outer side of the inner shaft 12. FIG. 6B demonstrates the expandable element 61 in the expanded configuration (e.g., expanded or deployed). FIG. 6C demonstrates the braid apparatus 61 (e.g., braided expandable element) to be aligned along the inner side of the outer shaft 11. This variable configuration can allow versatility in the placement of the braid with respect to the shafts and will allow versatility in the introduction of the expandable element into a vessel, the navigation of the expandable element to an appropriate position proximal to the target site needing intervention, and in the ability to anchor the distal tip of the expandable element both with and without occlusion. In some cases, the braid, being positioned inside the outer catheter shaft, may not be exposed to the vessel wall during vessel entry or navigation of the catheter as the braided surface has the potential to create friction or even damage the vessel wall. However, the braid of the expandable element may need to be positioned outside of the inner catheter shaft so that it is exposed to the vessel wall during certain anchoring and occlusion functions. This variable configuration and the simple translation between the configurations in FIGS. 6A-6C can facilitate the optimal braid position for entry, navigation, anchoring, and occlusion amongst other actions. The variable configuration will also make additional maneuvers described subsequently feasible.

The instant expandable element may also provide the means necessary to reach a distal target site with the expandable element in tortuous and difficult vascular anatomy and to perform a unique and novel method of advancing catheters through difficult vascular anatomy. This method can be utilized with a catheter-based device or system when a tortuosity prevents the forward movement of the catheter by the traditional methods of pushing the catheter forward while manipulating the guide wire in a static position. In the instant method, when a relative impediment to forward placement of the catheter is encountered, movement of one of the of the inner and outer sheaths

Figure 7A:
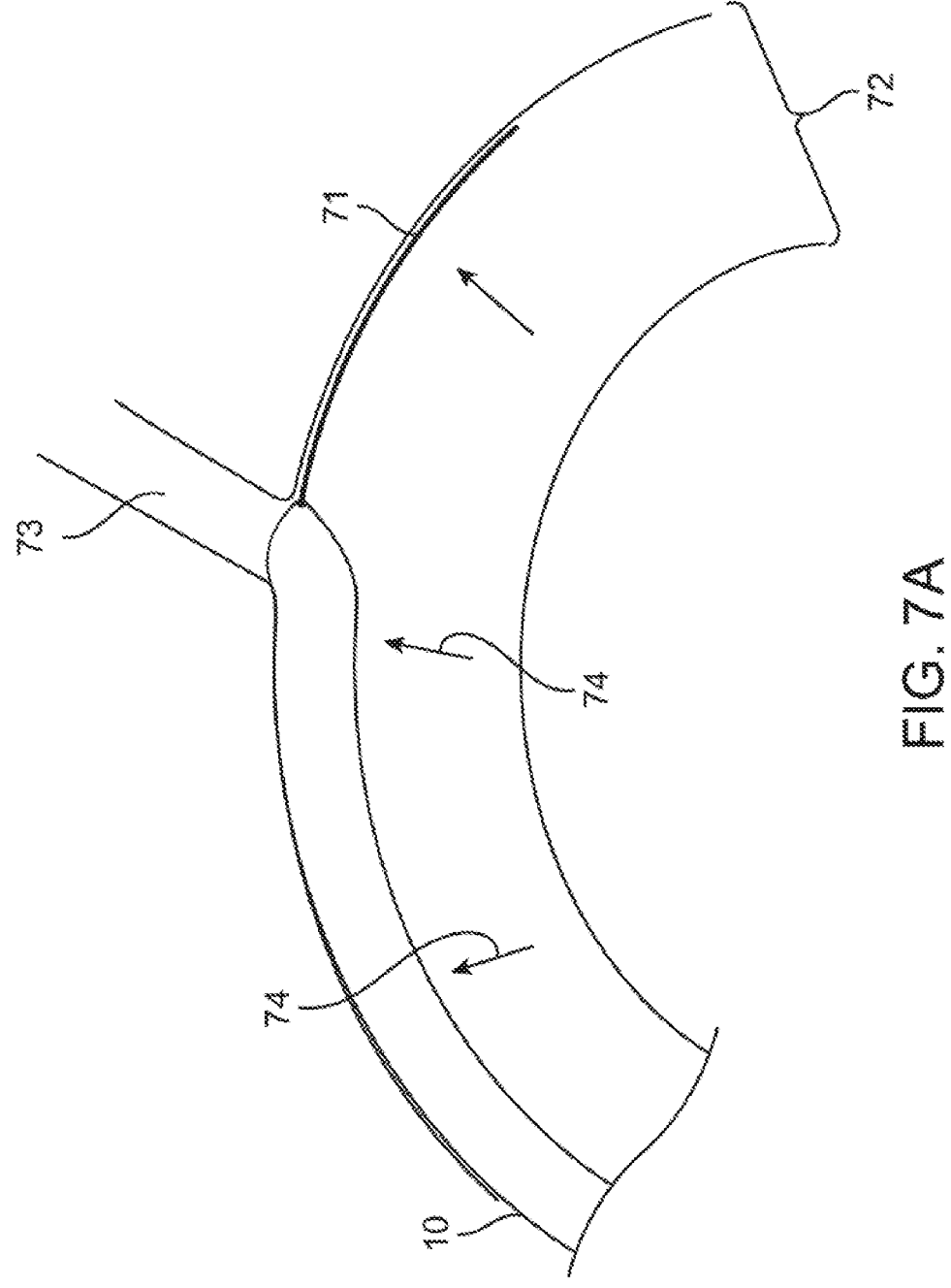
FIG. 7A shows a schematic of a device comprising an expandable element used for navigating a blood vessel, in accordance with embodiments.
Figure 7B:
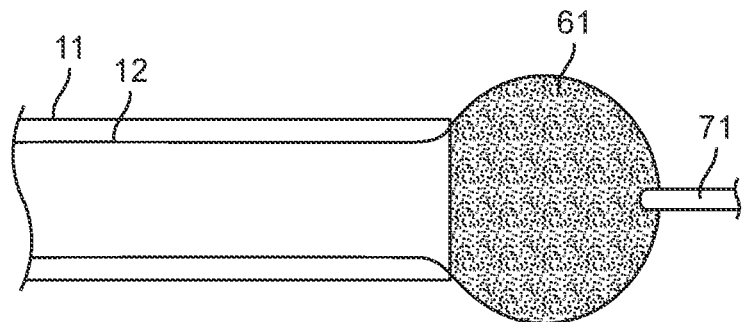
FIG. 7B shows a schematic of a device comprising an expandable element useful in navigating a blood vessel, with the tip of the catheter engaged in the orifice of a side branch, in accordance with embodiments.
Figure 7C:
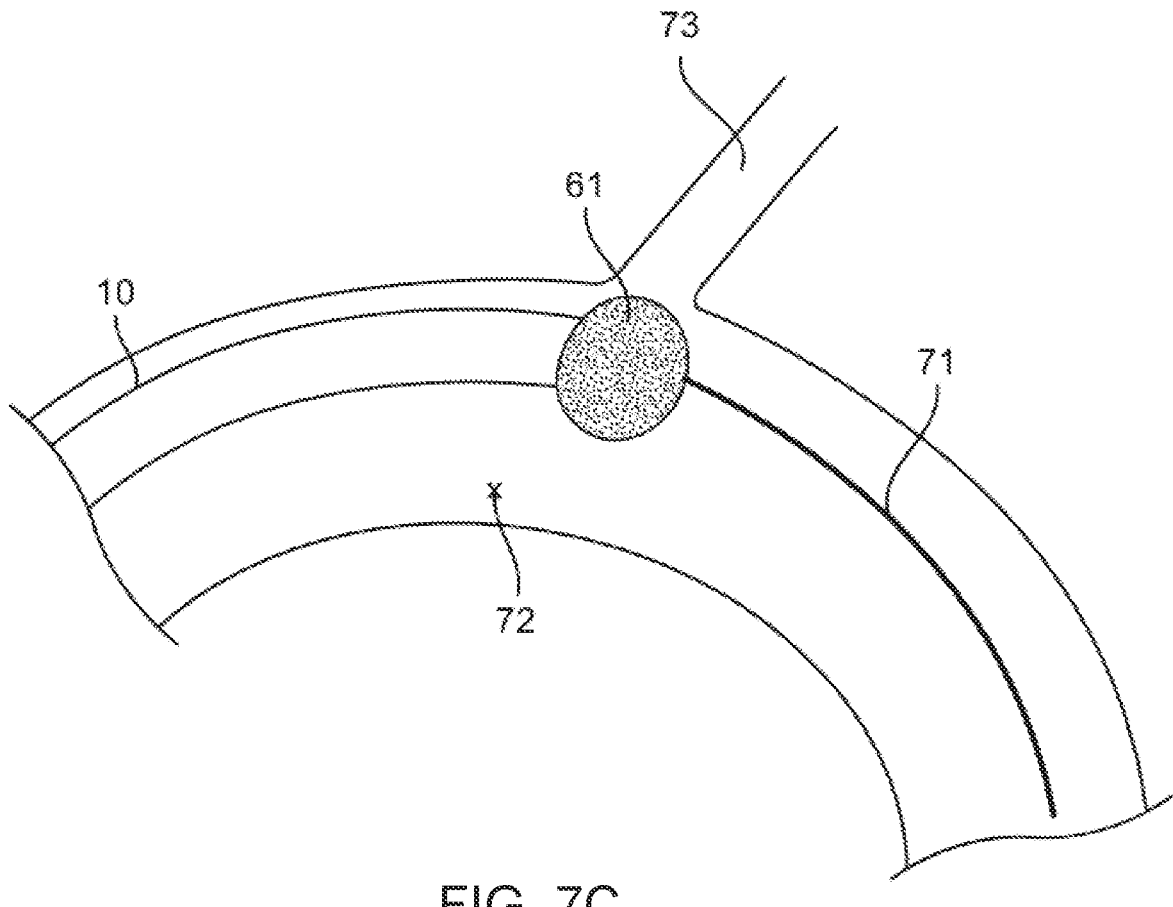
FIG. 7C shows a schematic of a device comprising an expandable element used for navigating a blood vessel, with the expandable element partially expanded, in accordance with embodiments.

18 forward a few millimeters followed by forward movement of the other of the inner and outer sheath and repeating this process will allow the funnel tipped catheter to "crawl" along the artery in an inchworm like fashion that will overcome the relative impediment to advancing the catheter and allow access to more distal vascular territory. For example, the carotid siphon is a tortuous segment of the distal internal carotid artery which presents a challenge to navigation and distal placement of a thrombectomy catheter tip at or within the proximal middle cerebral artery for stroke intervention purposes so to retrieve the embolus or thrombus lodged in the middle cerebral artery. The catheter may be flexible enough but the transition between the guide wire or an aspiration microcatheter placed coaxially within the thrombectomy catheter may cause a portion of the thrombectomy catheter tip to partially engage the origin of the branch vessel 73 (e.g., ophthalmic artery) and prevent forward advancement of the catheter-based device or system 10 (e.g., which may be configured as a thrombectomy catheter, for instance comprising a guidewire 71) in the distal internal carotid artery 72 (for example, due to a force 74 exerted on a wall of the artery 72), e.g., as demonstrated in FIG. 7A. This is not an uncommon problem. To solve this dilemma, if the collapsed catheter-based device or system 10 of the present disclosure were to engage the origin of the ophthalmic artery 73 or other vessel in such a manner while navigating towards the target vessel, advancing the inner shaft 12 can partially expand the braid as demonstrated in FIG. 7B, followed by advancement of the outer shaft 11 and repeating the process can allow the catheter to advance beyond this impediment. This action and method would provide a benefit over existing standard and funnel thrombectomy catheters in overcoming obstacles to navigability and proper placement of the catheter tip. The method of navigating a catheter-based device or system described herein can comprise expanding the expandable element, so that the partially expanded funnel is larger than the outer dimension of the catheter and larger than the orifice of the side branch but smaller than the expansion necessary to engage the vessel wall circumferentially, to provide disengagement from a side branch origin and avoidance of engagement in a side branch origin while displacing the tip of the catheter towards the center of the vessel, providing a longitudinal force to push the catheter forward, and then collapsing the expandable element. In some cases, an expandable element of a catheter-based device or system described herein can be used for navigating a blood vessel with the expandable element partially expanded, for example, as shown in FIG. 7C.

An additional advantage of a configuration of a catheter-based device or system with the expandable element translatable from a collapsed state in which the expandable element is on the inside of the outer shaft may be in delivery of the catheter-based device or system to the target site without exposing the expandable element to the vessel wall. If the braid is covered by the outer shaft, then the outer shaft smooth surface would contact the vessel wall instead of the mesh braid configuration being exposed to the vessel wall. This will facilitate easier passage of the catheter with the smooth surface of the outer shaft being exposed to the vessel wall rather than the braid being exposed to the vessel wall, thereby obviating any concern of potential damage to the vessel endothelium or plaque that may be present during the transit. After transit and delivery to a point near the target site, the braid may then be deployed from the internal location to form a funnel or translated to occupy a position covering the inner sheath in a collapsed position. Presented herein are catheter-based devices and systems 10 that are fully translatable from the expandable element 61 positioned on the inside of the outer sheath 11 in a collapsed configuration to deployment of the funnel 61 so that there is anchoring without occlusion and to further deploy the funnel 61 so that there is anchoring with occlusion of blood flow and then to the expandable element positioned on the outside of the inner sheath 12 in a second collapsed configuration as demonstrated in FIGS. 6A, 6B, and 6C.

Figure 8A:
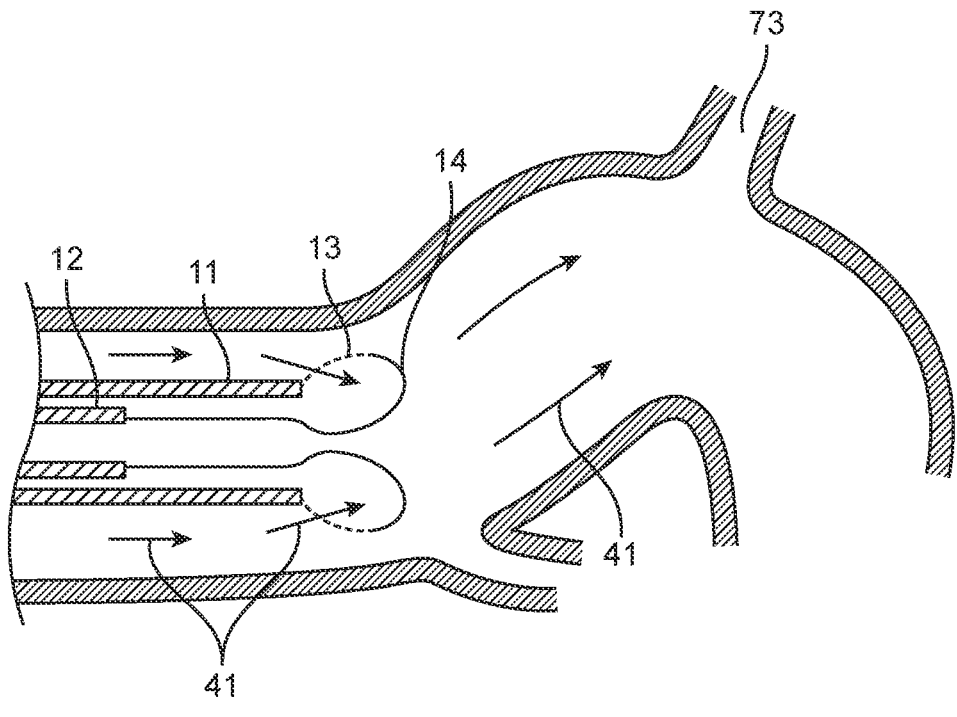
FIG. 8A shows a schematic of a device comprising an expandable element used for navigating a blood vessel, with the expandable element partially deployed and entraining some of the forward blood flow to urge the device forward, in accordance with embodiments.
Figure 8B:
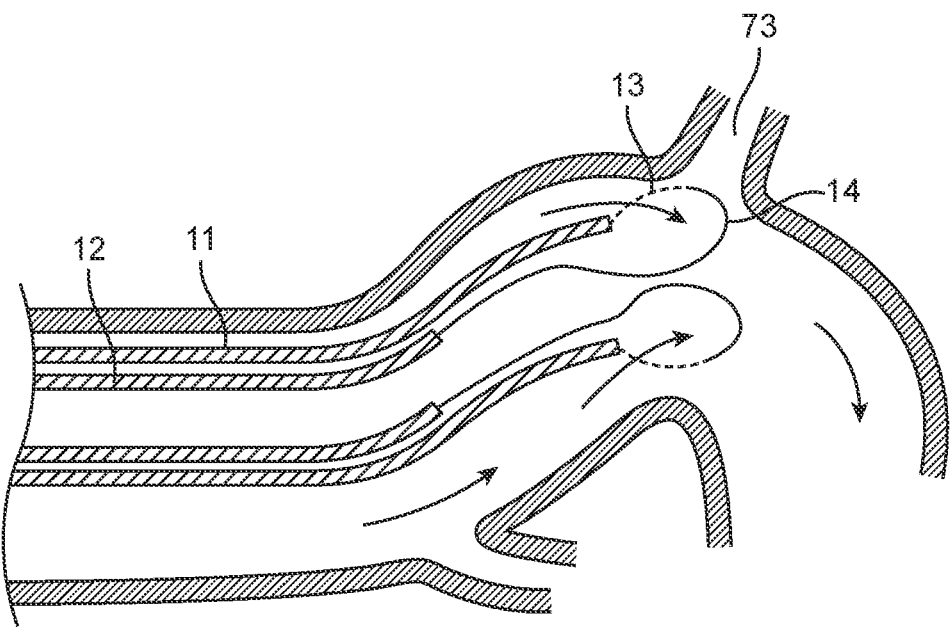
FIG. 8B shows a schematic of a device comprising an expandable element used for navigating a blood vessel, with the expandable element partially deployed and entraining some of the forward blood flow to urge the device forward without engaging in the orifice of a vessel side branch, in accordance with embodiments.
Figure 8C:
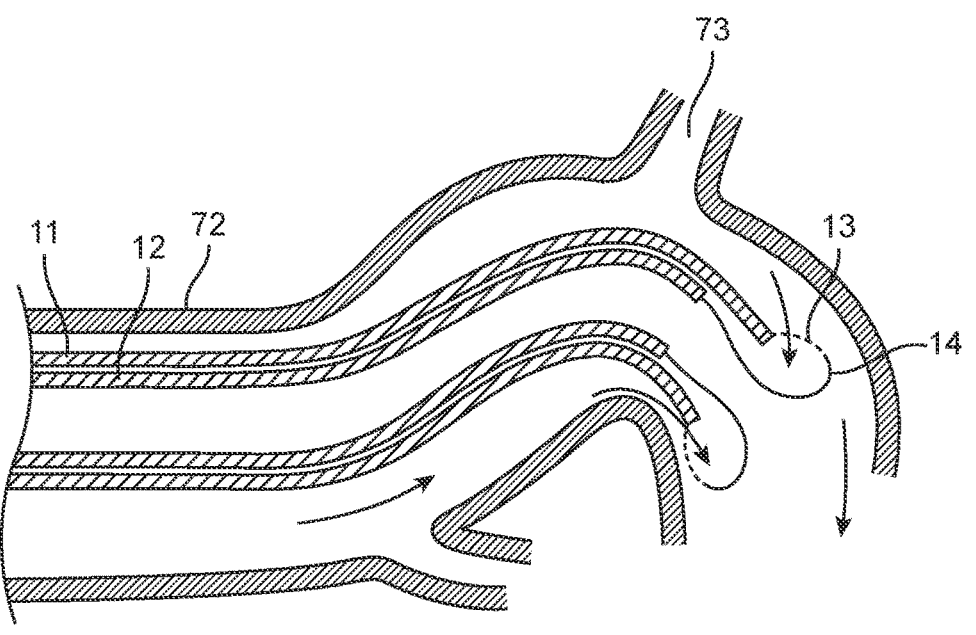
FIG. 8C shows a schematic of a device comprising an expandable element used for navigating a blood vessel, depicting further forward advancement of the distal catheter tip, in accordance with embodiments.

Another method of advancing a catheter-based device or system past a relative navigational tortuosity, obstruction, or hindrance comprises partially deploying the funnel to engage the forward blood flow in propelling the catheter tip forward as depicted in FIGS. 8A, 8B, and 8C. This action will slightly displace the tip from the vessel wall 9 and also capture the forward flowing blood 41 within the partially expanded non-permeable sections 14 of the braid prior to the braid anchoring or securing the distal tip to the blood vessel (e.g., by exerting an anchoring force 42 on a wall of the vessel in an outward radial direction). This action may be particularly useful in traversing the carotid siphon and other tortuous paths to the desired target site including traversing the right atrium and ventricle to access the pulmonary artery amongst others. Engaging the forward flowing blood to advance the catheter tip forward will require a portion of the non-porous segment 13 of the expandable element 61 to be marginally expanded and exposed to the blood flow 41 without expansion of the entire expandable element 61, an action which is not feasible with the braided expandable element positioned on the outer aspect of the inner shaft. In some cases, the expandable element can be marginally expanded so that only a short segment is expanded with the braid of the expandable element positioned on the inside of the outer shaft. With this configuration, the braid can be advanced out the end of the catheter-based device or system incrementally and create the configuration needed to capture the forward flow of blood 41 to urge the catheter forward without the added stiffness that would occur if the entire expandable element were expanded. Importantly, this configuration with the braid initially aligned within the outer shaft 11 is the optimal configuration for standard navigation.

To navigate tortuous vessels with standard catheters, it is advantageous to construct the catheter wall with enough flexibility to navigate the vessels while possessing enough longitudinal rigidity to push the catheter forward. This is commonly done by providing progressively softer durometer components within sections of the catheter shaft so that it becomes progressively more flexible towards its distal end. This provides the pushability and the flexibility necessary for standard catheters to access remote distal targets. In some cases, similar construction of the catheter shafts described herein may be utilized. However, since there are two shafts, there are additional options for catheter construction which are pertinent to embodiments of the present disclosure. These options include utilizing or varying different materials or combinations of materials in each shaft to optimize the pushability, flexibility, and other properties of the catheter-based device or system. For example, the outer shaft 11 may be constructed similar to a conventional catheter shaft with an adequate longitudinal rigidity combined with progressive flexibility so that the requirements for navigation are addressed. The inner or outer shaft of a catheter-based device or system described herein can be constructed of a single film cast tubing or extruded material without the components in the other shaft that provide longitudinal rigidity. This configuration, depicted in FIG. 9, permits a thinner and more flexible outer member 11 covering the flexible expandable element 13, 14 for maximum distal flexibility. The inner shaft 12 can be configured to have a longitudinal rigidity for pushability. The inner and outer shaft members are approximated to one another but not bound or fixed, thereby providing more flexibility with comparable outer and inner diameter single wall catheters. Simply, two coaxial tubes in this optimized configuration are stronger with greater longitudinal rigidity and pushability and more flexible than a single tubular structure for comparable internal and external diameters and will navigate tortuous vessels more easily and with less difficulty than existing devices.

Figure 9:
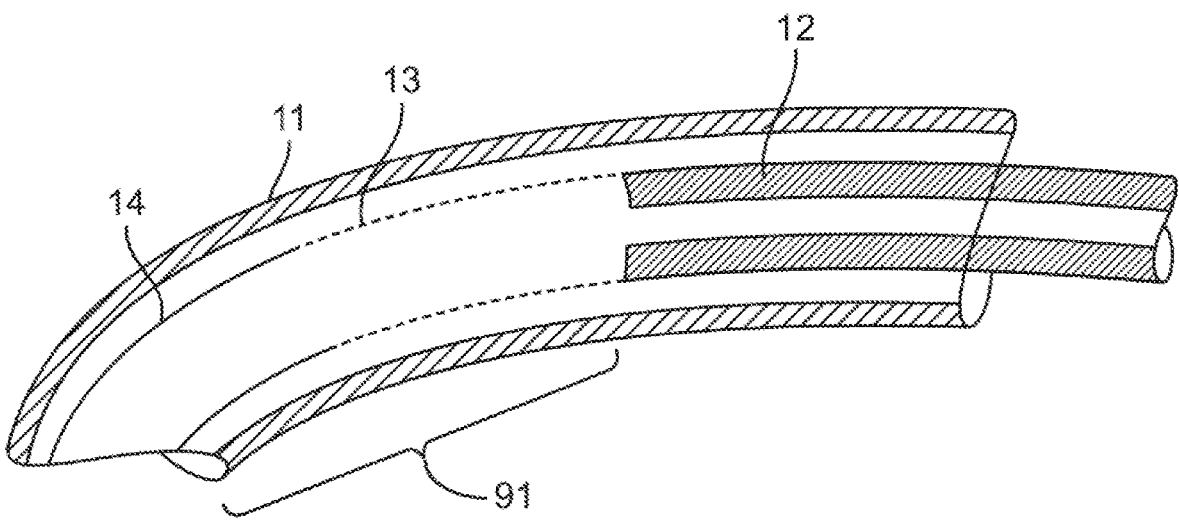
FIG. 9 shows a schematic of a device comprising an expandable element that is constructed to have improved flexibility, the device comprising a soft outer sheath positioned over the expandable element, in accordance with embodiments.

In a collapsed configuration of the catheter-based device or system as shown in FIG. 9, utilizing the most flexible shaft, whether the inner or outer, along with the section of braid 13,14 will cause the tip 91 of the catheter-based device or system 10 to be the most flexible. Hence, in the example above, the thin and flexible outer shaft 11 may be positioned coaxially over the braid apparatus 13.14 for maximum flexibility of the distal tip 91 of the catheter for navigation of tortuous vessels. This configuration places the two most flexible segments of the catheter, the thin flexible film cast outer shaft 11 and the braid 13,14, at the distal catheter tip 91 for maximum flexibility while maintaining the proximal stiffness and pushability of the catheter, which can be provided by the more robust inner catheter shaft 12 for longitudinal rigidity. This is another example of the benefit of the method allowing a practitioner to alternate the position of the braid in relation to the shafts to achieve maximum flexibility for navigation. In FIG. 9, the inner shaft 12 is the shaft constructed to provide longitudinal rigidity and the outer shaft 11 is a thin film cast tubing which is quite flexible. The braid segment 13,14 is attached to the distal end of the outer shaft 11 and occupies a position within the outer shaft 11. This causes the distal aspect of the device to be more flexible than standard catheter construction. The illustration reflects this flexibility with a slight downward curve that may occur if the catheter were placed in a horizontal orientation in air.

The distal end of a collapsed expandable element of a device or system described herein (e.g., a catheter-based device or system) can comprise the cylindrical tubular braid either positioned over the inner shaft 12 or covered by the outer shaft 11. In other words, in a collapsed configuration the catheter-based device or system's distal end can comprise one catheter shaft and the tubular braid rather than two catheter shafts. The braid configuration and size of filaments determines the flexibility and stiffness of this component of the catheter. A configuration which comprises a flexible filament and flexible braid configuration with variations of one or more of pics per inch, number of filaments, and heat setting the nitinol braid amongst other structural elements will further contribute to the flexibility of the distal catheter which will aid in the navigation of difficult vascular anatomy.

Further, there may be a need in certain instances to provide a means of occluding a vessel gradually so that the distal tissues accommodate to the lack of blood flow and the resulting ischemia. There may also be a need for restoring flow gradually to tissues that have been occluded several hours by thrombus or occluded for several minutes by the catheter-based device or system during an intervention. Utilizing balloon catheters can cause a latent period during the inflation/deflation of balloons between injecting or removing fluid from the balloon and the actual balloon inflation or deflation. Hence, the operator may not have precise control over the degree of partial occlusion or partial flow and as a result measured occlusion or measured reperfusion is not feasible with balloon occlusion catheters. However, utilizing a catheter-based device or system described herein, e.g., with the improvements regarding permeable and impermeable sections of the expandable element along with the ability to precisely partially or fully deploy the funnel to achieve variable levels of occlusion, a measured or graded occlusion and reperfusion can be accomplished.

The improvements in the funnel configuration and the improved methods above may also be utilized when multiple funnel catheters are utilized in one procedure. A method comprising utilizing multiple funnel catheters synchronously and coaxially can be useful in several applications of the devices and systems described herein. In the case of stroke intervention, there is a need to provide proximal flow arrest with a large internal diameter receiving catheter or guide catheter to support the advancement and distal navigation of a coaxially inserted distal aspiration catheter to remove thrombus, embolus and debris. This receiving/guide catheter may be a component of a catheter-based device or system described herein. These catheters are too large to advance intracranially to the middle cerebral artery so they must be positioned in the internal carotid artery, and the thrombus, embolus or debris transported to them by a smaller aspiration catheter or a stent retriever ("stentriever"). Engagement, retrieval, and transport of the thrombus by an aspiration catheter from the middle cerebral artery proximally to this larger receiving/guide catheter is best done with blood flow occluded so that the antegrade flow does not fragment the thrombus and cause additional iatrogenic emboli while retrieving and transporting the thrombus through the tortuous distal internal carotid artery to the receiving catheter. Proximal flow arrest during thrombus retrieval can be both safe and effective. Typically, balloon guide catheters are utilized to provide the flow arrest, but they can have several critical deficiencies and problems. One is that the cylindrical tip of the balloon guide catheter tends to core or plug the clot as it enters the opening at the catheter tip. This inhibits the passage of the thrombus into the catheter lumen and may further shear and fragment the clot and create potential emboli. Additionally, balloons are time consuming to prep, slow to inflate and deflate, and the inflation is imprecise. The inflation channel also causes the catheter to be stiffer than otherwise which frequently creates difficulty with navigating to and placing the catheter in a desired site especially in tortuous vessels which are quite common in the typical stroke age group. These deficiencies create difficulties with use significant enough to hinder their universal use despite their improved safety profile.

The current funnel catheter overcomes these deficiencies by providing a larger mouth for which the thrombus to enter or be retracted into more easily. The mouth of the funnel catheter may have a cross sectional area 3-6 times larger than the mouth of a standard catheter of the same shaft outer diameter. This prevents further fragmentation of the retrieved thrombus and obviates potential emboli while providing a greater suction force at the tip. The funnel is also deployed instantly vs. the delayed and imprecise action of balloon guide catheters.

One or more catheter-based devices or systems (e.g., comprising one or more funnel catheters described herein) can be used for stroke intervention. Such methods can comprise utilizing one or more funnel catheters concurrently to remove an occluding thrombus from the anterior and middle cerebral arteries and their immediate branches and from the vertebral-basilar system's major arteries and from other vessels throughout the body.

This may take the form of a flow arresting funnel guide catheter that is preferentially placed in the distal extracranial or intracranial internal carotid artery. In this instance, the flow arresting funnel guide catheter is utilized in the same manner as a balloon guide catheter, and the occlusion is created by the instant and atraumatic occlusion abilities of the funnel design rather than a balloon. Typically, a method of utilizing two funnel catheters within the same procedure for an anterior circulation stroke intervention comprises the flow arresting funnel guide catheter being inserted in a collapsed state via the femoral artery coaxially over a smaller selective catheter that is used to catheterize the right or left common carotid artery or the innominate artery. The flow arresting funnel guide catheter, with the expandable element collapsed, is then advanced over a guide wire or the selective catheter to a location in the internal carotid artery, the selective catheter is removed and replaced by a microcatheter and/or a navigable aspiration catheter that are used to access the target site in the proximal anterior or middle cerebral arteries. The flow arresting funnel guide catheter (e.g., with the expandable element expanded or deployed into an expanded configuration) supports the advancement of the microcatheter and aspiration catheter through the tortuous carotid siphon to the target site with its centering and anchoring functions. The instant funnel guide catheter provides stability at or near the tip of the catheter from the expanded funnel. Standard non-balloon guide catheters have no such means of providing stability near the tip for support of coaxially inserted catheters to be advanced distally to the target site. Balloon guide catheters may provide a small amount of distal support, but the smooth surface of the balloons causes the catheter to slip as the balloons do not consistently provide stability. At the target site (e.g., the target site comprising a material to be removed, such as a thrombus, and/or a location of the blood vessel at which the material is located), the method may further comprise a stent retriever ("stentriever") being inserted and passed into or distal to the thrombus to provide traction on the thrombus to pull it to, into, and through the length of the flow arresting funnel guide catheter to remove it. Instead of a stent retriever, the method may comprise advancing the aspiration catheter to a point near or contacting the clot face, suction may be applied to the thrombus via the aspiration catheter and the thrombus retracted while suction is applied to the aspiration catheter with an aspiration syringe or suction pump. As well, these two methods or some variation of them, may be used together or synchronously to engage the thrombus and transport it proximally to the flow arresting funnel guide catheter for removal. Preferably, the flow arresting funnel guide catheter dimensions will be an outer dimension of 8 Fr. (e.g., 8 French), an inner diameter of approximately 0.087 inches and 100 cm in length, although other dimensions may be utilized.

In the case of utilizing two funnel catheters together, the flow arresting funnel guide catheter may be utilized as above with any aspiration catheter. However, the aspiration catheter may also be a funnel catheter sized to fit within the internal dimensions of the flow arresting funnel guide catheter. Preferable dimensions of the funnel aspiration catheter are 0.083" (e.g., 0.083 inches) outer diameter, 0.061-0.070 inches inner diameter and 120 cm in length, although these dimensions may vary. For example, an outer diameter of the funnel aspiration catheter can be from about 0.070 inches (in.) to about 0.075 in., from about 0.080 in. to about 0.085 in, from about 0.085 in. to about 0.090 in. In some cases, an inner diameter of a funnel aspiration catheter can be from about 0.050 in. to about 0.060 in., from about 0.060 in. to about 0.070 in, from about 0.070 in. to about 0.080 in. In some cases, a length of a funnel aspiration catheter can be from about 80 centimeters (cm) to about 100 cm, from about 100 cm to about 120 cm, from about 120 cm to about 140 cm. In some cases, a method of utilizing two funnel catheters can follow the method described above, for example, with the modification that an aspiration funnel catheter described herein would be placed through the flow arresting funnel guide catheter instead of utilizing the standard aspiration catheter. After advancing the aspiration funnel catheter to the target site adjacent to the face of the thrombus, the funnel is deployed and the target vessel containing the clot is occluded by the expansion of the funnel catheter, aided with the patient's blood pressure. Suction is then utilized in the aspiration funnel catheter via an aspiration syringe or pump. Because of the unique properties of the aspiration funnel catheter, the thrombus will be elongated as the thrombus is pulled into the tapered funnel and the catheter shaft by suction. This elongation will narrow the thrombus diameter which will at least partially detach it from the vessel wall and overcome the existing friction between the thrombus and the vessel wall. This can make the thrombus aspiration much easier than standard aspiration catheters as they tend to plug or core the thrombus upon applying suction as the aperture in the end of the standard aspiration catheter is much smaller than the thrombus. Moreover, the standard aspiration catheters attach themselves to the clot by coring or plugging the clot by suction rather than completely aspirating and removing it in most cases. They then must be withdrawn retrograde through the tortuous carotid siphon and into guide catheter with much of the thrombus trailing behind for removal. This dramatically increases the potential for unintended embolic particles to be sheared off the trailing thrombus during this retraction process by the blood flow, contact with the vessel wall, or a combination of both. Utilizing the aspiration funnel catheter would obviate this situation as all of the thrombus will be aspirated completely in almost all cases. In the instance in which the thrombus is only partially aspirated, the flow arresting funnel guide catheter may be utilized to provide proximal embolic protective flow arrest during the retraction process with the funnel catheter to insure there are no emboli liberated. A preferred method may be to utilize the flow arresting funnel guide catheter in a flow arrest state during the entire engagement, aspiration, and retrieval process by the aspiration funnel catheter routinely rather than only if the thrombus is not completely aspirated.

The aspiration funnel catheter may also be utilized with a stentriever to deploy the stentrievers and retract the stentrievers into the aspiration funnel catheter completely or at least partially before it is retracted into the flow arresting funnel guide catheter. The protective flow arrest at the clot face will prevent distal migration of the fragments of thrombus created during the passage of the stentriever through the thrombus and the expansion of the stentriever within the thrombus, and provide for aspiration of these fragments during retrieval of the thrombus into the aspiration catheter before they can embolize downstream. In this instance flow arrest or blood flow occlusion by the flow arresting funnel guide catheter may be utilized during one or more or all of accessing the clot, engaging the clot, retracting the clot, ingesting the clot, removal of the clot from the funnel guide catheter, and after removal of the clot to establish flow reversal in the internal carotid artery and other cerebral vessels to collect micro-emboli that may have been liberated during this process and not completely retrieved during the aspiration phase.

The aspiration funnel catheter may also utilize small apertures in the distal internal shaft or in the funnel with suction to both fragment the surface of the thrombus and provide a fluid assist to facilitate the passage of thrombus from the funnel through the catheter shaft and into the syringe or suction pump. This feature may be activated by the user as has been previously described.

The First Pass Effect is a term utilized to describe the removal of the entire clot from a large cerebral vessel on the first pass or first try as the resulting clinical disabilities and deficits are much lower and clinical outcomes are much better. The factors which preclude a first pass success are clot fragmentation, incomplete clot removal, impaction friction, friction between the clot and the vessel wall, ingestion friction between the clot and the catheter tip including corking of the clot on the catheter tip, ingestion friction into the larger guide catheter, and distal embolization of fragments that may be liberated because of any or all of the above. These result in poorer outcomes that are a direct result of one or more of the above problems. First Pass Success is achieved in less than 50% of cases of stroke intervention. Hence, there is a need for devices, systems, and methods of improved clot removal that overcome the problems of the current retrieval devices including clot fragmentation, an increase in friction between the clot and the vessel, potential embolization of fragments, incomplete clot removal, and less than optimal outcomes amongst others, so that first pass success is achieved more consistently, and better clinical outcomes with less disability is a result. An object of various embodiments of methods, devices, and systems described herein is to overcome the above problems with the instant system and method described herein and to achieve first pass success and a First Pass Effect in a much larger per centage of patients with devices, methods, and systems which address those problems.

Typically, the large vessel occlusion which causes the stroke is from a thrombus that embolizes either from the left atrium or from atherosclerosis near the carotid bifurcation to the middle cerebral artery. This thrombus or clot frequently has variable mixed components of red blood cells and fibrin components depending on multiple factors such as the length of time the clot was present before embolization occurred. The clot may be predominately "red" clot with a preponderance of loosely aggregated red blood cells or "white" clot with a preponderance of fibrin components, but usually the clot is a combination of both elements.

White clot may be more difficult to remove with aspiration as it may not be as compressible as red clot and it does have a higher coefficient of static friction. Stent retrievers may not insinuate into this firmer clot and may cause increased friction to prevent retrieval.

Predominantly red clot is easier to remove with aspiration, but suction may not be able to hold onto or secure the tail end because of friction/adhesion and the systemic blood pressure especially without proximal flow arrest. In other words, with systemic blood pressure impacting the face of the clot without any protective flow arrest or proximal occlusion, the impaction force essentially packs the clot into the vessel more tightly and makes the clot more difficult to remove. This also increases the friction between the clot and the vessel wall irrespective of the clot consistency.

It is easier to insinuate a stent retriever into red clot and there will be less transfer of forces to wall to increase friction than with white clot, but the stent retriever may fragment the softer and more friable clot. It is well known that a stent retriever hardly ever captures and contains the entire clot.

The white component of clot (fibrin, etc.) is more dominant from embolic sources in which the clot has matured somewhat and then embolized. The larger the original clot at the embolic source, the more white clot can be expected in the middle cerebral artery or other large vessel embolus. The amount of white clot can be dependent on the age (and other considerations) of the original clot as well as how much acute clot is attached to the older clot when the embolus occurs.

Hence, the embolus will likely be a mixed consistency and this variation cannot be reliably predicted yet (although it is possible to get some idea from CT/MRI evaluation of occluding thrombus). Therefore, an optimized clot retrieval system must address all consistencies equally well since the type and consistency of clot will be unknown or unclear at time of presentation.

When the thrombus embolizes, it lodges in the middle cerebral artery with an impaction force of the systemic blood pressure and occludes flow to that watershed portion of the brain supplied by that artery, including the motor and sensory areas which are responsible for normal functioning. These areas have been termed "eloquent brain" as damage to these areas will result in disability.

Removing the clot will demand overcoming the impaction force that has wedged the clot into the MCA, overcoming the friction between the clot and the vessel wall, and overcoming the adhesions that may develop between the clot and the vessel wall. If these actions are not achieved, the clot may be resistant to removal and likely will be fragmented or incompletely removed on the first pass or first attempt.

In some cases, a catheter-based device or system described herein can be used to address and solve these and other issues which may prevent the complete removal of the clot on the first pass. One method that is feasible with the catheter-based devices and systems (e.g., aspiration funnel catheter) described herein and not with other catheters and devices is to mobilize the clot and overcome the impaction force, friction, and adhesion issues and to lessen the firmness or consistency of the clot so that it is more easily aspirated. This method comprises occluding the flow of blood just proximal to the clot with the current aspiration funnel catheter which protects the clot face and the clot from the impaction forces of the systemic blood pressure, and then providing a means that uses a frequency, a combination of frequencies, changes in pressures (including suction) or other means to create hydraulic or other forces that will oscillate the clot to an extent that it is more easily mobilized from the vessel wall. The means may be a variation in suction intensity in alternating "pulses" or cycles of fractions of a second to several seconds in length and may comprise one or more of the following: 1) varying or alternating the suction, 2) sound or pressure waves generated by a coaxially inserted catheter through the instant aspiration funnel catheter, 3) low frequency waves or specific pressures and timing delivered through the lumen of a catheter-based device or system described herein to disassociate the fibrin and other bands, 4) a simple motion of the funnel catheter in the deployment and un-deployment actions, or 5) other methods of generating forces that affect or move the clot. A preferred method of mobilizing the clot from the vessel wall may comprise exerting a gradually increasing suction via the deployed funnel of the aspiration funnel catheter and suddenly releasing the suction. This may be repeated several times and may be repeated manually or with prescribed intervals and suction levels by a programed suction pump. By gradually increasing the suction in the aspiration funnel catheter, the proximal clot will gradually elongate or stretch. When suction is abruptly discontinued, the clot will rebound or recoil distally where the presence of blood from collateral circulation will create a secondary and smaller amplitude recoil or rebound proximally. This action (e.g., oscillating action) may be repeated several times. The back-and-forth movement of the clot will tend to disassociate it from the vessel wall and overcome the impaction force, friction, and adhesion forces in addition to loosening of the visco-elastic bonds between the clot and blood vessel. It may also affect the internal organization of the clot to cause it to be more liquid and more easily aspirated through the aspiration funnel catheter. After one or more of these actions is accomplished, suction is then applied which may comprise a gradual increase in suction that will lengthen the proximal aspect of the thrombus and tend to tease the clot away from the vessel wall as the clot elongates with gradually increasing suction. This method overcomes those issues which have prevented existing devices and methods of achieving a successful first pass success. Simply, the combination of the protective flow arrest immediately proximal to the clot will isolate the clot from impaction forces, provide a greater suction force, overcome the friction issues between the clot and the vessel wall, and allow the clot to be aspirated more completely, without fragmentation, and without leaving portions of the clot behind all with a greater ease of ingestion through the mouth which is several times larger than the mouth of a conventional catheter.

The funnel or conical shape of the aspiration funnel catheter is optimal for transmitting suction, sound, or other pressure waves distally and into the clot. Hence, not only can the clot be oscillated to loosen the friction and adhesion at the clot and vessel wall interface, but also diminish the fibrin banding and other components may be that allow the clot to become more easily aspirated through the aspiration funnel catheter. The combination of loosening the friction/adhesion and lessening the clot consistency will result in a higher percentage of first pass success and better clinical outcomes if aspirated through a catheter that offers proximal protective flow arrest along with the advantages of the preceding paragraph.

The variations in suction or other maneuvers may be accomplished manually with manipulation of a standard suction syringe or by a suction machine programmed to exert suction for a specified period of time followed by a sudden or abruptly diminished suction. Preferably suction would increase gradually, then the suction would be abruptly released or diminished. Several series of these actions may be accomplished in a preferred embodiment of the method.

Alternatively, similar methods may comprise one or more of the following in removing a thrombus or embolus from a body vessel after deploying the funnel and occluding the vessel near the clot face: injecting contrast, medicaments, or other fluids after occlusion, for example, to help dissect the clot prior to suction, to relax and dilate the vessel, and to dissolve the clot or limit the adhesion of the clot to the vessel wall amongst other actions; pulsing (e.g., small volume) contrast injections or other fluids and alternate with suction to loosen the clot; applying a negative pressure (e.g., applying suction gradually to tease the clot away from the wall of the vessel); and/or increasing the suction (e.g., gradually) so as to elongate the central portion of the clot face so that the edges of the clot that abut the vessel wall are pulled away from the wall while being pulled forward will enhance clot mobilization, which can be distinctly different than clot retrieval by standard aspiration catheters which rely upon excessive suction.

Actively deploying and undeploying (e.g., retracting) the funnel of the expandable element can cause some hydraulic pressure changes within the clot which can cause the clot to be more easily mobilized, for example, by diminishing the friction and the adhesion of the clot to the vessel wall.

The adhesion issue must be overcome in addition to the friction that limits aspiration. The jostling of the clot by the suction alternating with at least the partial deployment and undeployment of the funnel while either providing suction or pulsing/cycling the suction will assist in overcoming the adhesion of the clot to the vessel wall, if any, as well as loosening the clot with respect to the vessel wall. Hence, subsequent continuous suction or a gradually increasing cycles of varying suction levels that may have different pulsed temporal increments of suction from no pulse at all to pulses from fractions of a second to several seconds or minutes may be utilized to partially mobilize the clot. The method may also vary the intensity of the suction. For example, the method comprises placing a funnel catheter of the current invention adjacent to the face of the clot to be removed, deploying the funnel thereby occluding the vessel, and performing one or more or all of the following actions: Providing a suction that gradually increases in intensity, Providing a suction that varies in intensity, Providing a suction that varies temporally, and/or Providing a means of varying or alternating pressures which mobilize the clot and change the consistency of the clot so that it is more easily aspirated.

In some cases, a method described herein, such as the above method, may also be combined with other methods described herein. For example, a method can comprise the use of a thrombolytic agent, such as r-tPA. The r-tPA may be administered before the thrombectomy procedure (which is the standard of care currently) and can cause the clot to become somewhat more liquid or loosely organized and easier to aspirate but also easier to fragment and, in some cases, may result in the clot being incompletely removed or embolize during aspiration by current straw-like catheters. In some cases, the protective flow arrest of the instant aspiration funnel catheter and/or friction reducing measures described herein, a more liquid clot can be more easily aspirated completely. The protective flow arrest can protect against upstream blood flow and can mitigate the friction that may cause fragmentation associated with the aspiration of more loosely organized thrombus by standard straw-like catheters. Hence, the benefits of r-tPA and other lytics can be realized using various embodiments of devices, systems, and methods described herein without the deleterious fragmentation issues associated with standard catheters.

Moreover, because of the protective flow arrest, r-tPA or other lytics may be injected directly through a lumen of a catheter-based device or system described herein to bathe the clot immediately prior to, during, or after the thrombus aspiration as the protective flow arrest will isolate the clot from systemic blood. The lytic may be aspirated before, during, or after the thrombus aspiration if desired.

The thrombus that occurs in stroke is different than the thrombus which occurs typically with an acute myocardial infarction (AMI) as the thrombus in stroke is usually an embolus whereas the thrombus which occurs in AMI usually is from a local event such as rupture of a plaque. The clot in an AMI will consist of more red blood cell components and hence be more easily aspirated. The technique and method of removing an acute clot from a coronary artery hence is usually simpler as aspiration alone will be adequate to remove the majority of the clot. Embolic particles which are generated from this effort are not as critical as the myocardial muscular tissue that may be damaged or killed by procedural emboli will frequently not be enough to cause a disability as the remaining cardiac muscle will accommodate this loss of muscle. While there may be some diminished function, the diminished function can be addressed with supportive medications and lifestyle changes frequently. Moreover, the body's inherent thrombolytic mechanism along with the "fresh" nature of the clot will cause emboli that do occur to be lysed at least partially thereby frequently limiting the long-term effect of those emboli.

This is not the case in stroke where certain "eloquent" portions of the brain control specific individualized functions. It is critical to protect these areas from procedural embolic events which may damage these eloquent areas and cause disabilities. Hence, the techniques and methods to be used in thrombectomy, embolectomy, and clot retrieval in stroke must differ and include additional maneuvers and methods not typically present or utilized with thrombectomy, embolectomy, and clot retrieval in acute myocardial infarction and other thrombotic occlusions. In some cases, methods, techniques, and maneuvers described herein can ensure a clot is retrieved completely and safely despite these considerations.

Stroke intervention therapy has evolved into three or so methods of removing the thrombus. A summary of these methods is described below so that the current problems of these methods can be compared to the proposed novel methods contained herein which solve many of the problems of the existing methods. These current methods consist of Contact Aspiration Thrombectomy (CAT), stent retrievers to engage and remove (Stentrievers), and some combinations of both (Hybrid approaches).

In CAT, a guide catheter is usually placed in the internal carotid artery and an aspiration catheter is placed coaxially over a smaller guide wire and microcatheter to a position just adjacent to the clot face. The aspiration catheter is a relatively large bore catheter (e.g., having an inner diameter of from about 0.060 inches to about 0.074 inches) that is trackable or navigable through the tortuous carotid siphon. Suction and exaggerated suction is utilized to either aspirate all of the clot, or more commonly, to attach the aspiration catheter to the clot by suction for subsequent withdrawal into the larger guide catheter. While this technique is convenient for the operator because of the relative ease of navigability of the catheter, this method fails to achieve first pass removal of the clot in >50% of the cases and has worse clinical outcomes for several reasons including:

Most CAT cases do not use proximal protective flow arrest which creates a situation in which the clot is being retracted against forward flowing blood.

Most of the thrombus/embolus is not completely aspirated within the aspiration catheter shaft but only partially aspirated with most of the clot attached to its tip by suction essentially trailing the distal catheter tip during withdrawal. This is a recipe for embolic debris especially if the catheter and clot are withdrawn in flowing blood.

Suction secures only the proximal portion of the clot, but not the distal aspect. If the clot is friable, the proximal portion may become detached from the distal aspect during the removal leaving a portion of the clot in the MCA. This will demand a second or third pass to remove, possibly with additional suction efforts or insertion of a bailout stentriever. It is not feasible to determine prospectively which patients will have a clot that will be removed by CAT suction and which ones will be resistant to that method.

The degree of friction, wall adhesion and the impaction force of the clot will vary between patients which contribute to the relative "stickiness" of the clot and the difficulty in removing it. Aspiration alone simply cannot consistently overcome these forces without separating the proximal portion from other portions of the clot given the mixed and inhomogeneous consistencies of most clots.

The CAT suction method without proximal flow arrest and transport of the clot from the middle cerebral artery to the larger guide catheter invites and results in embolization and shearing of the non-contained clot projecting from the tip of the aspiration catheter upon ingestion into the guide catheter.

Many scientific studies have demonstrated outcomes for CAT which are inferior to other methods in the aggregate of cases despite convenience and success in a minority of cases.

Hence there is a need for improvement in the CAT or aspiration method of stroke intervention.

The use of stentrievers as a first line therapy in stroke intervention also has problems and challenges that create difficulties in achieving removal of the entire thrombus with the initial or first pass.

In utilizing an aspiration funnel catheter (e.g., of a catheter-based device or system described herein) to remove thrombus or other material from the vasculature, suction may be augmented by traction on the thrombus or material to be removed with stentriever devices known in the art or with a novel traction device. While removal of thrombus from some locations may be performed with a variety of configurations of a clot retractor, some locations, such as removal of thrombus from the larger vessels of the brain, may demand special considerations to ensure the thrombus or clot retractor does not cause unintended side effects or consequences. In the case of stroke intervention, various clot retractors or "stentrievers" have been used for more than a decade. Many of these are designed to insinuate the stent like device into the clot so that it can be removed. This insinuation may, however, cause the clot to be fragmented as the components of the device insinuate themselves into the clot. This fragmentation increases the chances of unintended embolization of these fragments when the clot is retracted into a receiving or removal catheter, particularly if the patient had been administered r-tPA causing the clot to be less organized and more friable. This is a significant downside of utilizing the current generation of stent like clot retrievers in stroke intervention.

Another disadvantage of existing stentrievers and stent like clot retrievers is that upon insertion of the device (usually delivered by a microcatheter) through the clot and the subsequent expansion of the device within the clot, the friction between the clot and the arterial wall in increased as the stent like device expands. Typically, the stent like clot retractor device or stentriever is inserted coaxially within a microcatheter through the clot so that a significant portion of the device is positioned within the clot. The stentriever is placed eccentrically through the clot as there is no centering mechanism. The microcatheter is then typically withdrawn or removed which allows the self-expanding stent like clot retractor to expand and insinuate itself within the clot for several minutes. As the stentriever expands within the clot, it creates added pressure between the clot and the vessel wall which increases the friction between the clot and the vessel wall. The increase in friction that occurs because of the expansion of the stentriever is obviously detrimental to removing the clot as the clot "swells" from the expanding device within it. The increase in friction makes it more difficult to remove all of the clot as the combination of the fragmentation caused by the retraction device and the added friction makes it more likely that portions of the clot may disassociate from the larger body of the clot and not be removed. This often prevents a "first pass success" or removal of all of the clot with the first pass, an important metric directly associated with significantly improved outcomes and less disability. The inability to remove all of the clot the on the first pass may require multiple passes and attempts at complete clot removal, which has been shown to result in greater disability and significantly worse clinical outcomes.

Additionally, the eccentric placement of the stentriever may cause it to impinge on the arterial wall when it expands. This may cause local vasospasm which may increase the pressure and friction in some cases.

The expansion of the stentriever also weakens the clot consistency and structure (fibrin bands, etc.) and makes the clot more friable and more likely to create embolic particles if it is retrieved without proximal protective flow arrest. Hence, most stentriever procedures are utilized with proximal flow arrest even when used concurrently with adjunctive suction.

The typical stentriever is delivered through a microcatheter as discussed above which has an outer dimension of approximately 3 French (Fr.) or about 0.039 inches. Particle embolization from piercing the clot with this catheter/wire combination is almost certain to occur with standard stentriever delivery as antegrade blood flow is likely to cause particle embolization when the clot is crossed with the stentriever. This is even likely if proximal flow arrest in the internal carotid artery is provided by a balloon guide catheter or a non-balloon protective flow arrest catheter, although much less likely. Collateral flow via the anterior or posterior communicating arteries will provide some antegrade flow which has the potential of washing small fragments downstream. This almost certainly occurs but may not be recognized as subtle embolization cannot be differentiated from the changes in the brain on CT and MRI scans caused by the large vessel occlusion which prompted the procedural intervention. With the aspiration funnel catheter (e.g., of a catheter-based device or system described herein), antegrade blood flow is occluded at the clot face creating a static work environment in which to pass either a typical stentriever or the clot retractor of a device or system described herein through the clot. Any small particles that may be dislodged do not embolize distally as there is no head pressure or potential micro flow channels along the stentriever channel to do so as the occlusion by the aspiration funnel catheter prevents embolization. Moreover, an aspiration funnel catheter of the current invention centers the stentriever for passage through the clot which tends to prevent eccentric placement of the stentriever that is likely with standard aspiration catheters. In some cases, insertion of the clot retractor of some embodiments of the devices and systems described herein instead of a typical clot retractor would offer several advantages including the need for a microcatheter to be inserted through the clot. The smaller size of the current clot retractor (e.g., 0.027 inches outer diameter ("OD")) is another advantage.

In some cases, stentrievers are not preferred, for example in that their use can require placement of an additional device, their use can take several minutes to expand, they can create added friction inhibiting the ease of clot removal, and they may fragment the clot while not containing all of the fragmented clot material, which may predispose some embodiments of procedures using the device to unintended embolization during passage of the stentriever through the clot, upon transit from the MCA to the larger guide catheter, and ingestion into the larger guide catheter.

Because of the foregoing issues with CAT and Stentriever thrombectomy, "hybrid" techniques have evolved which use a combination of suction by an aspiration catheter and insinuation and traction with a stentriever with retrieval into a larger guide catheter more proximally. These techniques may have improved technical success and disabilities somewhat, but still present several problems and issues that can be solved with using devices and methods of the current invention.

Many of the methods or techniques disclosed herein may be utilized alone or in various combinations with all or portions of other methods or techniques to create hybrid approaches to safely and completely removing the thrombus on the first pass. As well, these various techniques may be utilized in a stepwise fashion so that the interventional effort is increased if the need arises. In other words, if the simple maneuvers are not successful, adjunctive maneuvers may be easily added that avoid catheter exchanges and other maneuvers which may be both time consuming and relatively risky to the patient.

One method or approach may comprise placing the aspiration funnel catheter just proximal to the clot in the MCA, deploying the occluding funnel, and providing a gradually increasing suction to the clot. This action alone may be sufficient to remove all the clot without any further maneuvers. If clot remains after the initial maneuver, adjunctive measures such as applying pressure waves to the clot to mobilize it may be undertaken followed by gradually increasing aspiration while continuing the protective flow arrest occlusion. Alternatively, this adjunctive maneuver may be employed initially to mobilize the thrombus prior to the initial aspiration.

If these efforts are not successful at removing all the thrombus, then a clot retractor may be inserted through the occluding aspiration funnel catheter and distal to the thrombus in a collapsed or undeployed configuration. The basket or expandable portion of the instant clot retractor may then be expanded, and gentle, gradual traction exerted on the distal aspect of the thrombus to urge it forward while applying gradually increasing suction through the aspiration funnel catheter. Tactile feedback on the traction of the instant clot retractor along with visual evidence of clot being aspirated will signal the operator as to whether the clot is a consistency which may be completely aspirated through the aspiration funnel catheter or whether there may be firm or fibrinous components which prevent it from entering and traversing the catheter shaft. If there is resistance to traction or no clot in the external suction collection apparatus, the operator may then "pin" the clot between the expanded occluding funnel proximally and the expanded clot retractor distally and retract the aspiration funnel catheter, the clot retractor, and the clot into the larger guide catheter more proximally positioned in the internal carotid artery for complete removal. Hence, a stepwise method of using various maneuvers as needed will simplify the approach to all stroke cases with a single placement of an aspiration catheter (e.g., of catheter-based device or system disclosed herein) and avoid the repeated passes necessary for difficult cases and obviate the clinical disabilities associated with multiple repeated passes.

Alternatively, a stent retriever or a clot retractor device may be used primarily with the aspiration funnel catheter using the method above. This method may comprise placing the aspiration funnel catheter at the clot face, expanding the expandable element to provide protective flow arrest, passing one of a stentriever or a clot retractor either to a point within or distal to the clot, expanding the stentriever or clot retractor, and providing traction with the stentriever or clot retractor to pull the clot into the funnel mouth and catheter shaft and through the catheter shaft. Suction may also be provided prior to, during, and/or after the traction.

Figure 10A:
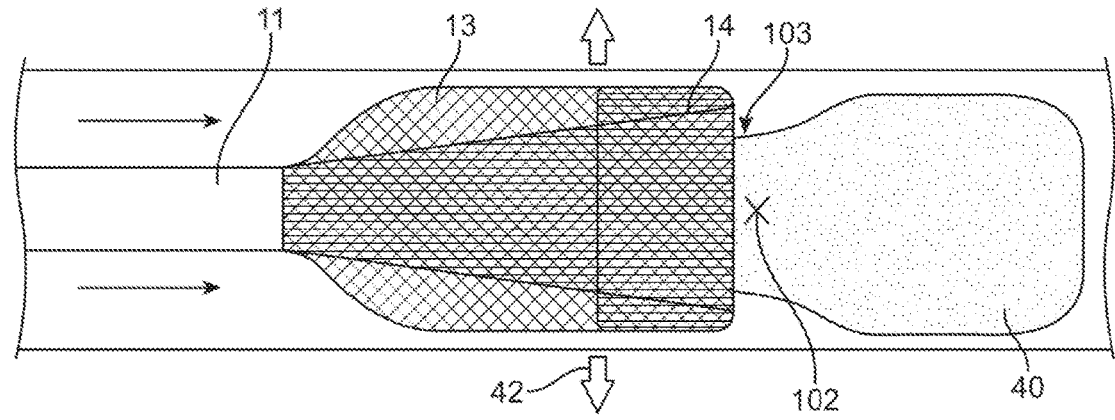
FIG. 10A shows a schematic of a device comprising an expandable element for removing material from a vessel lumen by intake of the material into the funnel shaped mouth of the expanded expandable element, in accordance with embodiments.
Figure 10B:
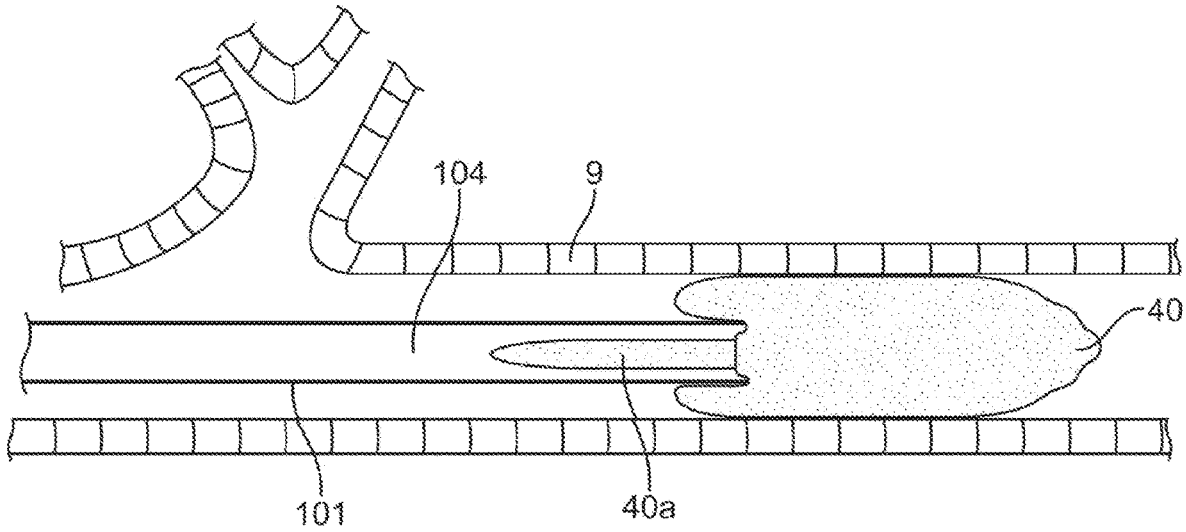
FIG. 10B shows a schematic of a straw catheter device for removing material from a vessel lumen during thrombus aspiration, in accordance with embodiments.

FIG. 10A demonstrates the advantage of an expanded expandable element to more easily ingest a clot than a standard catheter as is shown in FIG. 10B. The large mouth 103 of the funnel catheter 10 of FIG. 10A readily ingests the clot face 102 and the clot body 40 with little resistance or friction. The standard catheter 101, depicted in FIG. 10B, however, aspirates some of the clot 40 but tends to "cork," or core the clot 40 as portions of the face 40a of the clot 40 are sucked into the lumen 104 because of the straw like configuration of the tip. This prevents the easy ingress of the clot 40 into the catheter 101 and is a primary reason that the entire clot 40 cannot be aspirated on the first pass. While the proximal portion 40a of the clot 40 may be aspirated, the distal portion may separate creating one or more fragments that may either remain in place in the artery 9 or embolize distally when the catheter is withdrawn towards the guide catheter for removal. These problems are obviated by the funnel catheter in FIG. 10A.

Figure 11:
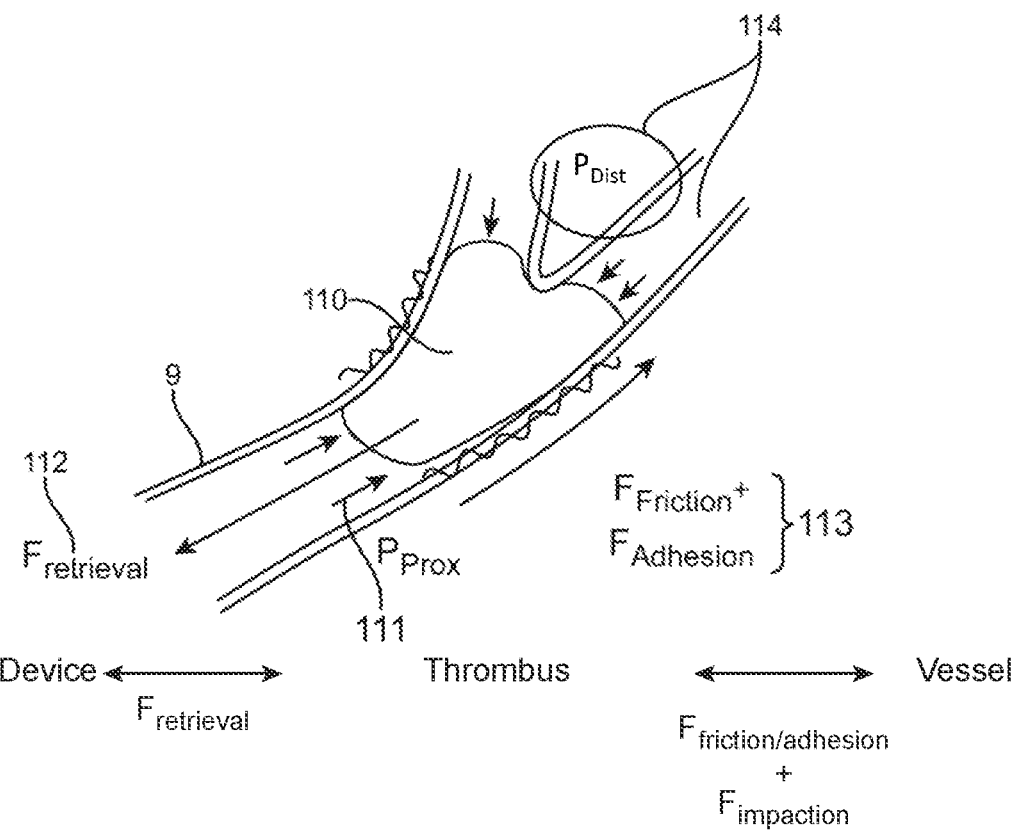
FIG. 11 shows a diagram of forces exerted on a vascular obstruction, in accordance with embodiments.

FIG. 11 represents a diagram of forces exerted on a clot in the middle cerebral artery. $P_{Prox}$ 111 is the force of blood pressure on the face of the clot impacting it into the artery and creating impaction friction or $F_{Impaction}$ 110. This contributes partially to the friction between the clot and vessel wall $F_{Friction}$, which is combined with the visco-elastic bonds and adherence of the clot to vessel wall $F_{Adhesion}$ to increase the overall friction between the clot and vessel wall represented as $F_{Friction} + F_{Adhesion}$ (113). Hence, the overall friction between the clot and vessel wall is due to $F_{Friction} + F_{Adhesion} + F_{Impaction}$. All three components contribute to the retrieval friction, $F_{retrieval}$ (112), which inhibits the ingestion of the clot into the aspiration catheter. These factors can be at least partially responsible for the fragmentation of the clot during retrieval efforts with existing devices with either stentrievers, aspiration thrombectomy without stentrievers, or a hybrid approach utilizing both methods. In some cases, overcoming the friction between the clot and the vessel wall as described herein can improve retrieval of material from a vessel.

Moreover, the retrieval friction generated by standard retrieval catheters is a significant barrier to successful ingestion of the clot into the aspiration catheter. Standard cylindrical catheter tips are smaller than the clot being retrieved, frequently causing the clot to become "plugged" or "corked" on the end of the aspiration catheter as demonstrated in FIG. 10B. In these instances, the aspiration catheter, with some of the clot being partially aspirated into the catheter lumen and a large portion of the clot projecting out from the catheter tip, must be withdrawn into a larger guide catheter through a tortuous distal internal carotid artery to a more proximal location. This is frequently done without proximal flow arrest, which significantly enhances the chance of distal embolization of the tail of the clot while it is being withdrawn towards and into the guide catheter.

As previously shown in FIG. 10A, embodiments of catheter-based devices and methods described herein with the large funnel mouth of the funnel catheter can overcome both the clot/vessel friction and the clot/aspiration catheter friction issues which inhibit a successful embolectomy or thrombectomy with no fragmentation or emboli that frequently occurs with the current methods of clot retrieval.

Various embodiments methods of the current disclosure, which can be useful for overcoming the friction issues of clot retrieval, can comprise placing the instant funnel catheter tip adjacent to the clot face, and expanding the funnel to cover the clot face to eliminate the impaction friction on the face of the clot, eliminate the blood pressure effect on the face of the clot, employing maneuvers previously described herein to loosen the clot-vessel friction, and aspirating the clot into the instant funnel catheter with the assistance of retrograde pressure on the distal aspect of the clot from collateral blood flow. This can isolate the clot from systemic blood pressure and the $P_{Prox}$ 111 and $F_{Impaction}$ 110 forces of FIG. 11. Additionally, the impacting blood pressure effect that may be transmitted through upstream collaterals (via anterior and posterior communicating arteries, in the case of a middle cerebral clot) is also eliminated by proximal flow arrest immediately adjacent to the clot face even if proximal flow arrest is provided in a location proximal to these upstream collaterals by a balloon guide or other guide catheter more proximally positioned in the internal carotid artery, as is usually the case. After deployment of the funnel to cover the clot face, methods are described below which may cause micro movements of the clot may be employed which will lessen the $F_{Friction}$+$F_{Adhesion}$ forces 113 and loosen the friction between the clot and vessel wall. Additionally, traction may be provided on the distal aspect of the clot by a clot retractor.

Since the suction force is proportional to the cross-sectional area of the catheter tip, the large mouth of the funnel will dramatically increase the suction force over conventional cylindrical tip catheters. For example, in the middle cerebral artery, the instant funnel catheter tip has a cross-sectional area approximately 2.6 times greater than a conventional catheter with the same catheter shaft inner diameter (ID). This increased suction force will cause the clot to accelerate which further diminishes both clot/vessel friction and clot/catheter friction.

FIG. 11 also illustrates $P_{Dist}$ 114 which represents the pressure on the distal aspect of the clot from collateral blood supply via leptomeningeal connections or via collaterals from the ipsilateral anterior cerebral artery that were existing before or developed after the clot caused the vessel occlusion. This pressure, which frequently is 30-40 mm Hg, will tend to dislodge the clot toward the retrieval catheter if, and only if, the $P_{Prox}$ 111 arterial pressure on the face of the clot is eliminated. In some cases, devices, systems and methods of the present disclosure can reduce or eliminate the $P_{Prox}$ 111 by isolating the clot from proximal blood pressures and dramatically reduces the impaction friction or $F_{Impaction}$.

By applying the above friction reducing methods and maneuvers, gentle suction combined with $P_{Dist}$ pressures on the distal end of the clot will dislodge the clot without the fragmentation of current methods and promote en bloc clot removal that results in a First Pass Effect and the resulting improved clinical outcomes associated with removing all the clot during the first attempt. Adjunctive measures described above including intermittent suction, jets of upstream blood via apertures in the expandable element or catheter shaft, and maneuvers to lubricate the catheter shaft amongst others may be added to this method to further reduce friction in the catheter shaft.

Figure 12:
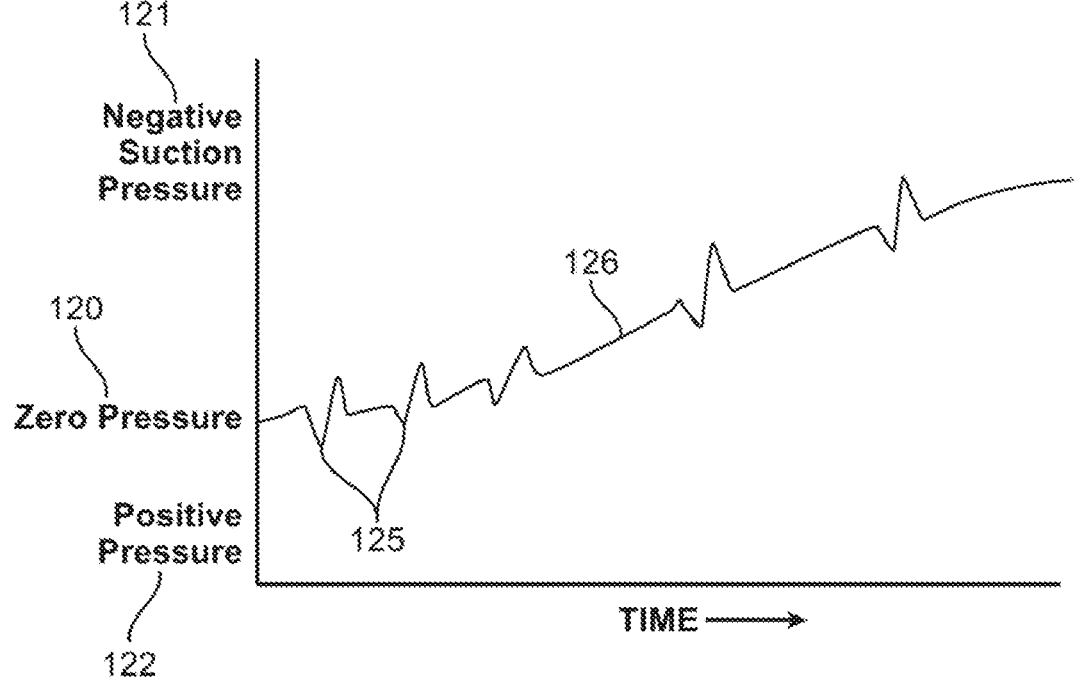
FIG. 12 shows a graph illustrating a method comprising gradually increasing the mean suction pressure in a vessel while alternating suction pressures, in accordance with embodiments.

Combining the above methods with cyclic aspiration will provide further benefit as studies have shown more effective aspiration of clot with alternating suction pressures, another method which diminishes friction. A method of the current invention can comprise placing the instant funnel catheter tip adjacent to the clot face, and expanding the funnel to cover the clot face to eliminate the impaction friction on the face of the clot and eliminating the blood pressure effect on the face of the clot, employing maneuvers to loosen the clot-vessel friction, and aspirating the clot into the instant funnel catheter with the assistance of retrograde pressure on the distal aspect of the clot from collateral blood flow while utilizing alternating or variable suction pressures. In this method, the suction pressures may be alternated or varied while gradually increasing the mean suction pressure. FIG. 12 is a graph which illustrates gradually increasing the mean suction pressure (e.g., from a zero (or baseline) pressure 120 using application of a negative suction pressure 121 and/or withdrawal or reduction of a positive pressure 122, e.g., within a lumen of a catheter of a device or system described herein) while alternating suction pressures 125 (e.g., between application of a negative suction pressure 121 and application of a positive suction pression 122 to a lumen of a catheter of a device or system described herein). These two actions work synchronously to gradually tease the clot from the vessel wall and the alternating pressures to move the clot, both of which tend to overcome the adhesion friction $F_{Adhesion}$ and the impaction friction $F_{Impaction}$. FIG. 12 demonstrates a curve 126 of gradually increasing mean suction intensity over time with a stepwise increase in mean suction intensity after each momentary variation 125 in suction intensity. This method may be included in the above novel methods of aspirating clot.

Hence a method of removal of a large vessel cerebral occlusion involving one of the internal carotid, anterior cerebral, middle cerebral, vertebral, or basilar arteries with a flow arresting funnel catheter to overcome the friction forces that inhibit the removal of the clot and inhibit the removal of the clot in one piece can comprise one or more steps of 1) insertion of a guide catheter to a target site in the internal carotid artery, 2) inserting the flow arresting aspiration funnel catheter through said guide catheter to the a second target site just proximal to the occluding thrombus, 3) deploying the funnel to occlude flow just proximal to the occluding clot face, 4) aspirating the clot with a suction apparatus while the antegrade blood flow is occluded, 5) removing the clot either a) completely through the funnel catheter or b) ingesting the clot into the funnel catheter and withdrawing the flow arresting funnel catheter containing the clot into the guide catheter and out of the body, 6) collapsing the funnel of the flow arresting funnel catheter, and 7) removal of the funnel catheter.

Step 3 also may comprise isolating the clot containing segment of the artery from blood pressure effects upon the face of the clot, thereby overcoming the impaction forces of the blood pressure that may continue to press or shove the clot more distally and inhibit the removal.

Step 4 may also comprise applying varying levels of suction pressures intermittently so as to oscillate the clot to overcome viscoelastic adhesions that contribute to the friction. The suction step may comprise gradually increasing non-linear suction pressures. The varying levels of suction may be combined with low level positive pressures to accentuate the clot oscillation. These varying levels of suction may also be utilized in Step 5.

The method of utilizing a flow arresting funnel catheter to remove a clot from cerebral vessels in Step 5 may also comprise creating flow reversal in the clot containing vessel after the removal of the primary clot through said funnel catheter while maintaining flow arrest. This latter method of flow reversal by one of continuing the suction or passively draining blood from the target site through the catheter-based device or system after clot removal may remove small micro fragments within the target vessel and small branch arteries that may not have been removed with the primary clot removal. These small micro fragments of clot may otherwise embolize distally into smaller vessels and cause minor clinical deficits and disabilities that may not occur if they were removed by this isolated flow reversal technique.

Importantly, the above techniques are not feasible or safe using balloon flow arrest or occlusion catheters immediately adjacent to the clot, as they may cause injury to the intracerebral arteries including rupture, spasm, dissections, and the like as the balloon exerts an extrinsic pressure on the vessel wall to occlude the vessel sufficient to cause those complications. The flow arrest funnel catheter of the current invention can be configured to occlude the vessel primarily by expanding the funnel and creating a seal by capturing the patients' own blood pressure to press a cylindrical portion of the funnel of the expandable element against the vessel wall rather than exerting an inherent outward radial pressure onto the vessel wall as do balloon occlusion catheters. This distinguishing feature makes the above methods effective and safe using a flow arrest funnel catheter while the above methods may be and would be unsafe if utilized with a balloon occluding catheter or even another funnel catheter which may occlude by exerting radial forces against the vessel wall to achieve occlusion.

In some cases, devices, systems, or methods described herein may be applied to Large Vessel Occlusion (LVO) stroke interventions and thrombectomies to provide a better first pass success and prevent distal embolization during the procedure when the patient has been given a lytic agent, such as r-tPA, prior to the thrombectomy intervention. The lytic can be administered after the patient has had a CT scan that shows there is no intracerebral hemorrhage (and administration is relatively safe) and before the interventional procedure in the case of a large vessel occlusion. The lytic agent can cause the clot to partially lyse or dissolve, essentially producing a thrombus that is more liquid and easier to aspirate through an aspiration catheter. However, this partial lysis can cause the clot to be more friable and more likely to fragment when guide wires, stentrievers, and the like are inserted through the clot and further fragment the liquifying gelatinous thrombus. Moreover, existing straw like aspiration catheters do not create a protective flow arrest and upon aspiration of some of the thrombus, antegrade blood flow will occur through the previously occluded segment. During this phase, small channels of flowing blood through this partially lysed and softened gelatinous thrombus may further disrupt the thrombus and carry some fragments downstream as the flow gradually increases through the partially dissolved and partially removed thrombus. In some cases such events can have significant effects. For example, once a small channel is created to allow flow, the flowing fluid channel can enlarge and cause cavitation of the material on the sides of the channel and wash much of the material of a partially lysed (e.g., softened) thrombus downstream. Thus, administering lytic agents can lead to a thrombus being more easily removed through a catheter shaft, but it may also render the clot more friable and more susceptible to fragmentation, embolizations, and incomplete thrombus removal.

Embodiments of a catheter-based device or system comprising a proximal protective flow arrest funnel catheter (e.g., as described herein) can be useful in overcoming these technical problems, for example, by isolating the partially dissolved thrombus from upstream blood flow during the thrombus aspiration and removal so that there is no blood flowing through or about the partially dissolved and more liquid thrombus during the thrombus aspiration portion of the procedure. Such embodiments can reduce or eliminate flowing blood that may cause erosion or fragmentation of a friable thrombus and subsequent embolization or fragmentation which leaves some thrombus attached to the vessel wall. Hence first pass success can be much more likely with catheter-based devices and systems described herein than the standard straw like aspiration catheters. In some cases, first pass success can be reflected in the First Pass Effect, a metric of successful intervention in which the patient has fewer and lesser disabilities and higher quality of life years as a result. Hence, the improvements facilitated by the catheter-based devices and systems described herein in stroke intervention can greatly improve the overall procedural results and clinical outcomes.

Additionally, after successful aspiration of the thrombus (e.g., using a catheter-based device or system described herein), but while the protective flow arrest features are still active, suction may be discontinued and the proximal end of the catheter left open to air so that blood from leptomeningeal or convexity collateral channels may flow retrograde through the segment of vessel that had been previously occluded by thrombus and wash out any residual debris and micro-fragments that remain, and out the proximal end of the catheter. Simply, this retrograde flow without any contribution from antegrade flow with protective flow arrest is novel and not possible with current straw like aspiration catheters. Hence, the use of a lytic agent may partially lyse or dissolve a thrombus in a stroke patient, and the use of a novel protective flow arrest device to remove the partially dissolved thrombus can prevent the downsides of the lytic of fragmentation, incomplete removal, and distal embolization, which can be significant factors in contributing to First Pass Success and First Pass Effect.

The method of treating a thrombus by partially lysing it and then removing it comprising administering a lytic agent to partially dissolve and soften a thrombus so that it is more easily aspirated, introducing a protective flow arrest device, occluding flow with the protective flow arrest device, thereby preventing any subsequent disturbance of the thrombus from antegrade blood flow, aspirating the partially dissolved thrombus while providing protective flow arrest, thereby preventing the antegrade blood flow from producing fragments of the thrombus, which may become disassociated from the main thrombus and embolize downstream, said fragments being aspirated through said protective flow arrest device along with the remainder of the thrombus. The method may also comprise that after the thrombus has been completely aspirated, allowing reverse flow, preferably without suction, from the vessel previously containing the thrombus for a period of time to clear the vessel and its branches of micro-emboli and debris.

The discussion of the novel funnel catheters and clot retractors is centered on stroke interventions but are applicable to non-stroke neurovascular interventions and many other interventions in all other vascular territories and anatomies. Devices and methods described herein may be utilized, for example, anywhere in the body in which embolus, thrombus, debris, or other material occludes or partially occludes a vessel. Specifically, use of the above methods involving the coronary, peripheral, carotid, and pulmonary arteries with minimal modifications will result in enhanced embolic protection, embolic prevention, thrombectomy, temporary vessel occlusion, stabilization of the catheter tip for coaxially placed devices, the ability to limit contrast volume, and providing a constant contrast column into which perform the intervention amongst other benefits. In many cases, catheter-based devices and systems described herein can be useful for applications other than stroke intervention, for example, for removal of thrombus or other material from blood vessels (e.g., blood vessels of varying sizes and geometries throughout the body of a subject). The devices and methods described herein may also be utilized with medicaments, fluids, and other devices not listed herein. The instant devices and methods may also be utilized when there is a need for a supportive guide catheter both with and without the need for thrombus or debris aspiration.

In the case of delivery of medicaments, a method of administering one or more of neuroprotective agents, lytic agents, blood-brain barrier transmissible agents, chemotherapeutic agents, oxygenating agents, anti-inflammatory agents, agents which lessen the stroke volume and penumbra, and the like to portions of the brain comprises some or all of placing a flow arresting funnel catheter at a target site, expanding the expandable element to produce flow arrest, aspirating blood or debris, injecting the administered agent into the vasculature distal to the flow arrest, waiting a period of time as the agent perfuses into the tissues, gradually collapsing the expandable element thereby gradually releasing the flow arrest to restore blood flow, fully collapsing the expandable element, and removing the flow arresting funnel catheter.

The clot retractor (instant clot retractor) of the current invention is an improvement over existing devices. It may comprise an expandable member on the distal end of the device comprising either 1) a self-expanding braid or stent-like structure or 2) an actively expanded braid or stent-like structure operable by a push-pull mechanism to form a distal apparatus operable to place traction on the distal aspect of the thrombus. Preferably, an actively expansile device comprising an inner and an outer shaft configured so the outer shaft connected to the proximal aspect of an expansile member and the inner sheath connected to the distal aspect of an expandible member is utilized. The expandable member is operable from a collapsed or tubular configuration to an expanded configuration designed to occupy at least the majority of the lumen of a vessel and which may be plate-like or football shaped in an expanded configuration. An actively expandable clot retractor can have advantages over a self-expandable clot retractor as, in some cases, the self-expandable retractor must be delivered coaxially through a microcatheter and the actively expanding clot retractor of the current invention may not be limited in the same way. Hence, in the case of stroke intervention, both the self-expandable clot retractor and the microcatheter must be inserted through the clot with a larger overall outer dimension than if just the instant clot retractor was placed through the clot. This larger size has the potential to not only cause potential embolic debris by disrupting the clot but may also increase the friction between the clot and the vessel wall. The microcatheter is then withdrawn allowing the self-expandable clot retractor to expand.

An actively expanded clot retractor can be inserted through the clot without the coaxial microcatheter covering it, which simplifies the procedure and disrupts the clot less because of its smaller size. There is no microcatheter to remove. The expandable element may be expanded by the push-pull mechanism when it reaches the target location.

Existing clot retractor devices, including stentrievers, are frequently designed to engage the thrombus with exposed struts or other components to insinuate or attach the clot into the clot retractor. This action may cause an increase in friction between the clot and vessel wall because of the expansion of the device within the clot creating additional radial force of the clot onto the vessel wall as well as increase the adhesion forces. These tend to combine and fragment the clot. However, if used with a proximal flow arrest funnel tipped catheter, there is no need to insinuate the clot into the clot retractor as simple retraction of the clot towards the funnel is all that is needed to successfully aspirate/ingest the clot.

In some cases, a clot retractor of the current invention can be designed to overcome the problems of the current clot retractors and stent retrievers including fragmentation and added friction. It can be designed to be inserted through the clot after a funnel catheter is deployed at or near the clot face to occlude blood flow. Hence, upon insertion of the wire-based clot retractor, the clot can be protected and even if a small amount of fragmentation occurs during passage, there will be no blood flow to embolize it distally. Moreover, some embodiments of the catheter-based devices and systems of the current invention can be designed to be delivered through the clot without a coaxially positioned microcatheter covering it. This diminishes the size of the device traversing the clot which will diminish the fragmentation and diminish the added friction of placing a device through the clot. The current clot retractor can be delivered to a point beyond the distal aspect of the clot and then expanded distal to the clot. This can obviate the friction issue and fragmentation issue caused by the existing stent retriever devices. Traction is then exerted upon the distal aspect of the clot in conjunction with the suction provided by the funnel catheter proximal to the clot and bolstered by pressure $P_{Distal}$ on the distal aspect of the clot from collateral flow as per FIG. 11.

The method of pairing a clot retractor, designed to minimize the fragmentation of the clot and minimize or obviate the added friction caused by the action of the existing clot retractors, by adding a large mouth funnel catheter of the current invention and utilizing the two devices together to achieve "en bloc" or complete removal of the entire intact clot is an object of this invention. In the current proposed method, the distal end of the catheter-based device or system may be positioned near the face of the clot just proximal to it with the funnel deployed occluding flow. A clot retractor, which can comprise a braid or stent like structure activated by a push-pull mechanism, in a collapsed position is passed through the clot and distal to it. The push-pull mechanism is then utilized to expand the distal aspect of the clot retractor only to the size of the vessel at that location. Suction is then provided through the aspiration funnel catheter. Since blood flow is occluded by the funnel catheter, all of the suction is directed distal to the clot rather than the non-directed suction of standard straw like catheters. This directed suction will cause the proximal portion of the clot to detach from the vessel wall as the proximal clot is elongated as it is sucked into the conical shaped funnel of the funnel catheter. This detachment because of the progressive elongation of the clot will proceed from the proximal portion more distally to an intermediate section of the clot as the clot continues to elongate with continued suction. This action can overcome the inherent friction between the clot and the arterial wall rather than adding to the friction as per the current standard straw-like catheters and stent retrievers and methods of utilizing them.

Returning to the aspiration method, after a short time (which may be from several seconds to several minutes) of suction by the catheter-based apparatuses described herein to allow for the elongation and separation of the clot from the vessel wall, traction may be applied by the instant clot retriever to further urge the distal aspect of the clot forward towards the mouth of the funnel catheter. At this time, most of the clot has been separated from the vessel wall by the suction action and the resultant elongation of the clot as it is aspirated into the funnel catheter. A portion of the distal aspect may not be separated from the wall however because of its distance from the suction source. Gentle forward traction of the instant clot retractor may then be applied to pull the distal aspect of the clot forward and into the funnel catheter for removal. Since the proximal aspects of the clot have been separated from the vessel wall by the suction, the forward traction of the instant clot retractor will not add friction as the distal clot can move proximally toward the funnel catheter more easily. Forward traction on the clot would produce more friction if there were significant clot still attached to the vessel wall as is the case with existing methods and systems. An advantage of this instant method of utilizing a funnel catheter proximally to elongate the clot and detach it from the wall eliminates the friction problem of the other devices and methods.

Hence, the configuration and elements of the current clot retractor will be structurally and functionally different than existing devices.

Figure 13:
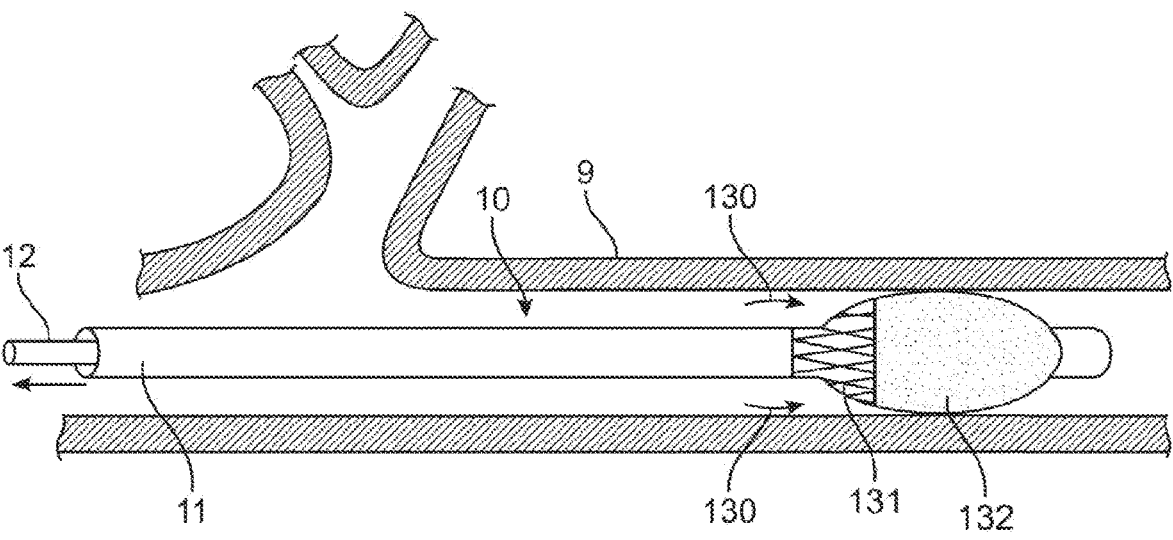
FIG. 13 shows a schematic of a clot retractor, in accordance with embodiments.

FIG. 13 demonstrates an expandable clot retractor device with struts 131 exposed to the clot. Typically, in existing devices the proximal struts are positioned with greater spaces between them than the more distal struts which are designed to capture smaller fragments or the distal struts may be covered with a membrane 132, as is illustrated here, or with struts with smaller spaces between them (not shown). Insinuation and capture of small particles in the distal aspect are the goals of some existing clot retractors as they are typically used without proximal flow arrest near the clot face as is the cased of the current clot retractor and must attach themselves to the clot. Clot fragmentation results from this insinuation and distal embolization occurs. However, a clot retractor (e.g., if used with a protective flow arrest aspiration catheter as described herein) needs only to urge the clot forward towards the expanded funnel of the expandable element, without any insinuation or exerting a radial force of the clot onto the vessel wall, but with the focused suction afforded by the occlusion of the vessel by the expandable element.

FIG. 13 depicts a clot retractor that is designed to expand in a non-linear manner so that the expandable element elongates when a prescribed diameter of the expandable element is reached. This device is configured to expand partly because of blood flow 130 which may pass through the porous proximal segment 131 of the expandable element and tend to expand the non-porous distal aspect 132 with a parachute like effect. The clot retractor can comprise an expandable element with exposed struts 131 to engage or insinuate the retractor into the clot. Since there is no need to engage or insinuate the clot retractor into the clot and since it may be deleterious and create fragments if engagement or insinuation were performed when protective flow arrest is utilized immediately proximal to the clot as with some embodiments of the instant funnel catheter and methods, various embodiments of an improved clot retractor of the current invention may not possess these features.

Figure 14:
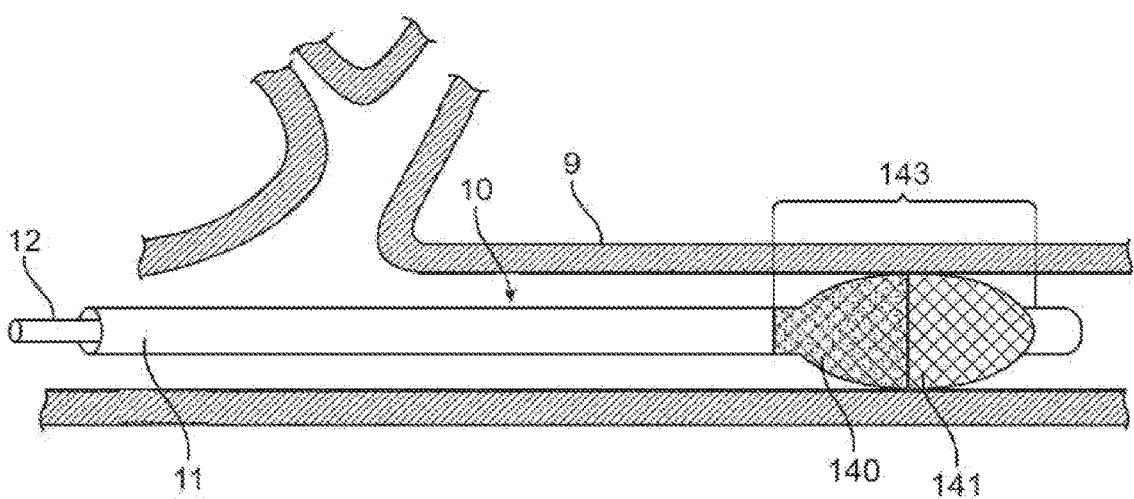
FIG. 14 shows a schematic of an improved clot retractor, in accordance with embodiments.

Instead, as shown in FIG. 14, an improved clot retractor of the current invention comprising an inner shaft 12, and outer shaft 11, an expandable element 143 with proximal end connected to the distal aspect of the outer shaft 11 and the distal end of the expandable element connected to the distal end of the inner shaft 12 also provides a proximal half of the expandable element 143 which comprises an impermeable or mostly impermeable membrane 140 that covers or is part of the expandable element 143 that will contact the distal aspect of the clot when traction is applied. The membrane 140 will prevent insinuation of the struts or other components of the expandable element into the clot. The braid of the expandable element will give the surface some texture to prevent slippage around the clot when traction is applied but without the insinuation of other devices. The distal structure 141 of the expandable element 143 may be left porous and serves to only support the proximal portion 140 of the expandable element 143.

Figure 15:
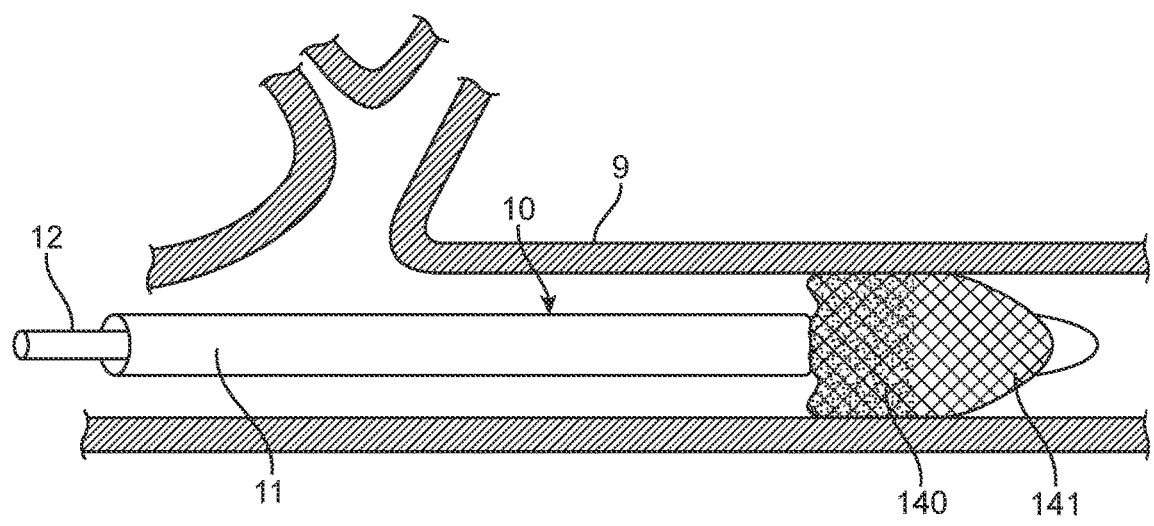
FIG. 15 shows a schematic of a device comprising an impermeable membrane on the proximal aspect of an expandable element of the device, in accordance with embodiments.

FIG. 15 demonstrates an alternative embodiment in which the impermeable membrane is placed on the proximal aspect 140 of the expandable element 143. In this configuration, after movement of the inner 12 and outer 11 shafts toward one another, additional forward movement of the outer shaft 11 will invaginate the proximal portion 140 of the expandable element 143 into a cup like shape. This configuration will focus the majority of the traction pressure near the vessel wall and tend to overcome the friction and adhesive forces between the vessel wall and the clot that may limit its mobilization. The expandable element 143 structure or braid may comprise a heat set area of the preferred nitinol elements to fold over in this desired inverted configuration. The braid may be heat set to limit or provide the desired outward radial pressure upon the vessel wall as well.

Expanding the instant clot retractor distal to the clot with wall contact and not within the clot, e.g., as with existing devices, will obviate the increase in friction caused by the expanding retriever within the clot. This method will also save time as one will not have to wait for prescribed minutes to allow the stent retriever to expand and insinuate itself within the clot. This is advantageous, as "time saved is brain saved."

In either configuration depicted in FIG. 14 and FIG. 15 the impermeable membrane 140 will serve to enhance collateral flow once traction is initiated as the proximal movement will create an area of relatively diminished pressure behind the clot retractor essentially "pulling" some blood through the collateral channels over the convexity of the brain and augmenting the collateral flow. This may at least partly counter the impaction forces that occurred when the clot embolized and lodged in the vessel. Gradual traction on the current instant clot retractor combined with gradually increasing suction proximally through the aspiration funnel catheter with the added distal pressure from collateral circulation on the distal aspect of the clot will overcome the friction and adhesion forces and dislodge even recalcitrant clot, urging it proximally to be ingested into the larger funnel mouth of the aspirating funnel catheter.

In some embodiments an oscillator or vibrator can be added to a clot retractor described herein to provide longitudinal vibrations which can cause micro-movements within a thrombus. This may also overcome the friction and adhesion issues that exist. The vibratory means may comprise an apparatus that is removably attachable to the proximal end of the instant clot retractor. The method of using such would comprise attaching a vibratory means apparatus to the proximal end of the instant clot retractor once it is placed at its target site, providing vibrations while minimally retracting the instant clot retractor, ceasing the vibrations at some point in the retraction of the clot, and removing the apparatus from the instant clot retractor either before or after complete clot retraction. Alternatively, the vibratory means may be attached to any coaxial guide wire or member and by providing vibrations by a vibration generator to create pressure waves that are transmitted to the clot and cause micro movements of the clot which overcome the friction and adhesion issues.

The method of utilizing a clot retractor described herein may vary depending on the success or lack of success of using the instant funnel catheter and the methods of clot removal without the clot retractor. Typically, the instant clot retractor is utilized after unsuccessful first pass attempts at removal with only the funnel catheter, although it may be used primarily because of clinical judgement or because pre-intervention interrogation of the clot consistency with CT or MRI may determine that a firm, white, or fibrinous clot may need to be approached with the instant clot retractor initially rather than using it as a "bail out" device.

The novel catheter-based devices and systems and clot retractor improvements described herein will be successful in mobilizing the clot, overcoming the friction and adhesion issues, and may lessen the consistency so that the entire clot is aspirated easily through the aspiration funnel catheter without the use of a clot retractor or other method to pull the clot into the aspirating funnel catheter.

If the clot is predominantly white, firm clot, it may not be able to be compressed enough to be aspirated through the lumen of the aspiration catheter in rare instances. In these rare cases, another alternative embodiment of the device and method of clot retrieval may comprise occluding the vessel near the proximal clot face with the aspiration funnel catheter, applying suction thereby withdrawing the face of the clot into the expandable element and into the distal lumen of the catheter, and gradually withdrawing the inner shaft along with the partially ingested and secured clot proximally while gently advancing the outer shaft member. As the clot and inner shaft attached to the base of the funnel is withdrawn and the outer shaft is urged distally, the expandable element will elongate over the thrombus and cover it so that the entire funnel catheter may be withdrawn into the larger guide catheter with a larger ID for removal from the body. The braid segment of the expandable element may be elongated to envelop and surround a clot of 2-3 cm. in length which may not be otherwise aspirated into the aspiration catheter lumen for removal. This elongation of the expandable element over the clot combined with suction will secure the clot so it can be withdrawn into the larger and more proximal situated guide catheter. This method and maneuver may, in most cases, obviate the use of a distal clot retractor, stentriever, or other device to secure the clot prior to transfer to the guide catheter, although those distal devices may also be employed with it.

A remote target site that is difficult to assess is the middle cerebral artery where an embolized thrombus lodges and causes a large vessel occlusion type stroke. The intracranial internal carotid artery is very tortuous and navigation of a catheter capable of removing this thrombus may be difficult because of the serpiginous course and because the tip of the catheter or the guide wire may become engaged in side branch origins while being advanced to the target site. Modern catheter wall construction has progressed so that aspiration catheters are more easily advanced to the target site than previously, but there is still difficulty in many patients. Frequently, navigation of the aspiration catheter to the clot face requires placing a guidewire, microcatheter, or even a stent retriever through the clot and more distally in the middle cerebral artery to support advancement of the aspiration catheter to the clot face. This interaction with, and passage through, the clot will disrupt the clot somewhat and fragment it, causing the subsequent clot aspiration to leave fragments behind resulting in incomplete clot removal or to cause fragments to embolize distally once the majority of the clot is removed and blood flow is restored. Hence there is a need for navigational enhancements, which overcome the challenges of the tortuosity and side branch origins, to make the trackability, navigability, and access to the clot face simpler, easier, and quicker, and to avoid interaction of a guidewire or microcatheter with the clot and the resultant fragmentation caused by such interaction. In some cases, the devices, systems, and methods described herein are useful for enhancing navigational abilities of an aspiration catheter to access the clot face at any location in the body without guidewires, microcatheters, or other supportive tools interacting with it, thereby avoiding the fragmentations and complications that occur with the positioning effort associated existing aspiration catheters. While these methods and techniques are directed to the middle cerebral artery, it is used only as an example, and the methods and techniques may be employed for target sites at other locations throughout the body.

An important means of achieving enhanced navigability can involve catheter wall construction utilizing techniques to produce flexibility and pushability that enhance the forward navigability of the catheter. There needs to be an optimal balance of flexibility to pass through tortuous anatomy and pushability to advance the catheter forward. These two qualities are antagonistic, as greater flexibility would promote less pushability and greater pushability would require a stiffer, and less flexible, catheter. Hence, navigational enhancements may serve to require less pushability if they were configured to advance or urge the catheter forward, and hence the catheter may be provided with more flexibility.

Figure 16:
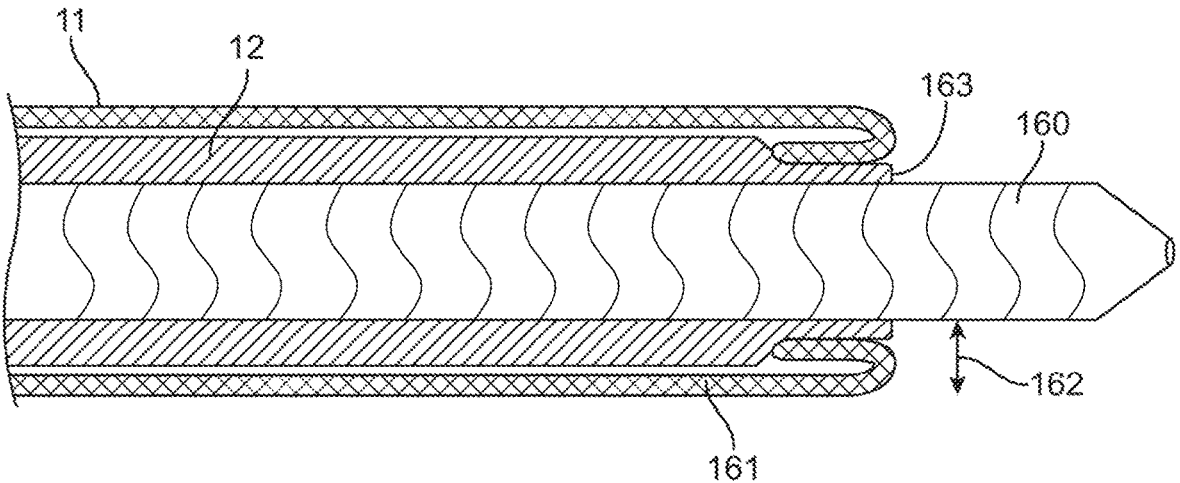
FIG. 16 shows a schematic of a device comprising an expandable element in a collapsed configuration and a dilator inserted through the lumen of an inner catheter shaft of the device, in accordance with embodiments.

Some dual shaft funnel catheters lack a tapered distal tip as there is a need for two coaxial shafts to be attached to respective ends of the expandable element to expand, contract, and manipulate the expandable element. This configuration precludes the standard tapering of the tip and creates a non-tapered configuration between the outer surface of the catheter and the inner surface that may not be conducive to navigation within the vessel and may preclude the atraumatic placement into the vessel over a guidewire or a smaller catheter. In some cases, it is an object of the current invention to address and solve both issues. This problem is illustrated in FIG. 16 which shows the flow arrest funnel catheter 10 with the expandable element's funnel collapsed and, in a configuration appropriate for navigation of the catheter through vessels to the target site. One can appreciate that the ledge 162 created between the funnel catheter tip 163 and the coaxial indwelling guidewire or dilator 160 is greater than with a standard single wall catheter configuration in which the distal tip is tapered (not shown). In some cases, there is an inability to taper the distal end of the funnel catheter 163 to create a smooth transition between a coaxial inner catheter 160 necessary for navigation in the tortuous vessels of the body without engaging side branch origins, plaque within the artery, or the vessel wall because of the braid 161 being attached to the distal shafts 11, 12.

Moreover, the configuration of some devices requires placement of the braid along the outer surface of the inner shaft in a collapsed configuration. This makes a transitional segment even more difficult in addition to the braid being exposed to the vessel wall during transit. This impediment to a smooth transition is another reason to place the braid along the inner surface of the outer shaft as can be the case with some configurations of devices, systems, and methods described herein.

Figure 17A:
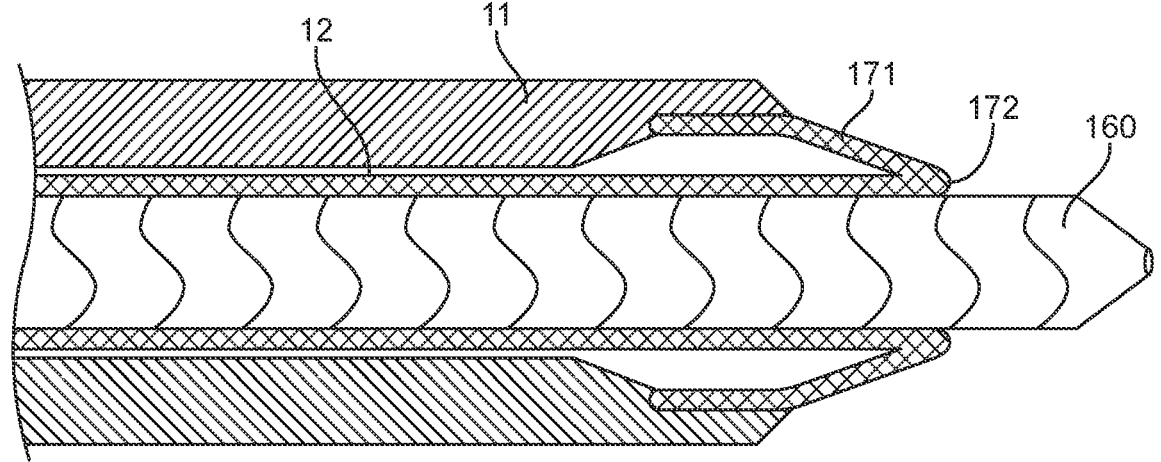
FIG. 17A shows a schematic of a device useful for navigating a blood vessel comprising an expandable element, an inner dilator, and a transition element between the device and the dilator, in accordance with embodiments.
Figure 17B:
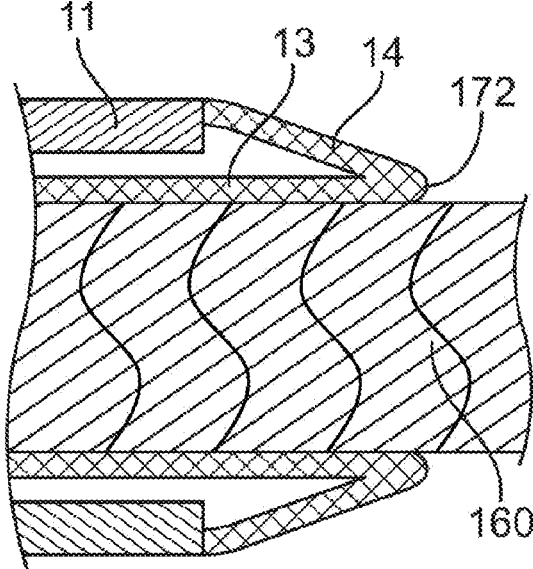
FIG. 17B shows an expanded view of the device comprising an expandable element shown in FIG. 17A, in accordance with embodiments.

A preferred solution to this navigational impediment at the tip is to configure the flow arrest funnel catheter so that the braid 161 of the expandable element acts as the tapering means to facilitate both navigation and vessel entry. In a preferred embodiment as shown in FIG. 17A and FIG. 17B, the expandable element in a collapsed configuration is aligned on the inside of the outer shaft 11. This embodiment provides a means to create a transition that will allow navigation and vessel entry and overcome the step or ledge 162 created by the existing catheter system. This means comprises a transition segment 171 of the braided expandable element attached to the outer shaft 11 of the dual shaft funnel catheter configured to project distally from the distal tip of the outer shaft 11 and project slightly inward towards lumen of the funnel catheter in a conical shape, further comprising a fold at the distal end 172 of the transition segment 171 that directs the braid to a more proximal location for attachment to the inner shaft 12. This configuration can provide a smooth transition between the funnel catheter tip to a coaxial inner device 160 which overcomes the problem with existing catheter systems. Preferably, the fold 172 at the distal end of the transition segment 171 comprises a heat set of the braid, although other techniques may be utilized to facilitate a smooth reverse fold or inversion of the transition segment braid.

While the transition segment may be formed by advancing the inner shaft after the flow arrest funnel catheter has been inserted into the vessel, preferably this configuration will be preset during the manufacturing and assembly process. In the latter, a detente in the handle (not shown) may be operative to lock the configuration into this position with the transition segment of the expandable element configured to provide a smooth transition to the tip of the collapsed expandable element. Moreover, because the braid is not a smooth surface and may now be exposed to the vessel wall, a further preferred embodiment may comprise elements to smooth the relatively rough surface of the braid that will be exposed to vessel wall contact. This may comprise covering the tapered and conical section of braid with an elastomer, such as silicone which is utilized in other portions of the braided expandable element, although other elastomers and materials may be utilized. This may take the form of a layer of an elastomer or other material sufficient to overcome the uneven braid surface and to make the surface relatively smooth so that it will slide easily along the vessel and eliminate the friction that may occur with exposed braid.

An alternative embodiment may instead comprise strips of elastomer or other material directed from the attachment of the braid of the expandable element with the outer shaft to the distal end of the tapered transitional segment of sufficient number and thickness to prevent the braid from contacting the vessel wall thereby leaving the spaces between these strips devoid of the elastomer and permeable to blood flowing therethrough. In this embodiment, the porous braid between the strips will allow blood to flow into a cavity created by minimal expansion of the expandable element to urge the catheter forward while the strips prevent abrasion of the vessel wall by exposed braid.

FIGS. 18A-18D demonstrate a novel dilator 160 that may be utilized with funnel catheter or other relatively non-tapered catheters to introduce these catheters into an artery primarily instead of using a separate introducer sheath to coaxially introduce the non-tapered catheters. The novel dilator 160 is configured to be placed coaxially within another outer catheter, preferably the funnel catheter 10 with the transition enhancements of FIG. 17A and FIG. 17B. It comprises a thin conical shaped elastomer 180 which is attached to the distal tapered portion of the dilator shaft 160 as demonstrated in FIG. 18A. There may be a shallow recess 181 provided for the attachment of the elastomer 180.

Figures 18A, 18B:
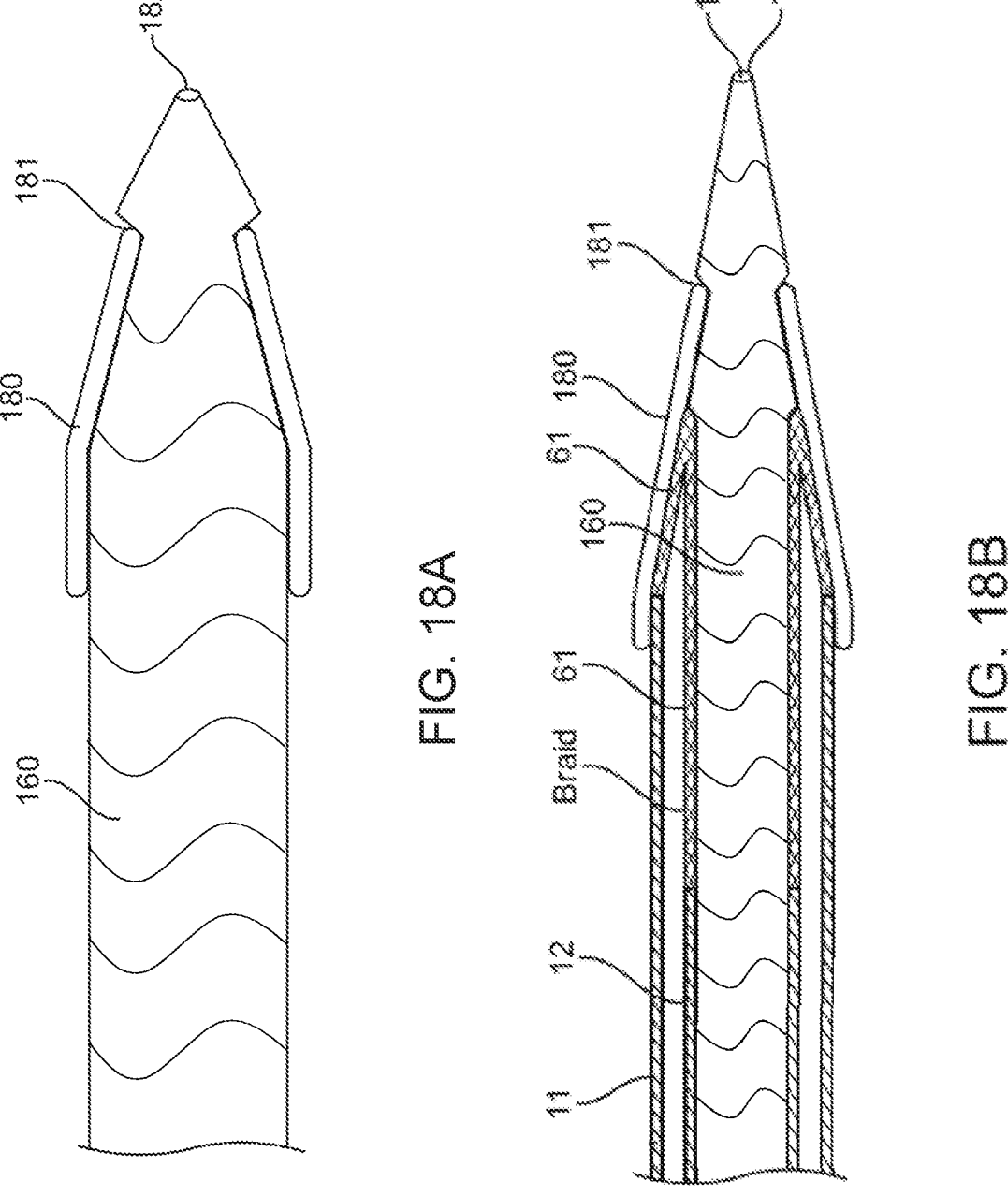
FIG. 18A shows a schematic of a device comprising a dilator and an elastomer covering, in accordance with embodiments.
FIG. 18B shows a cross-sectional view of a device comprising an expandable element and a dilator with an elastomer covering positioned over a distal end of the device, in accordance with embodiments.

FIG. 18B demonstrates the novel dilator 160 within a collapsed funnel catheter 10 with the conical elastomer 180 covering the distal funnel catheter tip and the transitional segment 61. This is the configuration used for vessel entry.

Figure 18C:
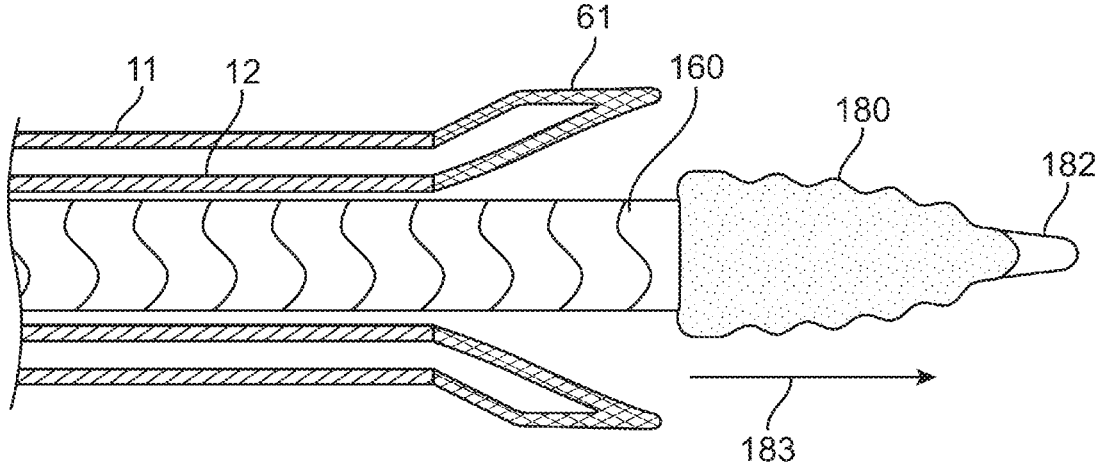
FIG. 18C shows a schematic of a device comprising an expandable element and a dilator with an elastomer coating advanced distal to the body of the device, in accordance with embodiments.
Figure 18D:
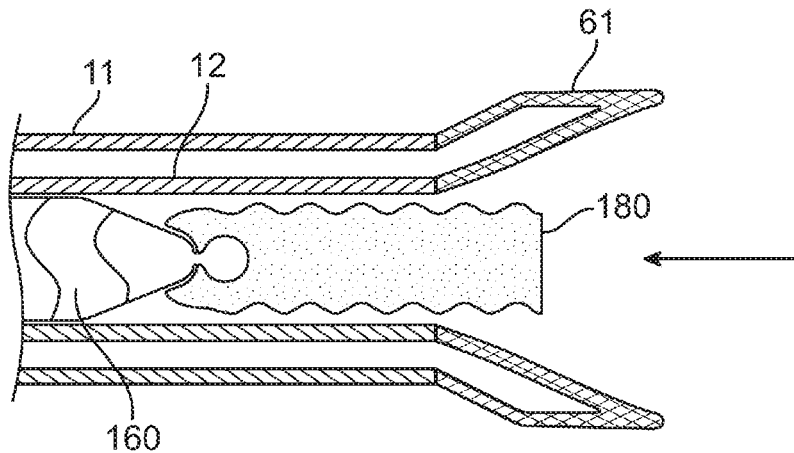
FIG. 18D shows a schematic of a device comprising an expandable element and a dilator with an elastomer coating partially retracted into the device for removal of the dilator, in accordance with embodiments.

This configuration may be utilized in a method of vessel entry which comprises placing the dilator 160 with the elastomer 180 mounted over the tapering transition segment and into the vessel 9 over a guide wire or smaller catheter 183, then advancing the dilator distal to the end of the funnel catheter thereby removing the elastomeric covering 180 from the distal funnel catheter, deploying the funnel catheter into a funnel shape as demonstrated in FIG. 18C, and withdrawing the novel dilator and elastomeric component through and out of the funnel catheter as demonstrated in FIG. 18D.

Figure 19A:
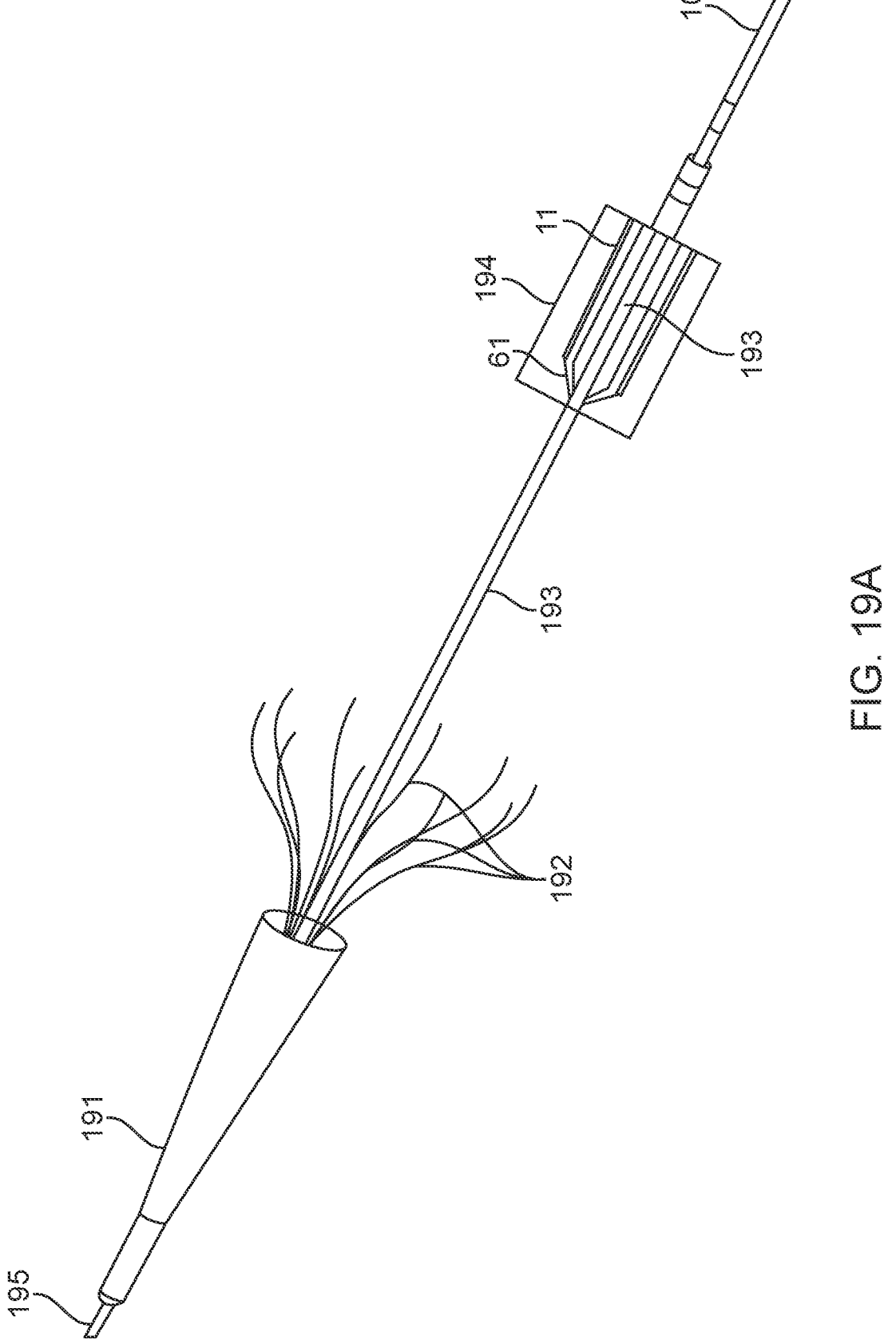
FIG. 19A shows a schematic of a device comprising an expandable element and a tined dilator apparatus, in accordance with embodiments.

FIG. 19A demonstrates another novel dilator apparatus that may be utilized for vessel entry. A dilator can comprise a distal tapered segment 191 attached to a plurality of tines 192 configured to collapse toward one another which cover the distal aspect of the funnel catheter 194 for vessel entry. A stiff tubular member 193 is shown proximal to the tined apparatus and may be place over a guide wire 195.

Figure 19B:
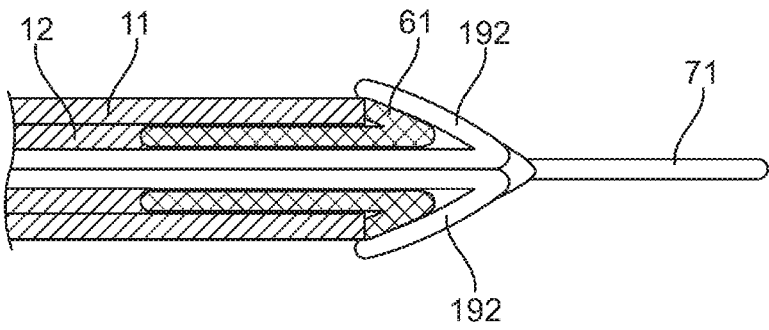
FIG. 19B, FIG. 19C, FIG. 19D, and FIG. 19E show steps in the deployment of a device comprising an expandable element and a dilator, in accordance with embodiments.

FIG. 19B demonstrates this novel dilator apparatus distal to a funnel catheter with a guide wire 195 projecting distally. The tines 192 are shown expanded for illustration purposes as they can be configured to cover and compress the distal aspect of the funnel catheter 194.

Figure 19C:
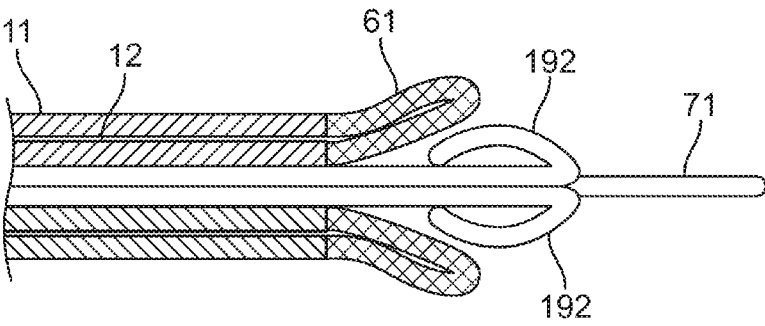

FIG. 19C demonstrates advancement of the tined dilator apparatus distally so the tines 192 no longer cover the distal funnel catheter 194 and can be collapsed towards one another. The expandable element 61 can be deployed in an expanded configuration (e.g., as shown in FIG. 19C).

Figure 19D:
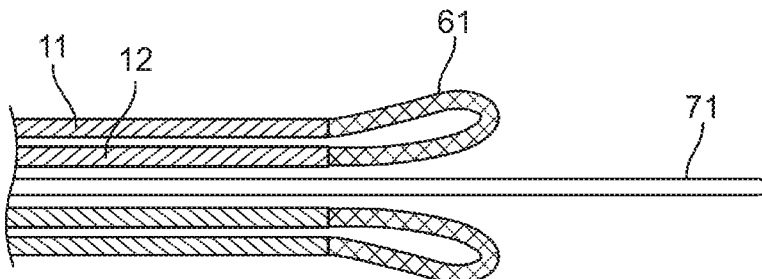

FIG. 19D shows the tined dilator apparatus 192 having been removed leaving a guidewire 71 in the lumen of the funnel catheter.

Figure 19E:
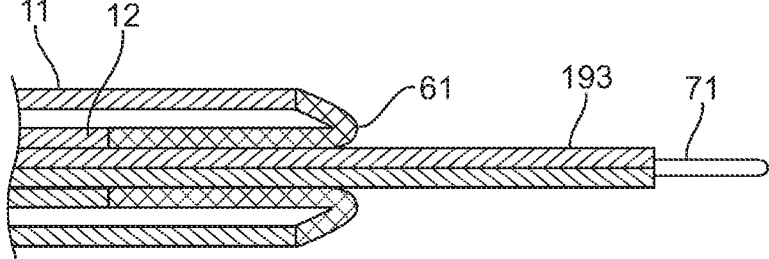

FIG. 19E, shows an example in which an intermediate catheter 193 has been inserted through the lumen of the funnel catheter for navigational purposes. The expandable element has been collapsed for navigation purposes in this example.

Figure 20A:
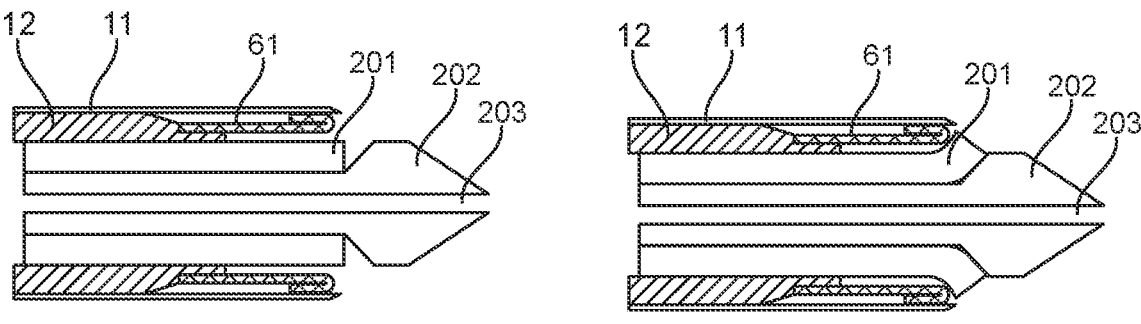
FIG. 20A shows a schematic of a device comprising an expandable element, an inner dilator, and an outer dilator, in accordance with embodiments.

Even another means of providing a tip configuration to a funnel catheter with an inner and outer catheter shaft capable of entering an artery relatively atraumatically is demonstrated in FIG. 20A. In this instance, a malleable portion of an outer dilator apparatus 201 can cover the ledge created by the two catheter shafts of the funnel catheter and the lack of a tapered end. The malleable outer dilator apparatus 201 can be compressed by withdrawing the inner dilator apparatus with an enlarged nose section of the inner dilator 202, which may comprise a lumen 203. This covers the end of the funnel shafts 11, 12 and provided for a smooth transition.

Figure 20B:
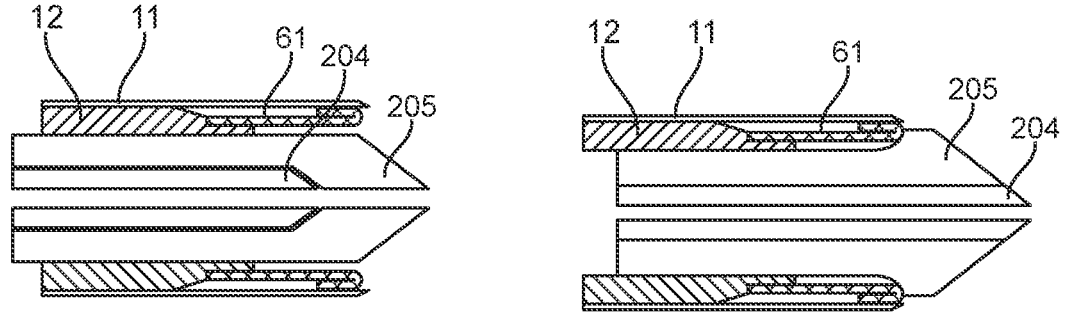
FIG. 20B shows a schematic of a device comprising an expandable element, an inner dilator, and an outer dilator, in accordance with embodiments.

In a different configuration shown in FIG. 20B, an inner separate dilator 204 is advanced to expand the distal aspect of an outer dilator component 205 thereby covering the end of the funnel catheter. Both of these embodiments are complex and require multiple components and may not function as well as the embodiment in FIG. 17A and FIG. 17B.

Any of the above descriptions may be combined with other descriptions to provide a smooth tapered transition of the distal tip of the flow arrest funnel catheter and create an ease of navigation through the vascular tree to remote target sites.

Frequently, the flow arrest funnel catheter described herein may be utilized as a conduit for other catheters and devices that perform various vascular interventions. These devices are all inserted through the funnel catheter, eliminating catheter exchanges except coaxially within the funnel catheter. Hence there is less need for a vascular introducer sheath designed to facilitate the multiple catheter exchanges and manipulations of many procedures. In essence, the funnel catheter is inserted and then left in place as a conduit for subsequent catheters and devices. Hence, it acts as a guide catheter when inserted through an introducer sheath, but with no real need for the introducer sheath to perform any function other than insertion of the flow arrest funnel catheter. The standard introducer sheath adds approximately two French (0.67 mm or 0.027") to the arteriotomy size which may make vessel closure and hemostasis more problematic after removal of the catheters and introducer sheath. In some cases, a catheter-based device or system described herein can allow the flow arrest funnel catheter to be inserted without an introducer sheath and become a "guide sheath."

While the tapered configuration described above may be utilized, the braid may be too soft to enter the vessel without deformation occurring because of the pressures and friction associated with entering an artery. Hence, means to facilitate the atraumatic entry of the funnel catheter into an artery or blood vessel may comprise a configuration which shields and at least partially covers the soft and flexible braid and protects it from deformation while facilitating an atraumatic insertion of the funnel catheter into the artery. This means may comprise a stiff dilator to provide the forward force needed, the stiff dilator possessing a tapered tip and a conical shaped elastomeric material that covers the braided portion attached to the tapered tip extending proximally to cover the transition segment and the distal aspect of the outer shaft of the funnel catheter. This entry means configuration without the funnel catheter is depicted in FIG. 18A. FIG. 18B is a longitudinal section of the entry means placed over the funnel catheter tip, covering the transition segment of the expandable element and the most distal aspect of the funnel catheter. There may be a circumferential notch 181 in the tapered tip 182, for example, to which the conical shaped material can be attached.

To remove the entry means after vessel entry, it may be advanced distally to disengage if from the funnel catheter and then withdrawn through the funnel catheter. In FIG. 18C, the entry means has been advanced distally out of the funnel catheter and the funnel deployed and positioned for removal. If the conical elastomeric material does not lie flat or is wrinkled, as shown in FIG. 18C, after disengaging the entry means from the funnel catheter as depicted, the entry means may be withdrawn through the funnel catheter shaft by withdrawing the shaft and inverting the conical elastomeric material that will trail behind the tip of the entry means as it is withdrawn. This is illustrated in FIG. 18D. Alternatively the tip of the entry means may comprise an elongated notch (not shown) into which the conical elastomeric material may nest after disengagement to facilitate withdrawal.

An alternative means of providing a tip configuration capable of vessel entry is illustrated in FIG. 19. This comprises a funnel catheter in a configuration with the previously described transition segment coaxially positioned over a separate dilator apparatus comprising a stiff dilator configured to fit within the inner lumen of the funnel catheter, said dilator having a tapered tip for easy vessel entry over a guidewire. The tip component comprises a series of metal strips or tines configured to cover the transition segment. The metal strips are configured by heat treatment, physical placement, or other means so the exposed tips exert a compressive force over the transition segment and the outer surface of the distal funnel catheter. This compressive force configuration will cause the metal strips to collapse along the shaft of the dilator when the separate dilator apparatus is advanced distal to the distal end the funnel catheter. Advancing the separate dilator apparatus effectively unsheathes it from the funnel catheter and collapses the tines or metal strips so that the dilator apparatus may be withdrawn and removed through the lumen of the funnel catheter after vessel entry.

A catheter-based device or system described herein can be used as a conduit to enhance navigation of an aspiration catheter or other catheter to a distal target site, for example, using a method comprising one or more of the following steps: 1) placing a supportive catheter-based device or system capable of navigating to a supportive target site as close to a tortuous segment of a blood vessel as possible, 2) expanding the expandable element without occluding blood flow (e.g., to center and stabilize the tip of the supportive funnel catheter), 3) advancing an aspiration catheter coaxially within the supportive funnel catheter (e.g., through the tortuous segment of the vessel with stabilization and support of the supportive catheter-based device or system to the face of an obstruction (e.g., the face of a clot or debris), for example, without penetration of the clot by coaxial guidewires, catheters, or microcatheters, 4) further deploying the expandable element to occlude blood flow or create flow arrest, 5) aspirating the obstruction or debris into the aspiration catheter, 6) retrieving the aspiration catheter and clot into the supportive and flow arresting catheter-based device or system, and 7) removing of the clot from the body. Step 1 may comprise placing the tip of the catheter-based device or system at the C4 (cavernous) segment or C2 (petrous) segment of the internal carotid artery, for example, in the case of accessing a clot in the middle cerebral artery for stroke intervention. Step 1 may involve placing the tip of the supportive funnel catheter in the left main coronary artery or its branches in the coronary circulation or immediately proximal to a tortuous segment elsewhere in the vascular bed. Step 2 may involve either expanding the funnel to either occlude flow or preserve flow while anchoring or stabilizing the distal tip of the device. Step 3 may involve advancing a catheter-based device or system described herein with the expandable element in a collapsed or partially collapsed configuration to the clot face or debris. In some cases, a method comprising one or more of Steps 1-7 described above can comprise a step after Step 5 and after the clot or debris is aspirated and removed from the body which comprises providing flow reversal within the middle cerebral artery or target artery by discontinuing suction and, with the expandable in an expanded or partially expanded configuration (e.g., to provide flow arrest at the site of the former clot face site), allowing retrograde blood flow from collateral circulation to flow through the site of the recently removed clot, into the funnel, and out of the body to further remove micro-fragments of the clot or debris or other fragments of clot or debris that may not have been removed by Step 5.

Increasing the navigability of aspiration catheters so that they are capable of accessing debris or a clot face and not penetrating the debris or clot face with supportive wires or catheters when the debris or clot face is distal to a tortuous segment of a vessel can also be accomplished with other methods. In some cases a catheter-based system or device described herein designed to aspirate the clot (e.g., in addition to or instead of being designed to support the catheter, as described herein) can be used in a method comprising partially expanding the expandable element on the tip of the aspirating funnel catheter so that the tip will not engage in the branch vessel origins during navigation, which can be a problem with existing devices and systems. An aspirating catheter-based device or system (e.g., as described herein) may comprise means to capture the forward flowing blood to urge the catheter tip forward within the vessel (e.g., as described herein) as well as the means to expand the funnel so that side branch orifices are not engaged. In some cases, a method of enhancing navigation of the aspirating catheter-based system or device through a tortuous segment can comprise one or more of the following steps: 1) advancing the aspirating catheter-based device or system to a point proximal to a tortuous segment of artery, 2) minimally expanding the expandable element at the tip so that the expandable element either a) has a larger diameter than the outer dimension of the catheter, or b) is sufficiently expanded to capture antegrade blood flow within the minimally expanded expandable element (e.g., to urge the catheter forward), or c) both, 3) providing a (e.g., manual) forward-pushing force (e.g., in a distal direction) on the proximal aspect of the catheter while allowing the blood flow captured in the distal expandable element to further urge the catheter forward through the tortuous segment, and 4) positioning the catheter tip at the clot face (e.g., without penetration of or interaction with the clot face).

A combination of these novel methods of enhancing navigation of an aspirating funnel catheter can, in some cases, produce better results than using them individually. Hence, another method comprises utilizing a combination of steps of one or more of the methods together, for example: 1) providing a stability platform comprising a supportive catheter-based device or system described herein with or without flow arrest immediately proximal to a tortuous segment, 2) providing a method of minimally expanding the expandable element of an aspiration catheter to inhibit engagement of the catheter tip with side branch origins, and 3) providing a method of partial expansion of the catheter-based system described herein to capture forward flowing blood to urge the catheter forward.

A method of primarily introducing a supportive funnel catheter percutaneously into a blood vessel without the use of an introducer sheath comprises the steps of 1) placing a means configured for entry (entry means) coaxially through the supportive funnel catheter, 2) securing the means over the distal tip of the supportive funnel catheter, 3) advancing the supportive funnel catheter and the entry means into a blood vessel coaxially over a guidewire or other supporting member, 4) advancing the entry means distally from its attached position on the funnel catheter to an unattached position distal to the tip of the supportive funnel catheter, 5) deploying the funnel apparatus into a funnel shape, 6) withdrawing the entry means tip through the expanded funnel, 6) collapsing the funnel, 7) inserting a guidewire or catheter antegrade through the funnel catheter, and 8) navigating the funnel catheter to a target site in the vasculature. Steps 6 and 7 may be reversed. The forgoing maneuvers may also describe the method of converting a catheter normally inserted through an introducer sheath into a guide sheath that needs no introducer sheath.

Much of the foregoing is presented in the context of a procedure of removal or aspiration of clot, debris, embolus, or thrombus and preventing distal embolization during that procedure. The systems and devices of the present disclosure may have other uses and may be used with other methods. One of additional application of systems and devices described herein may be the method of using the occluding funnel catheter primarily for prevention of emboli occurring during commonly performed interventional procedures throughout the body.

Embolization occurs with almost every interventional procedure designed to correct a partial or complete blockage of the vascular channel whether the procedure is angioplasty, atherectomy, CTO crossing or thrombectomy amongst others. Embolization also occurs when utilizing drug coated balloons as particulate matter within the excipient coating embolizes into distal tributaries.

In some cases (e.g., in the case of lower extremity interventions), embolization is grossly underappreciated and not detected routinely as post procedure imaging usually evaluates only the target site and not the distal runoff of the foot. Moreover, many embolic particles are too small to be detected by angiography. Embolic protection filters can be used for certain debris liberating procedures and in femoral and some popliteal lesions, but the vessel of the lower leg below the knee (BTK) are too small to accommodate many embolic protection filters. Patients with peripheral vascular disease in the lower extremities frequently have multiple procedures and, hence, multiple episodes of distal embolization of matter occluding smaller arteries and arterioles in vulnerable distal tissues of the leg and foot. Most of these patients have pre-existing microcirculatory compromise from diabetes or renal failure. Repeated embolizations may result in avoidable amputations, poor tissue perfusion, delayed wound healing, and need for subsequent repeat interventions amongst other effects. However, devices, systems, and methods described herein are well-suited to avoid embolization during such lower-extremity procedures.

In many cases, distal vascular filters have a pore size larger than ~100 microns. Smaller sized embolic particle (e.g., having a cross-sectional diameter or dimension smaller than 100 microns) often comprise the preponderance of embolic debris and may not be captured by distal vascular filters. Hence, existing filters frequently fail to protect the distal vasculature against most of the liberated debris which is smaller than 100 microns, which can occlude the 8-10 micron capillaries and the variable sized 35-100 micron arterioles that supply vulnerable tissues of the foot and lower leg.

Distal embolic protection filters can have additional problems associated with their use, such as the creation of emboli during passage of the filter through the lesion to a distal location, landing zone issues (especially in BTK procedures where there may be none), spasm when the filter is expanded, intimal damage from movement during catheter/device exchanges over the supporting wire, inability to use a preferred guide wire, a lack of side branch protection between the interventional target site and the filter, overfill of the basket which may lead to embolic spill, difficulty in retrieval, debris leak from wall mal-apposition, difficulty removing a filter caught on a stent or anatomy of the patient, and lack of protection against small particles (<~100 microns), which make up the bulk of the embolic material. Because of the deficiencies of existing distal embolic protection filters and the fact that they do not capture most of the debris when utilized, the systems, devices, and methods described herein provide a welcome option for providing embolic protection to vascular beds, particularly the lower extremity, for example, to avoid deleterious effects of distal embolization which can result in delayed healing, persistence of chronic limb threatening ischemia, unexpected amputations and death, and generally poor outcomes.

The catheter-based devices and systems described herein may be utilized as a proximal embolic protection or proximal embolic prevention device. For example, a catheter-based device or system described herein can be used in a method comprising one or more of the following steps (not necessarily in the order listed): 1) inserting the catheter-based device with the expandable element aligned along an inner aspect (e.g., inner surface) of the outer catheter shaft (e.g., in a collapsed configuration) into a blood vessel, 2) navigating the device through the blood vessel to a position in close proximity to the target site, 2) expanding the expandable element (e.g., to an expanded configuration), thereby occluding flow proximal to the target site, 3) performing an interventional procedure at the target site comprising one or more of angioplasty, atherectomy, intravascular lithotripsy, drug coated balloon use, IVUS, stent placement, thrombectomy, CTO crossing and therapies, and infusion of medicaments, 4) aspirating one or more of blood, debris, emboli, thrombi, injected or inserted drugs or medicaments, and particulate matter from the target site, and 4) collapsing the expandable, and 5) removing a interventional device used in performing the interventional procedure and/or the catheter-based device or system from the target location (or vessel). In some cases, Step 3 above may be omitted. Alternatively, the interventional device may be removed after Step 3 is performed.

In some cases, systems, devices, and methods described herein can be useful in mitigating or eliminating problems that can arise in situations when a therapeutic drug (e.g., chemotherapeutic drug) is used. Paclitaxel and sirolimus are chemotherapeutic drug formulations commonly used to treat a variety of cancers. Paclitaxel, sirolimus and other anti-proliferative drugs and substances are used in drug coated balloons and drug coated stents for treatment of vascular disease to prevent re-stenosis, which is a process involving the body's reparative response to the intervention resulting in an exaggerated healing response and overgrowth of tissue which causes a delayed re-narrowing or restenosis of the artery. Particulate debris from the excipient, or coating formulation designed to transfer the drug from the balloon or stent to the tissues, may not be transferred to the tissues but may embolize to the distal tissues instead. While only a small percentage of the particulate excipient containing the drug embolizes, this particulate matter lodges in and blocks small distal arteries and arterioles where the drug is released and may further injure and cause further damage to an already vulnerable previously ischemic tissue. This may not be limited to inhibiting healing of the tissue (an aim of the intervention); it also may make matters worse because of the unintended injury resulting in delayed healing of ulcerations and, in lower extremity interventions, amputation of portions of the limb. Multiple scientific studies have indicated that drug coated balloons may be responsible for amputations and less than expected positive results. Essentially, the conundrum is that the drug from the drug coated balloon is advantageous to the target site lesion in preventing re-stenosis, but deleterious to the distal tissues by creating local ischemia by blocking the small vessels creating local and focal areas of ischemia and perfusing these tissues with a drug which inhibits healing in some, if not most, patients. This is a double insult to the friable tissues.

Furthermore, the drug coated balloon is frequently used after atherectomy or other debris liberating procedure which can result in showers of emboli to vulnerable tissue (and the resultant negative effects of focal ischemia) before the drug coated balloon administration and the embolization of drug laden particles. This can create an even worse environment for healing than if there were only drug laden debris blocking small vessels. Some patients are able to recover from suffering drug containing emboli from such procedures, but many are not, which can result in delayed healing and unnecessary amputations. Moreover, because of the progressive nature of vascular disease, these patients may be subjected to repeated re-interventions in the subsequent months and years. The cumulative effects of repeated injuries from repeated embolic events of particulate matter and drug containing particulate matter may further inhibit proper healing and could result in amputations, death, or other negative outcomes.

In many cases, the systems, devices, and methods described herein can benefit from advantageous effects of drug coated balloons and stents while precluding or limiting deleterious effects, which may inhibit re-stenosis (e.g., with the drug administration) while eliminating the embolization of harmful drug containing particulate matter to vulnerable tissues. A method of treating a blood vessel to inhibit restenosis while inhibiting or precluding the embolization of drug containing particulate matter can comprise 1) inserting a catheter-based device or system described herein (e.g., transcutaneously) into a lumen of a body cavity (such as the lumen of a blood vessel) and navigating it to a position proximal to a target site (e.g., an occluding lesion located in the blood vessel), 2) expanding an expandable element of the device or system, thereby occluding flow proximal to the target site, 3) performing an interventional procedure, which could comprise placement of a drug coated stent or a drug coated balloon inflation, 4) aspirating the target site of one or more of blood, debris, incipient emboli and drug containing particulate matter (e.g., subsequent to the interventional procedure), 4) collapsing the expandable element, and 5) removing the device or system from the lumen (e.g., the blood vessel).

Chronic total occlusions (CTOs) can occur in a blood vessel (e.g., an artery) when a stenosis or narrowing of the vessel (e.g., artery) gradually and completely occludes an artery. Plaque, organized thrombus, and calcifications can fill the entire lumen of the artery, frequently over a protracted length of the vessel. Restoration of blood flow through the CTO by interventional techniques can result in improved outcomes in both the coronary and peripheral circulation. Since the entire vessel lumen is filled with obstructing material, there can be a high likelihood, or even a certainty, of distal embolization of some of the obstructing material into downstream smaller arteries and arterioles. In some cases, an expandable element of a device or system described herein can be used to occlude flow proximal to a CTO, center and/or anchor a distal end of the device or system to support a guidewire or catheter crossing the CTO and support the intervention in disrupting the occlusion, and to prevent the embolization of the matter comprising the occlusion. A method of utilizing a catheter-based device or system disclosed herein to treat a chronic total occlusion of an artery can comprise one or more of the following steps: 1) inserting the catheter-based device or system proximal to the target site or CTO, 2) expanding the expandable element to an expanded configuration to occlude flow and, in some cases, to center and stabilize the distal end of the device or system within the vessel, 3) advancing a guide wire or catheter (or both) through the CTO, 4) performing a desired intervention to disrupt the CTO, 5) aspirating the liberated debris from the target site, 6) collapsing the expandable element, and 7) removing the catheter. In various embodiments, the removal of the interventional device may occur before or after Step 5.

In some CTOs the proximal end or cap of the CTO may be impenetrable by a guide wire and prevent antegrade crossing. In some such cases, a pedal or foot vessel may be accessed, and a guide wire can be passed retrograde through the softer distal end of the CTO and captured by a snare or into the tip of a catheter positioned proximally to the CTO and externalized. Then the intervention can proceed from an antegrade direction with a greater number of options for choosing a device for use in the procedure. In some cases, such a two-step access strategy can be time consuming and tedious or technically difficult, especially the capture and externalizing of the retrograde passed guide wire. An alternative method for treating a chronic total occlusion with a catheter-based device or system can comprise one or more steps selected from: 1) inserting a catheter-based device or system described herein to a site proximal to a CTO, 2) expanding the expandable element of the device or system to center and stabilize the distal funnel catheter tip within the vessel, 3) advancing a guide wire or catheter or both through the CTO, 4) alternatively or additionally (e.g., if step 3 is not successful), performing a retrograde puncture of a vessel distal to the CTO, 5) passing the guidewire through the CTO in a retrograde manner, 6) capturing the tip of the retrograde guidewire with the tip of the expandable element, 7) advancing the retrograde guidewire up a catheter shaft of the catheter-based device or system so that it is externalized at the proximal catheter insertion site, 8) then, whether over a previously inserted guide wire (e.g., if Step 3 is successful) or over a guidewire inserted retrograde (e.g., in the case Step 3 is unsuccessful), inserting an appropriate interventional device through a catheter shaft of the catheter-based device or system, 9) performing the desired intervention to disrupt the CTO, 10) aspirating the liberated debris from the target site, 11) collapsing the expanded expandable element and removing the catheter. In some cases, this method can save time, frustration, and potential vessel injury, which can be involved in attempting to capture the tip of the retrograde guidewire and externalize it primarily through a straw like catheter or with a snare assistance through a straw like catheter.

While preferred embodiments of the present inventions have been shown and described herein, it will be obvious to those skilled in the art that such embodiments are provided by way of example only. Numerous variations, changes, and substitutions will now occur to those skilled in the art without departing from the inventions. It should be understood that various alternatives to the embodiments of the inventions described herein may be employed in practicing the inventions. It is intended that the following claims define the scope of various inventions described herein and that methods and structures within the scope of these claims and their equivalents be covered thereby.

What is claimed is:

1. A method of removing a material from a blood vessel, comprising:
(a) advancing a device to a target site, wherein the device comprises:
(i) an outer catheter shaft;
(ii) an inner catheter shaft disposed at least partially within the outer shaft; and
(iii) an expandable element having a first end coupled to a distal end of the inner catheter shaft and a second end coupled to a distal end of the outer catheter shaft such that translation of the inner catheter shaft relative to the outer catheter shaft causes the expandable element to transition between an expanded configuration and a collapsed configuration, the expandable element having a funnel shape in the expanded configuration and a cylindrical tubular shape in the collapsed configuration, wherein an inner surface of the funnel shape is contiguous with an inner surface of the inner catheter shaft, wherein the expandable element is non-inflatable;
(b) translating at least one of the outer and inner catheter shafts of the device, thereby causing the expandable element to transform from a non-occlusive cylindrical shape to the expanded configuration with an outer cylindrical shape and an inner funnel shape, which occludes a blood flow and isolates a portion of the blood vessel containing a clot from the blood flow and exposes one or more apertures on the device to allow fluidic communication between a lumen of the inner catheter shaft and blood of the blood vessel;
(c) applying a negative pressure to a proximal end of the lumen of the inner catheter shaft; and
(d) applying suction to the portion of the blood vessel containing the clot and aspirating the clot from the portion of the blood vessel.

2. The method of claim 1, further comprising advancing the device by a force exerted on the expandable element by the blood flow.

3. The method of claim 1, further comprising performing an intervention at the target site using an interventional tool, aspirating the material liberated from the target site as a result of the intervention, removing the interventional tool, collapsing the expandable element, and removing the device from the blood vessel.

4. The method of claim 3, wherein the material comprises debris or incipient emboli, particulate matter, contrast media, and/or a drug from the interventional tool.

5. The method of claim 3, wherein the interventional tool is a drug coated balloon or a drug eluting balloon.

6. The method of claim 1, wherein the translating in (b) creates protective flow arrest proximal to the material at the target site of the blood vessel, and wherein the method comprises utilizing at least one maneuver to cause micro-movements of the material, the at least one maneuver comprising one or more of: 1) varying the suction forces applied to the proximal end of the inner shaft, 2) deploying and collapsing the expandable element a plurality of times, 3) providing sound or pressure waves to the material through the inner catheter shaft of the device, 4) inducing vibrations in the material using the device, and 5) administering fluids comprising one or more lytic agents to the material and applying negative pressure to a proximal end of a lumen of the inner catheter shaft to aspirate the material from the blood vessel.

7. The method of claim 6, wherein the at least one maneuver is sufficient to overcome one or more of (i) an impaction force of the material, (ii) friction between the material and a vessel wall, (iii) adhesive forces between the material and the vessel wall, or (iv) an internal consistency of the clot caused by the material.

8. The method of claim 1, wherein the one or more apertures are in a wall of the expandable element or the distal end of the inner catheter shaft.

9. The method of claim 1, further comprising creating inward flow of blood through the one or more apertures that introduces a fluid flow between the material and the inner surface of the inner catheter shaft to decrease a friction between the material and the inner surface of the inner catheter shaft.

10. The method of claim 1, wherein the negative pressure is applied and suddenly removed to cause recoil or movement of the material within the blood vessel or the inner catheter shaft.

11. The method of claim 10, wherein the negative pressure is applied and removed within 0.1 second or less.

12. The method of claim 10, wherein the recoil or movement is sufficient to overcome one or more of (i) an impaction force of the material, (ii) friction between the material and a vessel wall, (iii) adhesive forces between the material and the vessel wall, or (iv) an internal consistency of the clot caused by the material which precludes aspiration into a smaller channel.

13. The method of claim 12, further comprising applying an additional negative pressure to the proximal end of the lumen of the inner catheter shaft until all of the material is removed from the blood vessel.

14. The method of claim 13, wherein the additional negative pressure is applied and suddenly removed two or more times in succession.

15. The method of claim 1, further comprising providing traction to the clot using a clot retractor while applying the negative pressure to the proximal end of the lumen of the inner catheter shaft.

16. The method of claim 1, further comprising withdrawing the inner catheter shaft inside of the outer catheter shaft after application of the negative pressure, wherein the inner catheter shaft is disposed at least partially within and coaxial in relationship to the outer catheter shaft.

17. The method of claim 1, wherein the translating in (b) causes the expandable element to expand against a vessel wall and anchor to the vessel wall with full occlusion, partial occlusion, or no occlusion.

18. A method of preventing fragmentation and distal embolization of a thrombus during thrombus removal from a target site of a blood vessel, the method comprising:

(a) introducing a protective flow arrest device into the blood vessel in close proximity to the target site;

(b) occluding the blood vessel to blood flow with the protective flow arrest device by expanding an expandable element of the protective flow arrest device, wherein the protective flow arrest device comprises an outer catheter shaft and an inner catheter shaft disposed at least partially within the outer catheter shaft and the expandable element has a first end coupled to a distal end of the inner catheter shaft and a second end coupled to a distal end of the outer catheter shaft; wherein expanding the expandable element comprises translating at least one of the outer and inner shafts to expose one or more apertures on the protective flow arrest device and allow fluidic communication between a lumen of the inner catheter shaft and blood of the blood vessel;

(c) applying a negative pressure to a proximal end of the lumen of the protective flow arrest device;

(d) aspirating the thrombus while occluding the blood vessel;

(e) aspirating the thrombus through the protective flow arrest device;

(f) transitioning the expandable element of the protective flow arrest expandable element to a collapsed configuration; and (g) removing the protective flow arrest device from the blood vessel.

19. The method of claim 18, further comprising contacting the thrombus with a lytic agent prior to (a).

20. The method of claim 18, wherein (b) prevents disturbance of the thrombus from an antegrade blood flow.

* * * * *